(12) United States Patent
Ebel et al.

(10) Patent No.: US 8,962,656 B2
(45) Date of Patent: Feb. 24, 2015

(54) CCR2 ANTAGONISTS

(75) Inventors: Heiner Ebel, Biberach an der Riss (DE); Sara Frattini, Castelleone (IT); Riccardo Giovannini, Verona (IT); Christoph Hoenke, Biberach an der Riss (DE); Stefan Scheuerer, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/700,752

(22) PCT Filed: May 26, 2011

(86) PCT No.: PCT/EP2011/058668
§ 371 (c)(1),
(2), (4) Date: Feb. 6, 2013

(87) PCT Pub. No.: WO2011/151251
PCT Pub. Date: Dec. 8, 2011

(65) Prior Publication Data
US 2013/0217728 A1   Aug. 22, 2013

(30) Foreign Application Priority Data
Jun. 1, 2010   (EP) .................... 10164628

(51) Int. Cl.
*A61K 31/44* (2006.01)
*C07D 211/72* (2006.01)
*C07D 405/14* (2006.01)
*C07D 401/06* (2006.01)
*C07D 401/14* (2006.01)

(52) U.S. Cl.
CPC .......... *C07D 405/14* (2013.01); *C07D 401/06* (2013.01); *C07D 401/14* (2013.01)
USPC ........................................ 514/316; 546/316

(58) Field of Classification Search
None
See application file for complete search history.

(56) References Cited

U.S. PATENT DOCUMENTS

| | | | |
|---|---|---|---|
| 4,032,526 A | 6/1977 | Cross et al. | |
| 5,629,325 A * | 5/1997 | Lin et al. ........ | 514/318 |
| 5,631,269 A | 5/1997 | Broughton et al. | |
| 6,127,386 A | 10/2000 | Lin et al. | |
| 6,143,892 A | 11/2000 | Graneto et al. | |
| 6,423,713 B1 | 7/2002 | Anantanarayan et al. | |
| 6,437,138 B1 | 8/2002 | Lin et al. | |
| 6,514,977 B1 | 2/2003 | Anantanarayan et al. | |
| 6,806,279 B2 | 10/2004 | Arkin et al. | |
| 6,979,686 B1 | 12/2005 | Naraian et al. | |
| 7,504,511 B2 | 3/2009 | Carayon et al. | |
| 7,507,740 B2 | 3/2009 | Ishikawa et al. | |
| 7,612,201 B2 | 11/2009 | Beswick et al. | |
| 7,777,041 B2 | 8/2010 | Carayon et al. | |
| 7,807,671 B2 | 10/2010 | Wang et al. | |
| 7,891,384 B2 | 2/2011 | Binet et al. | |
| 7,915,261 B2 | 3/2011 | Ishii et al. | |
| 7,919,494 B2 | 4/2011 | Ishii et al. | |
| 7,919,495 B2 | 4/2011 | Ishii et al. | |
| 7,947,684 B2 * | 5/2011 | Pauls et al. ........ | 514/252.1 |
| 8,110,575 B2 | 2/2012 | Gottschling et al. | |
| 8,288,540 B2 * | 10/2012 | Chianelli et al. ........ | 544/331 |
| 2003/0195195 A1 * | 10/2003 | Haviv et al. ........ | 514/218 |
| 2004/0014744 A1 * | 1/2004 | Haviv et al. ........ | 514/218 |
| 2004/0147561 A1 | 7/2004 | Zhong et al. | |
| 2004/0220171 A1 | 11/2004 | Pauls et al. | |
| 2005/0192302 A1 | 9/2005 | Xue et al. | |
| 2005/0222151 A1 | 10/2005 | Carruthers et al. | |
| 2005/0245537 A1 | 11/2005 | Tsuchimori et al. | |
| 2006/0004049 A1 | 1/2006 | Yao et al. | |
| 2006/0030557 A1 | 2/2006 | Haviv et al. | |
| 2006/0173012 A1 | 8/2006 | Hohlweg | |
| 2007/0032475 A1 | 2/2007 | Ye et al. | |
| 2007/0032489 A1 * | 2/2007 | Weintraub et al. ........ | 514/235.2 |
| 2007/0244132 A1 | 10/2007 | Ishikawa et al. | |
| 2007/0281936 A1 | 12/2007 | Gillespie et al. | |
| 2008/0161280 A1 | 7/2008 | Gandhi et al. | |
| 2008/0306046 A1 | 12/2008 | Ishii et al. | |
| 2009/0048238 A1 | 2/2009 | Aebi et al. | |

(Continued)

FOREIGN PATENT DOCUMENTS

| | | | |
|---|---|---|---|
| CA | 2687931 A1 | 12/2008 | |
| CA | 2704883 A1 | 5/2009 | |

(Continued)

OTHER PUBLICATIONS

Chemical Abstracts Service, Columbus, OH, US, STN Database, accession No. 837395-83-2, compounds 837395-83-2.

(Continued)

*Primary Examiner* — Heidi Reese
(74) *Attorney, Agent, or Firm* — Michael P. Morris; Edward S. Lazer

(57) ABSTRACT

The present invention relates to novel antagonists for CCR2 (CC chemokine receptor 2) of formula (Ia) and their use for providing medicaments for treating conditions and diseases, especially pulmonary diseases like asthma and COPD.

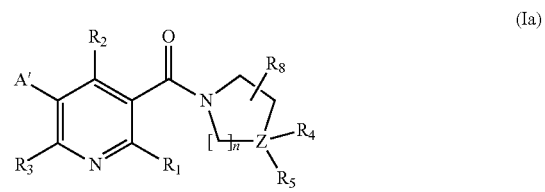

(Ia)

15 Claims, No Drawings

(56) References Cited

U.S. PATENT DOCUMENTS

| | | | |
|---|---|---|---|
| 2009/0131417 A1* | 5/2009 | Letavic et al. ............... | 514/218 |
| 2009/0318467 A1 | 12/2009 | Adam et al. | |
| 2010/0009971 A1 | 1/2010 | Ishii et al. | |
| 2010/0009972 A1 | 1/2010 | Ishii et al. | |
| 2010/0164159 A1 | 7/2010 | Wurthele | |
| 2010/0204209 A1 | 8/2010 | Ebel et al. | |
| 2010/0204230 A1 | 8/2010 | Blurton et al. | |
| 2011/0021500 A1 | 1/2011 | Gottschling et al. | |
| 2011/0183957 A1 | 7/2011 | Wityak et al. | |
| 2011/0195954 A1 | 8/2011 | Gottschling et al. | |
| 2011/0301143 A1 | 12/2011 | Isabel et al. | |
| 2012/0004252 A1 | 1/2012 | Ebel et al. | |
| 2012/0053164 A1 | 3/2012 | Ebel et al. | |
| 2012/0088754 A1 | 4/2012 | Van Emelen et al. | |
| 2012/0108572 A1 | 5/2012 | Wagner et al. | |
| 2013/0090338 A1 | 4/2013 | Ebel et al. | |
| 2013/0123241 A1 | 5/2013 | Ebel et al. | |
| 2013/0150354 A1 | 6/2013 | Ebel et al. | |
| 2013/0172348 A1 | 7/2013 | Ebel et al. | |
| 2013/0184299 A1 | 7/2013 | Ebel et al. | |
| 2013/0217728 A1 | 8/2013 | Ebel et al. | |
| 2013/0324517 A1 | 12/2013 | Ebel et al. | |

FOREIGN PATENT DOCUMENTS

| | | | |
|---|---|---|---|
| CA | 2705405 A1 | 5/2009 | |
| EP | 1752457 A1 | 2/2007 | |
| EP | 1849773 A1 | 10/2007 | |
| FR | 2854158 A1 | 10/2004 | |
| GB | 2068961 A | 8/1981 | |
| JP | 6229575 | 8/1994 | |
| JP | 2008239617 A | 10/2008 | |
| JP | 2007500135 | 1/2011 | |
| WO | 8606719 A1 | 11/1986 | |
| WO | 9921834 A1 | 5/1999 | |
| WO | WO 0046203 A2 * | 8/2000 | |
| WO | 0059502 A1 | 10/2000 | |
| WO | 0066558 A1 | 11/2000 | |
| WO | 0190101 A1 | 11/2001 | |
| WO | 03037271 A2 | 5/2003 | |
| WO | 03051797 A2 | 6/2003 | |
| WO | 03066604 A2 | 8/2003 | |
| WO | 03074500 A2 | 9/2003 | |
| WO | 03104223 A1 | 12/2003 | |
| WO | 2004024710 A1 | 3/2004 | |
| WO | 2004074438 A2 | 9/2004 | |
| WO | 2004080976 A1 | 9/2004 | |
| WO | 2004101546 A1 | 11/2004 | |
| WO | 2005009976 A1 | 2/2005 | |
| WO | 2005014571 A1 | 2/2005 | |
| WO | 2005060665 A2 | 7/2005 | |
| WO | 2005084667 A1 | 9/2005 | |
| WO | 2005097751 A2 | 10/2005 | |
| WO | 2005117909 A2 | 12/2005 | |
| WO | 2005118588 A1 | 12/2005 | |
| WO | 2006001958 A2 | 1/2006 | |
| WO | 2006003277 A1 | 1/2006 | |
| WO | 2006004741 A2 | 1/2006 | |
| WO | 2006012135 A1 | 2/2006 | |
| WO | 2006021801 A1 | 3/2006 | |
| WO | 2006029906 A1 | 3/2006 | |
| WO | 2006034440 A2 | 3/2006 | |
| WO | 2006034833 A1 | 4/2006 | |
| WO | 2006038734 A1 | 4/2006 | |
| WO | 2006050389 A2 | 5/2006 | |
| WO | 2006072350 A1 | 7/2006 | |
| WO | 2006073592 A2 | 7/2006 | |
| WO | 2006088075 A1 | 8/2006 | |
| WO | 2006113261 | 10/2006 | |
| WO | 2006113704 A2 | 10/2006 | |
| WO | 2007003604 A2 | 1/2007 | |
| WO | 2007016496 A2 | 2/2007 | |
| WO | 2007022937 A1 | 3/2007 | |
| WO | 2007026959 A2 | 3/2007 | |
| WO | 2007030061 A1 | 3/2007 | |
| WO | 2007038669 A2 | 4/2007 | |
| WO | 2007048779 A1 | 5/2007 | |
| WO | 2007053495 A2 | 5/2007 | |
| WO | 2007053498 A1 | 5/2007 | |
| WO | 2007074438 A2 | 7/2007 | |
| WO | 2007084786 A1 | 7/2007 | |
| WO | 2007084868 A2 | 7/2007 | |
| WO | 2007092065 A2 | 8/2007 | |
| WO | 2007100851 A1 | 9/2007 | |
| WO | 2007105058 A2 | 9/2007 | |
| WO | 2007120574 A2 | 10/2007 | |
| WO | 2007127448 A2 | 11/2007 | |
| WO | 2007147874 A1 | 12/2007 | |
| WO | 2008083027 A1 | 7/2008 | |
| WO | 2008145681 A2 | 12/2008 | |
| WO | 2008145861 A2 | 12/2008 | |
| WO | 2008151860 A1 | 12/2008 | |
| WO | 2009003861 A1 | 1/2009 | |
| WO | 2009013211 A2 | 1/2009 | |
| WO | 2009026204 A1 | 2/2009 | |
| WO | WO 2009026204 A1 * | 2/2009 | |
| WO | 2009043747 A2 | 4/2009 | |
| WO | 2009048238 A2 | 4/2009 | |
| WO | 2009065919 A2 | 5/2009 | |
| WO | 2009065920 A2 | 5/2009 | |
| WO | 2009153182 A1 | 12/2009 | |
| WO | 2010017179 A1 | 2/2010 | |
| WO | 2010020432 A2 | 2/2010 | |
| WO | 2010070032 A1 | 6/2010 | |
| WO | 2011073154 A1 | 6/2011 | |
| WO | 2011073155 A1 | 6/2011 | |
| WO | 2011141474 A1 | 11/2011 | |
| WO | 2011141477 A1 | 11/2011 | |
| WO | 2011144501 A1 | 11/2011 | |
| WO | 2011147772 A1 | 12/2011 | |
| WO | 2011151251 A1 | 12/2011 | |
| WO | 2012171863 A1 | 12/2012 | |
| WO | 2013010839 A1 | 1/2013 | |

OTHER PUBLICATIONS

Chemical Abstracts Service, Columbus, OH, US, STN Database, accession No. 837396-471 compounds 837396-471.

Chabner, Bruce, A., et al; Chemotherapy of Neoplastic Diseases: Antineoplastic Agents: Goodman & Gilman's: The Pharmacological Basis of Therapeutics by Laurence L. Brunton et al (2006) 11th Ed. pp. 1315-1403.

Chemical Abstracts Service, Columbus, OH, US, Yamashita, Hiroshi et al: "Preparation of benzothiophenylpiperazine derivatives for treatment of central nervous system diseases", XP002528684 retrieved from STN. Database accession No. 2008:1217060, Compound RN: 928251-63-2 *abstract* & JP 2008 239617 A (Ohtsuka Pharmaceutical Co., Ltd, Japan) Oct. 9, 2008.

Chemical Abstracts Service, Columbus, OH; US; Ledeboer; Mark W. et al: "Pyrrolopyridines useful as inhibitors of protein kinase and their prepration, pharmaceutical compositions, and use in the treatment of various diseases", XP002528685 retrieved from STN, Database accession No. 2006:1252802 Compounds RN: 916172-93-5, 916172-95-7 *abstract* & WO 2006/127587 A1 (Vertex Pharmaceuticals Incorporated; USA) Nov. 30, 2006.

Cuzzocrea, Salvstore; Shock, Inflammation and PARP; Pharmacological Research (2005) vol. 52 pp. 72-82.

Poupaert, Jacques, H; Drug Design: Basic Principles and Applications; Encyclopedia of Pharmaceutical Technology (2007) 3rd edition pp. 1362-1369.

U.S. Appl. No. 13/949,696, filed Jul. 24, 2013, Inventor: Heiner Ebel.

Notice of Abandonment mailed Aug. 16, 2013, for U.S. Appl. No. 13/140,591, filed Aug. 10, 2011. Inventor: Heiner Ebel.

Cannon, J.G., et al., Chapter Nineteen in Burger's Medicinal Chemistry and Drug Discovery, Fifth Edition, vol. 1., Principals and Practice, Wiley-Interscience 1995, p. 783-802, 784.

Sheridan, R.P., et al., "The Most Common Chemical Replacements in drug-like compounds", J. Chem. Inf. Comp. Sci., 2002, V. 42, p. 103-108.

(56) References Cited

OTHER PUBLICATIONS

Rival, Y. et al., "5-HT3 Antagonists Derived from Aminopyridazine-type Muscarinic M1 Agonists", Journal of Medicinal Chemistry, 1998, V.41, p. 311-317.
Wenhui, Hu. et al., "Development of anovel therapeutic suppressor of brain proinflammatory cytokine up-regulation that attenuates synaptic dysfunction and behavioural deficits", Bioorg. Medicine Chem. Letter, 2007, v. 17, p. 414-418.
Castro, ME, et al., "Prridazine derivatives XII. Synthesis and antipsychotic-antidepressant activity of some butyrophenone derivatives of 6-phenylpyridazine", European Journal of Medicinal Chemistry, 1994, v. 29, p. 831-839.
E.A. Steck et al., "Some 6-Aryl-3-(basically-substituted) Pyridazines", Journal of Heterocyclic Chemistry, 1975, v. 12, No. 5, p. 1009-1013.
Refaat, Hanan, et al., "Bulletin of the Faculty of Pharmacy", (Cair University) Database Caplus on STN, Entered STN 2005, vol. 42, No. 2, p. 415-423.
Hiroshi, et al., "Preparation of benzothiophenylpiperazine derivatives for treatment of central nervous system diseases", 2008, Chemical Abstracts Service, retrieved from STN database succession No. 2008:1217060, Compound RN:92851-63-2.
Mark, W. et al., "Pyrrolopyridines useful as inhibitors of protein kinase and their preparation, pharmaceutical compositions, and use in the treatment of various diseases", Chemical Abstracts Service, 2006.
Cuzzocrea, "Shock, Inflammation and PARP", Pharmacology Res. Acad. Press, 2005, vol. 52, No. 1, p. 72-82.
Ledeboer, Mark W. et al., "Pyrrolopypyridines useful as inhibitors of protein kinase and their preparation, pharmaceutical compositions, and use in the treatment of various diseases", 2006, Chemical Abstracts Service.
Hiroshi, et al., "Preparation of benzothiophenylpiperazine derivatives for treatment of central nervous system diseases", Chemical Abstracts Service, 2008.
Hawtin, et al., AGly/Ala switch contributes to high affinity bonding of benzoxazinone-based non-peptide oxytocin receptor antagonists, 2005, FEBS letters, vol. 579, p. 349-356.
Xia, et al., Johnson and Johnson Pharmaceutical Research, "Recent Developments in CCR2 antagonists", 2009, p. 295-303.
Abbadie, et al., 100 PNAS "Impaired neuropathic pain responses in mice lacking the chemokine receptor CCR2", p. 7947-7952 (2003).
Barnes, Nature Reviews Drug Study, "New Treatments for COPD", 2003, p. 437-446.
Havlioglu, et al., "Slit Proteins Potential Endogenous Modulators of Information", Neurovirology, 8, p. 786-495, 2002.
Barril, Xavier, et al; 4-Amino Derivates of the Hsp90 Inhibitor CCT018159; Bioorganic & Medicinal Chemistry Letters (2006) vol. 16 p. 2543-2548.
Carter, Percy, H., et al; Advances in the Discovery of CC Chemokine Receptor 2 Antagonists; Annual Reports in Medicinal Chemistry (2007) vol. 42 pp. 211-228.

Chemical Abstracts Service, Columbus, OH, US, STN Database, accession No. 837395-83-2, compounds 837395-83-2, 2005.
Chemical Abstracts Service, Columbus, OH, US, STN Database, accession No. 837396-471 compounds 837396-471, 2005.
Donnelly, Louise, E., et al; Chemokine Receptors as Therapeutic Targets in Chronic Obstructive Pulmonary Disease; Trends in Pharmacological Sciences (2006) vol. 27, No. 10 pp. 546-553.
Hu, Wenhui, et al; Development of a Novel Therapeutic Suppressor of Brain Proinflammatory Cytokine Up-Regulation that Attenuates Synaptic Dysfunction and Behavioral Deficits; Science Direct; Bioorganic & Medicinal Chemistry Letters (2007) vol. 17 pp. 414-418.
International Preliminary Report on Patentability for PCT/EP2009/067378 Issued Jun. 21, 2011.
International Preliminary Report on Patentability for PCT/EP2010/069549 Issued Jun. 19, 2012.
International Search Report for PCT/EP2008/056573 mailed Jan. 14, 2009.
International Search Report for PCT/EP2009/067378 mailed Apr. 16, 2010.
International Search Report for PCT/EP2010/069549 mailed Feb. 23, 2011.
International Search Report for PCT/EP2010/069550 mailed Feb. 23, 2010.
International Search Report for PCT/EP2011/057539 mailed Jul. 20, 2011.
International Search Report for PCT/EP2011/057545 mailed Jul. 4, 2011.
International Search Report for PCT/EP2011/057550 mailed Jun. 28, 2011.
International Search Report for PCT/EP2011/058355 mailed Aug. 9, 2011.
International Search Report for PCT/EP2011/058668 mailed Jun. 28, 2011.
Kuettel, Sabine, et al; Synthesis and Evaluation of Antiparasitic Activities of New 4-[5-(4-Phenoxyphenyl)-2H-pyrazol-3-yl]morpholine Derivatives; Journal Med. Chem. (2007) vol. 50 pp. 5833-5839.
Lagu, Bharat, et al; Potent and Selective CC-Chemokine Receptor-2 (CCR2) Antagonists as a Potential Treatment for Asthma; Bioorganic and Medicinal Chemistry Letters (2007) vol. 17 pp. 4382-4386.
Rowley, Micheal, et al; 4-Heterocyclylpiperidines as Selective High-Affinity Ligands at the Human Dopamine D4 Receptor; J. Med. Chem (1997) vol. 40 pp. 2374-2385.
U.S. Appl. No. 13/523,220, filed Jun. 14, 2012.
U.S. Appl. No. 13/548,321, filed Jul. 13, 2012.
U.S. Appl. No. 13/696,859, filed Nov. 8, 2012.
U.S. Appl. No. 13/696,860, filed Nov. 8, 2012.
U.S. Appl. No. 13/698,065, filed Nov. 15, 2012.
U.S. Appl. No. 13/699,325, filed Nov. 21, 2012.
Xu, Ping, et al; Synthesis and Anticonvulsant Activity of 3-(substituted piperazino)-6-(substituted phenyl) pyridazines; Chemical Abstracts Service (1991) vol. 23, No. 6, pp. 477-480.

* cited by examiner

CCR2 ANTAGONISTS

FIELD OF INVENTION

The present invention relates to novel antagonists for CCR2 (CC chemokine receptor 2) and their use for providing medicaments for treating conditions and diseases where activation of CCR2 plays a causative role, especially pulmonary diseases like asthma and COPD, neurologic disease, especially of pain diseases, immune related diseases, especially diabetes mellitus including diabetes nephropathy, and cardiovascular diseases, especially atherosclerotic disease.

BACKGROUND OF THE INVENTION

The chemokines are a family of small, proinflammatory cytokines, with potent chemotatctic activities. Chemokines are chemotactic cytokines that are released by a wide variety of cells to attract various cells, such as monocytes, macrophages, T cells, eosinophils, basophils and neutrophils to sites of inflammation.

Chemokine receptors, such as CCR2 or CCR5 have been implicated as being important mediators of inflammatory and immunoregulatory disorders and diseases as well as autoimmune pathologies such as rheumatoid arthritis and atherosclerosis. Accordingly, agents which modulate chemokine receptors such as the CCR2 and CCR5 receptor would be useful in such disorders and diseases.

In particular it is widely accepted that numerous conditions and diseases involve inflammatory processes. Such inflammations are critically triggered and/or promoted by the activity of macrophages, which are formed by differentiation out of monocytes. It has further been found that monocytes are characterized by, e.g., a high expression of membrane-resident CCR2, whereas the CCR2 expression in macrophages is lower. CCR2 is a critical regulator of monocytes trafficking, which can be described as the movement of the monocytes towards an inflammation along a gradient of monocyte chemoattractant proteins (MCP-1, MCP-2, MCP-3, MCP-4).

Therefore, in order to reduce macrophage-induced inflammation, it would be desirable to block the monocyte CCR2 by an antagonist, so that the monocytes can be less triggered to move towards an inflammation area for conversion into macrophages.

Based on the aforesaid there is a need for providing effective antagonists for CCR2, which are pharmacologically acceptable.

DESCRIPTION OF THE INVENTION

It has now been found that such effective CCR2 inhibitors can be provided by compounds according to general formula (Ia),

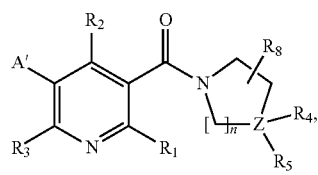

(Ia)

wherein A' is selected from among $-L_1-R_7$, $-HC=L_1-R_7$, $-CH_2-L_1-R_7$, $-S-L_1-R_7$, $-NH-L_1-R_7$, and the structure (III)

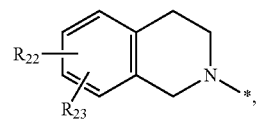

(III)

wherein $L_1$ is a linker selected from a bond or a group selected from among $-C_1-C_2$-alkylene, and $-C_1-C_2$-alkenylene which optionally comprises one or more groups selected from $-O-$, $-C(O)-$, and $-NH-$ in the chain and which is optionally substituted by a group selected from among $-OH$, $-NH_2$, $-C_1-C_3$-alkyl, $O-C_1-C_6$-alkyl, and $-CN$, wherein $R_7$ is a ring selected from among $-C_3-C_8$-cycloalkyl, $-C_3-C_8$-heterocyclyl, aryl, and $-C_5-C_{10}$-heteroaryl, wherein the ring $R_7$ is optionally substituted with one or more groups selected from among $-CF_3$, $-O-CF_3$, $-CN$, $-C_1-C_6$-alkenyl, and $-C_1-C_6$-alkynyl, and -halogen, or wherein the ring $R_7$ is optionally substituted with one or more groups selected from among $-C_5-C_{10}$-aryl, $-C_5-C_{10}$-heteroaryl, $-C_3-C_8$-cycloalkyl, $-C_3-C_8$-heterocyclyl, optionally being substituted by one or more groups selected from among $-OH$, $-NH_2$, $-C_1-C_4$-alkyl, alkyl, $-CN$, $-CF_3$, $-OCF_3$, halogen, and $=O$, or wherein the ring $R_7$ is optionally further bi-valently substituted on two neighbouring ring atoms, such that an annellated ring is formed by one or more groups selected from among $-C_1-C_6$-alkylene, $-C_2-C_6$-alkenylene and $-C_4-C_6$-alkynylene, in which one or two carbon centers may optionally be replaced by 1 or 2 hetero atoms selected from N, O and S, the bivalent group being optionally substituted by one or more groups selected from $-OH$, $-NH_2$, $-C_1-C_4$-alkyl, $-O-C_1-C_6$-alkyl, $-CN$, $-CF_3$, $-OCF_3$, halogen, and $=O$, wherein $R_{22}$ is selected from among $-H$, $-OH$, $-NH_2$, $-C_1-C_4$-alkyl, $-O-C_1-C_6$-alkyl, $-CN$, $-CF_3$, $-OCF_3$, halogen, and $=O$, wherein $R_{23}$ is selected from among $-H$, $-OH$, $-NH_2$, $-C_1-C_4$-alkyl, $-O-C_1-C_6$-alkyl, $-CN$, $-CF_3$, $-OCF_3$, halogen, and $=O$;

wherein $R_1$ is selected from among $-H$, -methyl, -ethyl, -propyl, -i-propyl, -cyclopropyl, $-OCH_3$, $-OH$, and $-CN$;

wherein $R_2$ is selected from among $-H$, -halogen, $-CN$, $-O-C_1-C_4$-alkyl, $-C_1-C_4$-alkyl, $-CH=CH_2$, -cyclopropyl, $-CF_3$, $-OCF_3$, $-OCF_2H$, and $-OCFH_2$;

wherein $R_3$ is selected from among $-H$, -methyl, -ethyl, -propyl, -i-propyl, -cyclopropyl, $-OCH_3$, $-OH$, and $-CN$;

wherein $R_6$ is selected from among $-H$, $-C_1-C_4$-alkyl, $-OH$, $-O-C_1-C_4$-alkyl, -halogen, $-CN$, $-CF_3$, and $-OCF_3$;

wherein Z is C or N;

wherein n is 1, 2 or 3;

wherein $R_4$ and $R_5$ are independently selected from among an electron pair, $-H$, and a group selected from among $-C_1-C_6$-alkyl, $-NH_2$, $-C_3-C_8$-cycloalkyl, $-C_3-C_8$-heterocyclyl, $-C_5-C_{10}$-aryl, $-C_5-C_{10}$-heteroaryl, and $-C(O)-N(R_8,R_{8'})$, with $R_8$ and $R_{8'}$ independently being selected from among $-H$, and $-C_1-C_6$-alkyl, and wherein $R_4$ and $R_5$ if different from an electron pair or $-H$ are optionally independently substituted with one or more groups selected from among -halogen, $-OH$, $-CF_3$, $-CN$, $-C_1-C_6$-alkyl, $-O-C_1-C_6$-alkyl, $-O-C_3-C_8$-cycloalkyl, $-O-C_3-C_8$-heterocyclyl, $-O-C_5-C_{10}$-aryl, $-O-C_5-C_{10}$-heteroaryl, $-C_0-C_6$-alkylene-CN, $-C_0-C_4$-alkylene-O-$C_1-C_4$-alkyl, $-C_0-C_4$-alkylene-O-$C_3-C_8$-cycloalkyl, —C$_0$-C$_4$-alkylene-O—C$_3$-C$_8$-heterocyclyl, —C$_0$-C$_4$-alkylene-O—C$_5$-C$_{10}$-aryl, —C$_0$-C$_4$-alkylene-O—C$_5$-C$_{10}$-heteroaryl, —C$_0$-C$_4$-alkylene-Q-C$_0$-C$_4$-alkyl-N(R$_9$,R$_{9'}$), —C$_0$-C$_4$-alkylene-N(R$_{10}$)-Q-C$_1$-C$_4$-alkyl, —C$_0$-C$_4$-alkylene-N(R$_{10}$)-Q-C$_3$-C$_8$-cycloalkyl, —C$_0$-C$_4$-alkylene-N(R$_{10}$)-Q-C$_3$-C$_8$-heterocyclyl, —C$_0$-C$_4$-alkylene-N(R$_{10}$)-Q-C$_5$-C$_{10}$-aryl, —C$_0$-C$_4$-alkylene-N(R$_{10}$)-Q-C$_5$-C$_{10}$-heteroaryl, —C$_0$-C$_4$-alkylene-Q-N(R$_{11}$,R$_{11'}$), —C$_0$-C$_4$-alkylene-N(R$_{12}$)-Q-N(R$_{13}$,R$_{13'}$), —C$_0$-C$_4$-alkylene-R$_{14}$, —C$_0$-C$_4$-alkylene-Q-C$_1$-C$_6$-alkyl, —C$_0$-C$_4$-alkylene-Q-C$_3$-C$_8$-cycloalkyl, —C$_0$-C$_4$-alkylene-Q-C$_3$-C$_8$-heterocyclyl, —C$_0$-C$_4$-alkylene-Q-C$_5$-C$_{10}$-aryl, —C$_0$-C$_4$-alkylene-Q—C$_5$-C$_{10}$-heteroaryl, —C$_0$-C$_4$-alkylene-O-Q-N(R$_{15}$,R$_{15'}$), and —C$_0$-C$_4$-alkylene-N(R$_{16}$)-Q-O—(R$_{17}$), wherein Q is selected from among —C(O)—, and —SO$_2$—, wherein R$_{12}$, R$_{16}$, are independently selected from among —H, —C$_1$-C$_6$-alkyl, and —C$_3$-C$_6$-cycloalkyl, wherein R$_9$, R$_{9'}$, R$_{10}$, R$_{11}$, R$_{11'}$, R$_{13}$, R$_{13'}$, R$_{15}$, R$_{15'}$ are independently selected from among —H, —C$_1$-C$_6$-alkyl, and —C$_3$-C$_6$-cycloalkyl, or wherein R$_9$ and R$_{9'}$, R$_{11}$ and R$_{11'}$, R$_{13}$ and R$_{13'}$, R$_{15}$ and R$_{15'}$ together form a —C$_2$-C$_6$-alkylene group, wherein R$_{14}$ and R$_{17}$ are independently selected from among —H, —C$_1$-C$_6$-alkyl, C$_5$-C$_{10}$ aryl, —C$_5$-C$_{10}$-heteroaryl, —C$_3$-C$_8$-cycloalkyl, and —C$_3$-C$_8$-heterocyclyl, wherein said —C$_3$-C$_8$-heterocyclyl optionally comprises nitrogen and/or —SO$_2$— in the ring, and wherein R$_{14}$ and R$_{17}$ are optionally substituted with one or more groups selected from among —OH, —OCH$_3$, —CF$_3$, —OCF$_3$, —CN, -halogen, —C$_1$-C$_4$-alkyl, =O, and —SO$_2$—C$_1$-C$_4$-alkyl, or wherein R$_4$ and/or R$_5$ are independently selected from among an electron pair, —H, and a group of the structure -L$_2$-R$_{18}$, wherein L$_2$ is selected from among —NH— and —N(C$_1$-C$_4$-alkyl)-, wherein R$_{18}$ is selected from among —C$_5$-C$_{10}$-aryl, —C$_5$-C$_{10}$-heteroaryl, —C$_3$-C$_8$-cycloalkyl, and —C$_3$-C$_8$-heterocyclyl, wherein R$_{18}$ is optionally substituted by one or more groups selected from among halogen, —CF$_3$, —OCF$_3$, —CN, —OH, —O—C$_1$-C$_4$-alkyl, —C$_1$-C$_6$-alkyl, —NH—C(O)—C$_1$-C$_6$-alkyl, alkyl)-C(O)—C$_1$-C$_6$-alkyl, —C(O)—C$_1$-C$_6$-alkyl, —S(O)$_2$—C$_1$-C$_6$-alkyl, —NH—S(O)$_2$—C$_1$-C$_6$-alkyl, —N(C$_1$-C$_4$-alkyl)-S(O)$_2$—C$_1$-C$_6$-alkyl, and —C(O)—O—C$_1$-C$_6$-alkyl, and wherein R$_4$, R$_5$ and R$_{18}$ are optionally further substituted by spiro-C$_3$-C$_8$-cycloalkyl or spiro-C$_3$-C$_8$-heterocyclyl such that together with R$_4$, R$_5$ and/or R$_{18}$ a spirocycle is formed, wherein said spiro-C$_3$-C$_8$-heterocyclyl optionally comprises one or more groups selected from among nitrogen, —C(O)—, —SO$_2$—, and —N(SO$_2$—C$_1$-C$_4$-alkyl)- in the ring, or wherein R$_4$, R$_5$ and R$_{18}$ are optionally further bi-valently substituted by one or more spirocyclic or annellated ring forming groups selected from among —C$_1$-C$_6$-alkylene, —C$_2$-C$_6$-alkenylene, and —C$_4$-C$_6$-alkynylene, in which one ore two carbon centers may optionally be replaced by one or two hetero atoms selected from among N, O and S and which may optionally be substituted by one or more groups on one ring atom or on two neighbouring ring atoms selected from among —OH, —NH$_2$, —C$_1$-C$_3$-alkyl, O—C$_1$-C$_6$-alkyl, —CN, —CF$_3$, —OCF$_3$, and halogen;

as well as in form of their acid addition salts with pharmacologically acceptable acids.

Another embodiment of the invention are compounds according to formula (I)

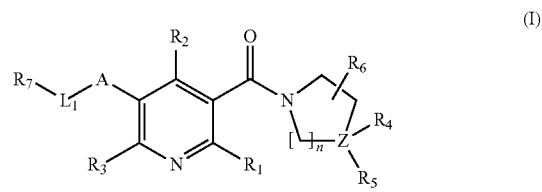

wherein
wherein A is selected from among a single bond, =CH—, —CH$_2$—, —O—, —S—, and —NH—;

wherein L$_1$ is a linker selected from a bond or a group selected from among —C$_1$-C$_2$-alkylene, and —C$_1$-C$_2$-alkenylene which optionally comprises one or more groups selected from —O—, —C(O)—, and —NH— in the chain and which is optionally substituted by a group selected from among —OH, —NH$_2$, —C$_1$-C$_3$-alkyl, O—C$_1$-C$_6$-alkyl, and —CN, wherein R$_7$ is a ring selected from among —C$_3$-C$_8$-cycloalkyl, —C$_3$-C$_8$-heterocyclyl, —C$_5$-C$_{10}$-aryl, and —C$_5$-C$_{10}$-heteroaryl, wherein the ring R$_7$ is optionally substituted with one or more groups selected from among —CF$_3$, —C$_1$-C$_6$-alkyl, —O—CF$_3$, —CN, —O—C$_1$-C$_6$-alkyl, —C$_1$-C$_6$-alkenyl, and —C$_1$-C$_6$-alkynyl, and -halogen, or wherein the ring R$_7$ is optionally substituted with one or more groups selected from among —C$_5$-C$_{10}$-aryl, —C$_5$-C$_{10}$-heteroaryl, —C$_3$-C$_8$-cycloalkyl, —C$_3$-C$_8$-heterocyclyl, optionally being substituted by one or more groups selected from among —OH, —NH$_2$, —C$_1$-C$_4$-alkyl, —O—C$_1$-C$_6$-alkyl, —CN, —CF$_3$, —OCF$_3$, halogen, and =O, or wherein the ring R$_7$ is optionally further bi-valently substituted on two neighbouring ring atoms, such that an annellated ring is formed by one or more groups selected from among —C$_1$-C$_6$-alkylene, —C$_2$-C$_6$-alkenylene and —C$_4$-C$_6$-alkynylene, in which one or two carbon centers may optionally be replaced by 1 or 2 hetero atoms selected from N, O and S, the bivalent group being optionally substituted by one or more groups selected from —OH, —NH$_2$, —C$_1$-C$_4$-alkyl, —O—C$_1$-C$_6$-alkyl, —CN, —CF$_3$, —OCF$_3$, halogen, and =O;

wherein R$_1$ is selected from among —H, -methyl, -ethyl, -propyl, -i-propyl, -cyclopropyl, —OCH$_3$, —OH, and —CN;
wherein R$_2$ is selected from among —H, -halogen, —CN, —O—C$_1$-C$_4$-alkyl, —C$_1$-C$_4$-alkyl, —CH=CH$_2$, -cyclopropyl, —CF$_3$, —OCF$_3$, —OCF$_2$H, and —OCFH$_2$;
wherein R$_3$ is selected from among —H, -methyl, -ethyl, -propyl, -i-propyl, -cyclopropyl, —OCH$_3$, —OH, and —CN;
wherein R$_6$ is selected from among —H, —C$_1$-C$_4$-alkyl, —OH, —O—C$_1$-C$_4$-alkyl, -halogen, —CN, —CF$_3$, and —OCF$_3$;
wherein Z is C or N;
wherein n is 1, 2 or 3;
wherein R$_4$ and R$_5$ are independently selected from among an electron pair, —H, and a group selected from among —C$_1$-C$_6$-alkyl, —NH$_2$, —C$_3$-C$_8$-cycloalkyl, —C$_3$-C$_8$-heterocyclyl, —C$_5$-C$_{10}$-aryl, —C$_5$-C$_{10}$-heteroaryl, and —C(O)—N(R$_8$,R$_{8'}$), with R$_8$ and R$_{8'}$ independently being selected from among —H, and —C$_1$-C$_6$-alkyl,
and wherein R$_4$ and R$_5$ if different from an electron pair or —H are optionally independently substituted with one or more groups selected from among -halogen, —OH, —CF$_3$, —CN, —C$_1$-C$_6$-alkyl, —O—C$_1$-C$_6$-alkyl, —O—C$_3$-C$_8$-cycloalkyl, —O—$C_3$-$C_8$-heterocyclyl, —O—$C_5$-$C_{10}$-aryl, —O—$C_5$-$C_{10}$-heteroaryl, —$C_0$-$C_6$-alkylene-CN, —$C_0$-$C_4$-alkylene-O—$C_1$-$C_4$-alkyl, —$C_0$-$C_4$-alkylene-O—$C_3$-$C_8$-cycloalkyl, —$C_0$-$C_4$-alkylene-O—$C_3$-$C_8$-heterocyclyl, —$C_0$-$C_4$-alkylene-O—$C_5$-$C_{10}$-aryl, —$C_0$-$C_4$-alkylene-O—$C_5$-$C_{10}$-heteroaryl, —$C_0$-$C_4$-alkylene-Q-$C_0$-$C_4$-alkyl-N($R_9$,$R_{9'}$), —$C_0$-$C_4$-alkylene-N($R_{10}$)-Q-$C_1$-$C_4$-alkyl, —$C_0$-$C_4$-alkylene-N($R_{10}$)-Q-$C_3$-$C_8$-cycloalkyl, —$C_0$-$C_4$-alkylene-N($R_{10}$)-Q-$C_3$-$C_8$-heterocyclyl, —$C_0$-$C_4$-alkylene-N($R_{10}$)-Q-$C_5$-$C_{10}$-aryl, —$C_0$-$C_4$-alkylene-N($R_{10}$)-Q-$C_5$-$C_{10}$-heteroaryl, —$C_0$-$C_4$-alkylene-Q-N($R_{11}$,$R_{11'}$), —$C_0$-$C_4$-alkylene-N($R_{12}$)-Q-N($R_{13}$,$R_{13'}$), —$C_0$-$C_4$-alkylene-$R_{14}$, —$C_0$-$C_4$-alkylene-Q-$C_1$-$C_6$-alkyl, —$C_0$-$C_4$-alkylene-Q-$C_3$-$C_8$-cycloalkyl, —$C_0$-$C_4$-alkylene-Q-$C_3$-$C_8$-heterocyclyl, —$C_0$-$C_4$-alkylene-Q-$C_5$-$C_{10}$-aryl, —$C_0$-$C_4$-alkylene-Q-$C_5$-$C_{10}$-heteroaryl, —$C_0$-$C_4$-alkylene-O-Q-N($R_{15}$,$R_{15'}$), and —$C_0$-$C_4$-alkylene-N($R_{16}$)-Q-O—($R_{17}$), wherein Q is selected from among —C(O)—, and —$SO_2$—, wherein $R_{12}$, $R_{16}$, are independently selected from among —H, —$C_1$-$C_6$-alkyl, and —$C_3$-$C_6$-cycloalkyl, wherein $R_9$, $R_{9'}$, $R_{10}$, $R_{11}$, $R_{11'}$, $R_{13}$, $R_{13'}$, $R_{15}$, $R_{15'}$, are independently selected from among —H, —$C_1$-$C_6$-alkyl, and —$C_3$-$C_6$-cycloalkyl, or wherein $R_9$ and $R_{9'}$, $R_{11}$ and $R_{11'}$, $R_{13}$ and $R_{13'}$, $R_{15}$ and $R_{15'}$ together form a —$C_2$-$C_6$-alkylene group, wherein $R_{14}$ and $R_{17}$ are independently selected from among —H, —$C_1$-$C_6$-alkyl, —$C_5$-$C_{10}$-aryl, —$C_5$-$C_{10}$-heteroaryl, —$C_3$-$C_8$-cycloalkyl, and —$C_3$-$C_8$-heterocyclyl, wherein said —$C_3$-$C_8$-heterocyclyl optionally comprises nitrogen and/or —$SO_2$— in the ring, and wherein $R_{14}$ and $R_{17}$ are optionally substituted with one or more groups selected from among —OH, —$OCH_3$, —$CF_3$, —$OCF_3$, —CN, -halogen, —$C_1$-$C_4$-alkyl, =O, and —$SO_2$—$C_1$-$C_4$-alkyl, or wherein $R_4$ and/or $R_5$ are independently selected from among an electron pair, —H, and a group of the structure -$L_2$-$R_{18}$, wherein $L_2$ is selected from among —NH— and —N($C_1$-$C_4$-alkyl)-, wherein $R_{18}$ is selected from among —$C_5$-$C_{10}$-aryl, —$C_5$-$C_{10}$-heteroaryl, —$C_3$-$C_8$-cycloalkyl, and —$C_3$-$C_8$-heterocyclyl, wherein $R_{18}$ is optionally substituted by one or more groups selected from among halogen, —$CF_3$, —CN, —OH, —O—$C_1$-$C_4$-alkyl, —$C_1$-$C_6$-alkyl, —N($C_1$-$C_4$-alkyl)-C(O)—$C_1$-$C_6$-alkyl, —C(O)—$C_1$-$C_6$-alkyl, —S(O)$_2$—$C_1$-$C_6$-alkyl, —NH—S(O)$_2$—$C_1$-$C_6$-alkyl, —N($C_1$-$C_4$-alkyl)-S(O)$_2$—$C_1$-$C_6$-alkyl, and —C(O)—O—$C_1$-$C_6$-alkyl, and wherein $R_4$, $R_5$ and $R_{18}$ are optionally further substituted by spiro-$C_3$-$C_8$-cycloalkyl or spiro-$C_3$-$C_8$-heterocyclyl such that together with $R_4$, $R_5$ and/or $R_{18}$ a spirocycle is formed, wherein said spiro-$C_3$-$C_8$-heterocyclyl optionally comprises one or more groups selected from among nitrogen, —C(O)—, —$SO_2$—, and —N($SO_2$—$C_1$-$C_4$-alkyl)- in the ring, or wherein $R_4$, $R_5$ and $R_{18}$ are optionally further bi-valently substituted by one or more spirocyclic or annellated ring forming groups selected from among —$C_1$-$C_6$-alkylene, —$C_2$-$C_6$-alkenylene, and —$C_4$-$C_6$-alkynylene, in which one ore two carbon centers may optionally be replaced by one or two hetero atoms selected from among N, O and S and which may optionally be substituted by one or more groups on one ring atom or on two neighbouring ring atoms selected from among —OH, —$NH_2$, —$C_1$-$C_3$-alkyl, O—$C_1$-$C_6$-alkyl, —CN, —$CF_3$, —$OCF_3$, and halogen;

as well as in form of their acid addition salts with pharmacologically acceptable acids.

Preferred compounds of formula (I) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $L_2$, Z, Q, and n as herein before or below defined, wherein A is selected from among —O—, and —NH—, preferably wherein A denotes —NH—, and wherein $L_1$ is a linker selected from a bond or a group selected from among —$C_1$-$C_2$-alkylene, and —$C_1$-$C_2$-alkenylene, and wherein $R_7$ is a ring selected from among —$C_3$-$C_8$-cycloalkyl, —$C_3$-$C_8$-heterocyclyl, —$C_5$-$C_{10}$-aryl, and —$C_5$-$C_{10}$-heteroaryl, and wherein the ring $R_7$ is optionally substituted with one or more groups selected from among —$CF_3$, —$C_1$-$C_6$-alkyl, —O—$CF_3$, —CN, —O—$C_1$-$C_6$-alkyl, —$C_4$-$C_6$-alkenyl, and —$C_1$-$C_6$-alkynyl, and -halogen, or wherein the ring $R_7$ is optionally substituted with one or more groups selected from among —$C_5$-$C_{10}$-aryl, —$C_5$-$C_{10}$-heteroaryl, —$C_3$-$C_8$-cycloalkyl, —$C_3$-$C_8$-heterocyclyl, optionally being substituted by one or more groups selected from among —OH, —$NH_2$, —$C_1$-$C_4$-alkyl, —O—$C_1$-$C_6$-alkyl, —CN, —$CF_3$, —$OCF_3$, halogen, and =O, or wherein the ring $R_7$ is optionally further bi-valently substituted on two neighbouring ring atoms, such that an annellated ring is formed by one or more groups selected from among —$C_1$-$C_6$-alkylene, —$C_2$-$C_6$-alkenylene and —$C_4$-$C_6$-alkynylene, in which one or two carbon centers may optionally be replaced by 1 or 2 hetero atoms selected from N, O and S, the bivalent group being optionally substituted by one or more groups selected from —OH, —$NH_2$, —$C_1$-$C_4$-alkyl, —O—$C_1$-$C_6$-alkyl, —CN, —$CF_3$, —$OCF_3$, halogen, and =O.

Preferred compounds of formula (I) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $L_2$, Z, Q, and n as herein before or below defined, wherein A is selected from among —O—, and —NH—, preferably wherein A denotes —NH—, and wherein $L_1$ is a linker selected from a bond or a group selected from among —$C_1$-$C_2$-alkylene, and —$C_1$-$C_2$-alkenylene, and wherein $R_7$ is a ring selected from among —$C_3$-$C_8$-cycloalkyl, —$C_3$-$C_8$-heterocyclyl, —$C_5$-$C_{10}$-aryl, and —$C_5$-$C_{10}$-heteroaryl, and wherein the ring $R_7$ is optionally substituted with one or more groups selected from among —$CF_3$, —CN, —$C_1$-$C_6$-alkenyl, and —$C_1$-$C_6$-alkynyl, and -halogen, or wherein the ring $R_7$ is optionally substituted with one or more groups selected from among —$C_5$-$C_{10}$-aryl, —$C_5$-$C_{10}$-heteroaryl, —$C_3$-$C_8$-cycloalkyl, —$C_3$-$C_8$-heterocyclyl, optionally being substituted by one or more groups selected from among —OH, —$NH_2$, —$C_1$-$C_4$-alkyl, —O—$C_1$-$C_6$-alkyl, —$CF_3$, —$OCF_3$, halogen, and =O.

Preferred compounds of formula (Ia) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{22}$, $R_{23}$, $L_2$, Z, Q, and n as herein before or below defined, wherein A' is selected from among -$L_1$-$R_7$, —HC=$L_1$-$R_7$, —$CH_2$-$L_1$-$R_7$, —S-$L_1$-$R_7$, —NH-$L_1$-$R_7$, and the structure (III)

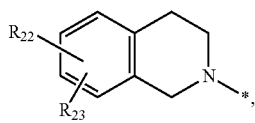

wherein $L_1$ is a linker selected from a bond or —$C_1$-$C_2$-alkylene, preferably wherein $L_1$ denotes methylene.

Preferred compounds of formula (Ia) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$ $R_{12}$, $R_{13}$, $R_{13'}$, $R_{14}$, $R_{15}$, $R_{15'}$ $R_{16}$, $R_{17}$, $R_{18}$, $R_{19}$, $R_{20}$, $R_{20'}$, $R_{22}$, $R_{23}$, $L_2$, Z, Q, and n as herein before or below defined,
wherein A' is selected from among -$L_1$-$R_7$, —HC=$L_1$-$R_7$, —CH$_2$-$L_1$-$R_7$, —S-$L_1$-$R_7$, —NH-$L_1$-$R_7$,
and the structure (III)

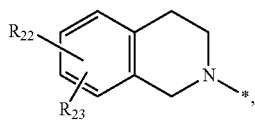

wherein $L_1$ denotes a bond.

Preferred compounds of formula (Ia) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$ $R_{12}$, $R_{13}$, $R_{13'}$, $R_{14}$, R is, $R_{15'}$ $R_{16}$, $R_{17}$, $R_{18}$, $R_{19}$, $R_{20}$, $R_{20'}$, $L_2$, Z, Q, and n as herein before or below defined,
wherein A' is selected from the structure (III)

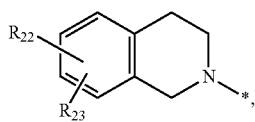

wherein $R_{22}$, and $R_{23}$ are being optionally and independently substituted by one or more groups selected from among —OH, —NH$_2$, —$C_1$-$C_4$-alkyl, —O—$C_1$-$C_6$-alkyl, —CN, —CF$_3$, —OCF$_3$, halogen, and =O.

Preferred compounds of formula (Ia) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$ $R_{12}$, $R_{13}$, $R_{13'}$, $R_{14}$, $R_{15}$, $R_{15'}$ $R_{16}$, $R_{17}$, $R_{18}$, $R_{19}$, $R_{20}$, $R_{20'}$, A', $L_2$, Z, Q, and n as herein before or below defined,
wherein $R_{22}$ is selected from among —H, —OH, —NH$_2$, —$C_1$-$C_4$-alkyl, —O—$C_1$-$C_6$-alkyl, —CN, —CF$_3$, —OCF$_3$, halogen, and =O;
and wherein $R_{23}$ is selected from among —H, —OH, —NH$_2$, —$C_1$-$C_4$-alkyl, —O—$C_1$-$C_6$-alkyl, —CN, —CF$_3$, —OCF$_3$, halogen, and =O.

Preferred compounds of formula (Ia) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$ $R_{12}$, $R_{13}$, $R_{13'}$, $R_{14}$, $R_{15}$, $R_{15'}$ $R_{16}$, $R_{17}$, $R_{18}$, $R_{19}$, $R_{20}$, $R_{20'}$, A', $L_2$, Z, Q, and n as herein before or below defined,
wherein $R_{22}$ is selected from among —H, —$C_1$-$C_4$-alkyl, —O—$C_1$-$C_6$-alkyl, —CF$_3$, —OCF$_3$, and halogen;
and wherein $R_{23}$ is selected from among —H, —$C_1$-$C_4$-alkyl, —O—$C_1$-$C_6$-alkyl, —CF$_3$, —OCF$_3$, and halogen.

Preferred compounds of formula (Ia) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$ $R_{12}$, $R_{13}$, $R_{13'}$, $R_{14}$, $R_{15}$, $R_{15'}$ $R_{16}$, $R_{17}$, $R_{18}$, $R_{19}$, $R_{20}$, $R_{20'}$, A', $L_2$, Z, Q, and n as herein before or below defined,
wherein $R_{22}$ is selected from among —H, —CF$_3$, —OCF$_3$, and halogen;
and wherein $R_{23}$ is selected from among —H, —CF$_3$, —OCF$_3$, and halogen.

Preferred compounds of formula (I) or (Ia) according to the invention are compounds with $R_1$, $R_2$, $R_3$, $R_4$, $R_5$, $R_6$, $R_7$, $R_8$, $R_{8'}$, $R_9$, $R_{9'}$, $R_{10}$, $R_{11}$, $R_{11'}$ $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{22}$, $R_{23}$, A, A', $L_2$, Z, Q, and n as herein before or below defined,
wherein $L_1$ is a linker selected from a bond or —$C_1$-$C_2$-alkylene, preferably wherein $L_1$ denotes methylene.

Preferred compounds of formula (I) or (Ia) according to the invention are compounds with $R_1$, $R_2$, $R_3$, $R_4$, $R_5$, $R_6$, $R_7$, $R_8$, $R_{8'}$, $R_9$, $R_{9'}$, $R_{10}$, $R_{11}$, $R_{11'}$ $R_{12}$, $R_{13}$, $R_{13'}$, $R_{14}$, $R_{15}$, $R_{15'}$ $R_{16}$, $R_{17}$, $R_{18}$, $R_{19}$, $R_{20}$, $R_{20'}$, $R_{22}$, $R_{23}$, A, A', $L_2$, Z, Q, and n as herein before or below defined,
wherein $L_1$ is a linker selected from a bond or —$C_1$-$C_2$-alkylene, preferably wherein $L_1$ denotes a bond.

Preferred compounds of formula (I) or (Ia) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$ $R_{12}$, $R_{13}$, $R_{13'}$, $R_{14}$, $R_{15}$, $R_{15'}$ $R_{16}$, $R_{17}$, $R_{18}$, $R_{19}$, $R_{20}$, $R_{20'}$, $R_{22}$, $R_{23}$, A, A', $L_1$, $L_2$, Z, Q, and n as herein before or below defined,
Wherein $R_7$ is a ring selected from among -$C_3$-$C_8$-cycloalkyl, and —$C_3$-$C_8$-heterocyclyl, —$C_5$-$C_{10}$-aryl,
wherein the ring $R_7$ is optionally substituted with one or more groups selected from —$C_1$-$C_6$-alkyl,
or wherein the ring $R_7$ is optionally substituted with one or more groups selected from —$C_5$-$C_{10}$-aryl, optionally being substituted by one or more groups selected from among —CF$_3$, —OCF$_3$, and halogen.

Preferred compounds of formula (I) or (Ia) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$ $R_{12}$, $R_{13}$, $R_{13'}$, $R_{14}$, $R_{15}$, $R_{15'}$ $R_{16}$, $R_{17}$, $R_{18}$, $R_{19}$, $R_{20}$, $R_{20'}$, $R_{22}$, $R_{23}$, A, A', $L_1$, $L_2$, Z, Q, and n as herein before or below defined,
wherein $R_7$ is a ring selected from among -$C_3$-$C_8$-cycloalkyl, and —$C_3$-$C_8$-heterocyclyl, —$C_5$-$C_{10}$-aryl,
wherein the ring $R_7$ is optionally substituted with one or more groups selected from —$C_1$-$C_6$-alkyl,
or wherein the ring $R_7$ is optionally substituted with one or more groups selected from —$C_5$-$C_{10}$-aryl, optionally being substituted by one or more groups selected from among $C_1$-$C_4$ alkyl, —OCF$_3$, and halogen.

Preferred compounds of formula (I) or (Ia) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$ $R_{12}$, $R_{13}$, $R_{13'}$, $R_{14}$, $R_{15}$, $R_{15'}$ $R_{16}$, $R_{17}$, $R_{18}$, $R_{19}$, $R_{20}$, $R_{20'}$, $R_{22}$, $R_{23}$, A, A', $L_1$, $L_2$, Z, Q, and n as herein before or below defined,
wherein $R_7$ is a ring selected from among -$C_3$-$C_8$-cycloalkyl, and —$C_3$-$C_8$-heterocyclyl, —$C_5$-$C_{10}$-aryl, wherein the ring $R_7$ is optionally substituted with one or more groups selected from —$C_1$-$C_6$-alkyl.

Preferred compounds of formula (I) or (Ia) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$ $R_{12}$, $R_{13}$, $R_{13'}$, $R_{14}$, $R_{15}$, $R_{15'}$ $R_{16}$, $R_{17}$, $R_{18}$, $R_{20}$, $R_{20'}$, $R_{22}$, $R_{23}$, A, A', $L_1$, $L_2$, Z, Q, and n as herein before or below defined, wherein $R_7$ denotes a group selected from among formula (II)

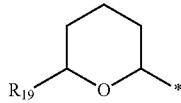
(II)

wherein $R_{19}$ denotes the ring —$C_5$-$C_{10}$-aryl, and wherein the ring $R_{19}$ is optionally substituted with one or more groups selected from —$C_1$-$C_6$-alkyl, preferably —$CH_3$.

Preferred compounds of formula (I) or (Ia) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{20}$, $R_{20'}$, $R_{22}$, $R_{23}$, A, A', $L_1$, $L_2$, Z, Q, and n as herein before or below defined,
wherein $R_7$ denotes a group selected from among formula (II)

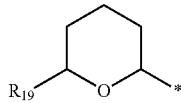
(II)

wherein $R_{19}$ denotes the ring —$C_5$-$C_{10}$-aryl, and wherein the ring $R_{19}$ is optionally substituted with one or more groups selected from among —$CF_3$, and —$OCF_3$.

Preferred compounds of formula (I) or (Ia) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{22}$, $R_{23}$, A, A', $L_1$, $L_2$, Z, Q, and n as herein before or below defined,
wherein $R_7$ is a ring selected from among —$C_3$-$C_8$-cycloalkyl, and —$C_5$-$C_{10}$-aryl, preferably wherein $R_7$ is a ring selected from among -hexyl, and -phenyl,
wherein the ring $R_7$ is optionally substituted with one or more groups selected from —$C_1$-$C_6$-alkyl,
or wherein the ring $R_7$ is optionally substituted with one or more groups selected from -phenyl, whereas such phenyl ring is optionally substituted by one or more groups selected from among —$C_1$-$C_4$-alkyl.

Preferred compounds of formula (I) or (Ia) according to the invention are compounds with $R_1$, $R_2$, $R_3$, $R_4$, $R_5$, $R_6$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{22}$, $R_{23}$, A, A', $L_1$, $L_2$, Z, Q, and n as herein before or below defined,
wherein $R_7$ is a ring selected from among —$C_3$-$C_8$-cycloalkyl, and —$C_5$-$C_{10}$-aryl, preferably wherein $R_7$ is a ring selected from among -hexyl, and -phenyl,
wherein the ring $R_7$ is optionally substituted with one or more groups selected from —$C_1$-$C_6$-alkyl,
or wherein the ring $R_7$ is optionally substituted with one or more groups selected from -phenyl, whereas such phenyl ring is optionally substituted by one or more groups selected from among —$CF_3$, -halogen, and —$OCF_3$, preferably from among —$CF_3$, and -halogen.

Preferred compounds of formula (I) or (Ia) according to the invention are compounds with $R_2$, $R_3$, $R_4$, $R_5$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{22}$, $R_{23}$, A, A', $L_1$, $L_2$, Z, Q, and n as herein before or below defined,
wherein $R_1$ is selected from among —H, —$OCH_3$, and —OH, preferably wherein $R_1$ denotes —H.

Preferred compounds of formula (I) or (Ia) according to the invention are compounds with $R_1$, $R_3$, $R_4$, $R_5$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{22}$, $R_{23}$, A, A', $L_1$, $L_2$, Z, Q, and n as herein before or below defined,
wherein $R_2$ is selected from among —H, —O—$C_1$-$C_4$-alkyl, and —$C_1$-$C_4$-alkyl, preferably wherein $R_2$ is selected from —$C_1$-$C_4$-alkyl.

Preferred compounds of formula (I) or (Ia) according to the invention are compounds with $R_1$, $R_2$, $R_4$, $R_5$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{22}$, $R_{23}$, A, A', $L_1$, $L_2$, Z, Q, and n as herein before or below defined,
wherein $R_3$ is selected from among —H, —$OCH_3$, and —OH, preferably wherein $R_3$ denotes —H.

Preferred compounds of formula (I) or (Ia) according to the invention are compounds with $R_1$, $R_2$, $R_3$, $R_4$, $R_5$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{22}$, $R_{23}$, A, A', $L_1$, $L_2$, Z, Q, and n as herein before or below defined,
wherein $R_6$ denotes —H.

Preferred compounds of formula (I) or (Ia) according to the invention are compounds with $R_1$, $R_2$, $R_3$, $R_4$, $R_5$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{22}$, $R_{23}$, A, A', $L_1$, $L_2$, Z, and Q as herein before or below defined,
wherein n is 2.

Preferred compounds of formula (I) or (Ia) according to the invention are compounds with $R_1$, $R_2$, $R_3$, $R_4$, $R_5$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{22}$, $R_{23}$, A, A', $L_1$, $L_2$, Q, and n as herein before or below defined,
wherein Z denotes C.

Preferred compounds of formula (I) or (Ia) according to the invention are compounds with $R_1$, $R_2$, $R_3$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{19}$, $R_{20}$, $R_{20'}$, $R_{22}$, $R_{23}$, A, A', $L_1$, Z, Q, and n as herein before or below defined,
wherein Z denotes C, and wherein $R_4$ denotes —H, and wherein $R_5$ denotes a group of the structure -$L_2$-$R_{18}$,
wherein $L_2$ is a group selected from among —NH—, and —N($CH_3$)—,
wherein $R_{18}$ is —$C_6$-heterocyclyl comprising 1 hetero atom selected from O,
wherein $R_{18}$ is optionally substituted by —O—$CH_3$;

Preferred compounds of formula (I) or (Ia) according to the invention are compounds with $R_1$, $R_2$, $R_3$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{19}$, $R_{20}$, $R_{20'}$, $R_{22}$, $R_{23}$, A, A', $L_1$, Z, Q, and n as herein before or below defined,
wherein Z denotes C, and wherein $R_4$ denotes —H, and wherein $R_5$ denotes a group of the structure -$L_2$-$R_{18}$,
wherein $L_2$ is a group selected from among —NH—, and —N($CH_3$)—,
wherein $R_{18}$ is —$C_6$-heterocyclyl comprising 1 hetero atom selected from O,
wherein $R_{18}$ is optionally substituted by -halogen, preferably —F.

Preferred compounds of formula (I) or (Ia) according to the invention are compounds with $R_1$, $R_2$, $R_3$, $R_4$, $R_5$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{22}$, $R_{23}$, A, A', $L_1$, Z, Q, and n as herein before or below defined,
wherein $L_2$ denotes —NH—.

Preferred compounds of formula (I) or (Ia) according to the invention are compounds with $R_1$, $R_2$, $R_3$, $R_6$, $R_7$, $R_8$, $R_{8'}$, $R_9$, $R_9$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{22}$, $R_{23}$, A, A', $L_1$, $L_2$, Z, and n as herein before or below defined,
wherein Z denotes C, and wherein $R_4$ denotes —H and $R_5$ denotes a group of the structure —N($R_{20}$,$R_{20'}$),
wherein $R_{20}$ and $R_{20'}$ together form a —$C_4$-$C_5$-alkylene group such that a ring is formed, wherein such ring is optionally substituted with one or more groups selected from —N($C_0$-$C_1$-alkyl)-$SO_2$—$CH_3$.

Preferred compounds of formula (I) or (Ia) according to the invention are compounds with $R_1$, $R_2$, $R_3$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{22}$, $R_{23}$, A, A', $L_1$, $L_2$, Z, and n as herein before or below defined,
wherein Z denotes C, and wherein $R_4$ denotes —H and $R_5$ denotes a group of the structure —N($R_{20}$,$R_{20'}$),
wherein $R_{20}$ and $R_{20'}$ together form a —$C_5$-alkylene group such that a ring is formed, wherein such ring is optionally substituted with one or more groups selected from —N($C_0$-$C_1$-alkyl)-$SO_2$—$CH_3$, preferably —NH—$SO_2$—$CH_3$.

Preferred compounds of formula (I) or (Ia) according to the invention are compounds with $R_1$, $R_2$, $R_3$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{19}$, $R_{22}$, $R_{23}$, A, A', $L_1$, and n as herein before or below defined, wherein Z denotes C, and wherein $R_4$ denotes —H, and wherein $R_5$ denotes a group of the structure -$L_2$-$R_{18}$,
wherein $L_2$ is a group selected from among —NH—, and —N($CH_3$)—,
wherein $R_{18}$ is —$C_6$-heterocyclyl comprising 1 hetero atom selected from O,
wherein $R_{18}$ is optionally substituted by —O—$CH_3$;
or wherein $R_4$ denotes —H and $R_5$ denotes a group of the structure —N($R_{20}$,$R_{20'}$),
wherein $R_{20}$ and $R_{20'}$ together form a —$C_4$-$C_5$-alkylene group such that a ring is formed, wherein such ring is optionally substituted with one or more groups selected from among —OH, and —N($C_0$-$C_1$-alkyl)-$SO_2$—$CH_3$.

Preferred compounds of formula (I) or (Ia) according to the invention are compounds with $R_1$, $R_2$, $R_3$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{19}$, $R_{22}$, $R_{23}$, A, A', $L_1$, and n as herein before or below defined, wherein Z denotes C, and wherein $R_4$ denotes —H, and wherein $R_5$ denotes a group of the structure -$L_2$-$R_{18}$,
wherein $L_2$ is a group selected from among —NH—, and —N($CH_3$)—,
wherein $R_{18}$ is —$C_6$-heterocyclyl comprising 1 hetero atom selected from O,
wherein $R_{18}$ is optionally substituted by —F;
or wherein $R_4$ denotes —H and $R_5$ denotes a group of the structure —N($R_{20}$,$R_{20'}$),
wherein $R_{20}$ and $R_{20'}$ together form a —$C_4$-$C_5$-alkylene group such that a ring is formed,
wherein such ring is optionally substituted with one or more groups selected from among —OH, and —N($C_0$-$C_1$-alkyl)-$SO_2$—$CH_3$.

Preferred compounds of formula (I) or (Ia) according to the invention are compounds with $R_1$, $R_2$, $R_3$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{22}$, $R_{23}$, A, A', $L_1$, $L_2$, and n as herein before or below defined,
wherein Z denotes C, and wherein $R_4$ denotes —H, and wherein $R_5$ denotes a group of the structure —N($R_{21}$,$R_{21'}$),
wherein $R_{21}$ and $R_{21'}$ together form a —$C_5$-alkylene group such that a ring is formed, in which one carbon center of the —$C_5$-alkylene group is replaced by one hetero atom selected from O.

Preferred compounds of formula (I) or (Ia) according to the invention are compounds with $R_1$, $R_2$, $R_3$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{22}$, $R_{23}$, A, A', $L_1$, $L_2$, and n as herein before or below defined,
wherein Z denotes C, and wherein $R_4$ denotes —H, and wherein $R_5$ denotes a group of the structure —N($R_{21}$,$R_{21'}$),
wherein $R_{21}$ and $R_{21'}$ together form a —$C_5$-alkylene group such that a ring is formed, in which one carbon center of the —$C_5$-alkylene group is replaced by one hetero atom selected from O, and wherein such ring is optionally substituted with one or more groups selected from —N($C_0$-$C_1$-alkyl)-$SO_2$—$CH_3$, —O—$CH_3$, and —F.

Preferred compounds of formula (I) or (Ia) according to the invention are compounds with $R_1$, $R_2$, $R_3$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{19}$, $R_{22}$, $R_{23}$, A, A', $L_1$, and n as herein before or below defined,
wherein Z denotes C, and wherein $R_4$ denotes —H, and wherein $R_5$ denotes a group of the structure -$L_2$-$R_{18}$,
wherein $L_2$ is a group selected from among —NH—, and —N($CH_3$)—,
wherein $R_{18}$ is —$C_6$-heterocyclyl comprising 1 hetero atom selected from O,
wherein $R_{18}$ is optionally substituted by —O—$CH_3$;
or wherein $R_4$ denotes —H and $R_5$ denotes a group of the structure —N($R_{20}$,$R_{20'}$),
wherein $R_{20}$ and $R_{20'}$ together form a —$C_4$-$C_5$-alkylene group such that a ring is formed,
wherein such ring is optionally substituted with one or more groups selected from —N($C_0$-$C_1$-alkyl)-$SO_2$—$CH_3$.

Preferred compounds of formula (I) or (Ia) according to the invention are compounds with $R_1$, $R_2$, $R_3$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{19}$, $R_{22}$, $R_{23}$, A, A', $L_1$, and n as herein before or below defined, wherein
Z denotes C, and
wherein $R_4$ denotes —H, and wherein $R_5$ denotes a group of the structure -$L_2$-$R_{18}$,
wherein $L_2$ is a group selected from among —NH—,
wherein $R_{18}$ is —$C_6$-heterocyclyl comprising 1 hetero atom selected from O,
wherein $R_{18}$ is optionally substituted by —O—$CH_3$.

Preferred compounds of formula (I) or (Ia) according to the invention are compounds with $R_1$, $R_2$, $R_3$, $R_6$, $R_7$, $R_8$, $R_{8'}$, $R_9$, $R_{9'}$, $R_{10}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{19}$, $R_{22}$, $R_{23}$, A, A', $L_1$, and n as herein before or below defined, wherein
Z denotes C, and
wherein $R_4$ denotes —H, and wherein $R_5$ denotes a group of the structure -$L_2$-$R_{18}$,
wherein $L_2$ is a group selected from among —NH—,
wherein $R_{18}$ is —$C_6$-heterocyclyl comprising 1 hetero atom selected from O,
wherein $R_{18}$ is optionally substituted by —F.

All of the above embodiments under formula (I) or (Ia) have to be understood to optionally be present in form of their individual optical isomers, mixtures of their individual optical isomers, or racemates, as well as in form of their acid addition salts with pharmacologically acceptable acids, as well as in form of their solvates and/or hydrates.

It has now been found that such compounds as herein before or below defined could be used as a medicament.

It has been found that such compounds as herein before or below defined could be used for making a medicament for the treatment of inflammatory diseases. It has been found that such compounds as herein before or below defined could be used for making a medicament for the treatment of inflammatory diseases, wherein the inflammatory diseases are selected from inflammatory diseases of the respiratory tract. It has been found that such compounds as herein before or below defined could be used for making a medicament for the treatment of inflammatory diseases, wherein the inflammatory diseases are selected from chronic obstructive pulmonary disease, asthma, and cystic fibrosis. It has been found that such compounds as herein before or below defined could be used for making a medicament for the treatment of neurologic diseases, preferably for the treatment of pain diseases especially for the treatment of inflammatory and neuropathic pain disease, especially for the treatment of chronic pain. It has been found that such compounds as herein before or below defined could be used for making a medicament for the treatment of immune related diseases, preferably for the treatment of diabetes mellitus. It has been found that such compounds as herein before or below defined could be used for making a medicament for the treatment of cardiovascular diseases, preferably for the treatment of peripheral atherosclerotic disease. It has been found that such compounds as herein before or below defined could be used for making a medicament for the treatment of diabetic nephropathy.

Present invention encloses compounds as herein before or below defined as medicaments. Present invention encloses compounds as herein before or below defined as medicaments for the treatment of inflammatory diseases. Present invention encloses compounds as herein before or below defined as medicaments for the treatment of inflammatory diseases, wherein the inflammatory diseases are selected from inflammatory diseases of the respiratory tract. Present invention encloses compounds as herein before or below defined as medicaments for the treatment of inflammatory diseases, wherein the inflammatory diseases are selected from chronic obstructive pulmonary disease, asthma, and cystic fibrosis. Present invention encloses compounds as herein before or below defined as medicaments for the treatment of neurologic diseases, preferably for the treatment of pain diseases especially for the treatment of inflammatory and neuropathic pain disease, especially for the treatment of chronic pain. Present invention encloses compounds as herein before or below defined as medicaments for the treatment of immune related diseases, preferably for the treatment of diabetes mellitus. Present invention encloses compounds as herein before or below defined as medicaments for the treatment of cardiovascular diseases, preferably for the treatment of peripheral atherosclerotic disease. Present invention encloses compounds as herein before or below defined as medicaments for the treatment of diabetic nephropathy.

It has been found that such compounds as herein before or below defined could be used for the treatment of inflammatory diseases. It has been found that such compounds as herein before or below defined could be used for the treatment of inflammatory diseases, wherein the inflammatory diseases are selected from inflammatory diseases of the respiratory tract. It has been found that such compounds as herein before or below defined could be used for the treatment of inflammatory diseases, wherein the inflammatory diseases are selected from chronic obstructive pulmonary disease, asthma, and cystic fibrosis. It has been found that such compounds as herein before or below defined could be used for the treatment of neurologic diseases, preferably for the treatment of pain diseases especially for the treatment of inflammatory and neuropathic pain disease, especially for the treatment of chronic pain. It has been found that such compounds as herein before or below defined could be used for the treatment of immune related diseases, preferably for the treatment of diabetes mellitus. It has been found that such compounds as herein before or below defined could be used for the treatment of cardiovascular diseases, preferably for the treatment of peripheral atherosclerotic disease. It has been found that such compounds as herein before or below defined could be used for the treatment of diabetic nephropathy.

DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, —$C_1$-$C_6$-alkyl means an alkyl group or radical having 1 to 6 carbon atoms. In general, for groups comprising two or more subgroups, the last named subgroup is the radical attachment point, for example, the substituent "aryl-$C_1$-$C_3$-alkyl-" means an aryl group which is bound to a $C_1$-$C_3$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

For example, the term "3-carboxypropyl-group" represents the following substituent:

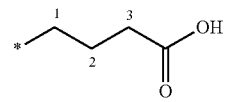

wherein the carboxy group is attached to the third carbon atom of the propyl group. The terms "1-methylpropyl-", "2,2-dimethylpropyl-" or "cyclopropylmethyl-" group represent the following groups:

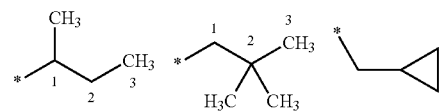

The asterisk may be used in sub-formulas to indicate the bond which is connected to the core molecule as defined.

Many of the follwings terms may be used repeatedly in the definition of a formula or group and in each case have one of the meanings given above, independently of one another.

Unless otherwise stated, all the substituents are independent of one another. If for example there might be a plurality of $C_1$-$C_6$-alkyl groups as substituents in one group, in the case of three substituents $C_1$-$C_6$-alkyl, one may represent methyl, one n-propyl and one tert-butyl.

Within the scope of this application, in the definition of possible substituents, these may also be represented in the form of a structural formula. An asterisk (*) in the structural formula of the substituent is to be understood as being the linking point to the rest of the molecule. Moreover, the atom of the substituent which follows the linking point is referred to as the atom in position number 1. Thus, for example, the groups N-piperidinyl (Piperidin-A), 4-piperidinyl (Piperidin-B), 2-tolyl (Tolyl-C), 3-tolyl (Tolyl-D), and 4-tolyl (Tolyl-E) are shown as follows:

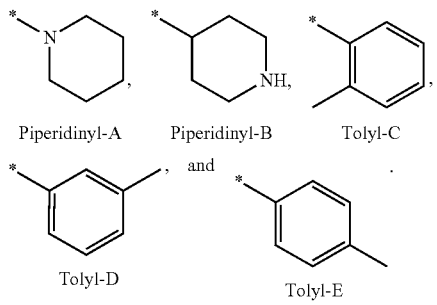

If there is no asterisk (*) in the structural formula of the substituent, each hydrogen atom may be removed from the substituent and the valency thus freed may act as a binding site to the rest of a molecule. Thus, for example, (Tolyl-F) may represent 2-tolyl, 3-tolyl, 4-tolyl, and benzyl

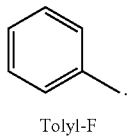

Tolyl-F

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

- Straight-chain or branched carbon chains, optionally interrupted by heteroatoms, optionally substituted by rings, heteroatoms or other common functional groups.
- Aromatic or non-aromatic ring systems consisting of carbon atoms and optionally heteroatoms, which may in turn be substituted by functional groups.
- A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

By the term "branched or unbranched, saturated or unsaturated $C_1$-$C_6$-carbon chain" it is meant a chain of carbon atoms, which is constituted by 1 to 6 carbon atoms arranged in a row and which can optionally further comprise branches or one or more hetero atoms selected from N, O or S. Said carbon chain can be saturated or unsaturated by comprising double or triple bonds.

If the carbon chain is to be substituted by a group which together with one or two carbon atoms of an alkylene chain forms a carbocyclic ring with 3, 5 or 6 carbon atoms, this includes the following examples of the rims:

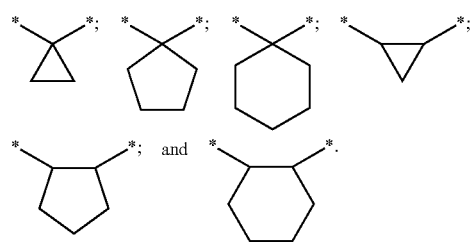

The term "$C_1$-$C_n$-alkyl", wherein n is an integer from 2 to n, either alone or in combination with another radical denotes an acyclic, saturated, branched or linear hydrocarbon radical with 1 to n C atoms. For example the term $C_1$-$C_5$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

By the term "$C_1$-$C_6$-alkyl" (including those which are part of other groups) are meant branched and unbranched alkyl groups with 1 to 6 carbon atoms and by the term "$C_1$-$C_4$-alkyl" are meant branched and unbranched alkyl groups with 1 to 4 carbon atoms. Alkyl groups with 1 to 4 carbon atoms are preferred. By the term "$C_1$-$C_3$-alkyl" are meant branched and unbranched alkyl groups with 1 to 3 carbon atoms and by the term "$C_2$-$C_4$-alkyl" are meant branched and unbranched alkyl groups with 2 to 4 carbon atoms. Examples for alkyl groups with 1-6 carbon atoms include: methyl, ethyl, n-propyl, iso-propyl, n-butyl, iso-butyl, sec-butyl, tert-butyl, n-pentyl, iso-pentyl, neo-pentyl or hexyl. Optionally the abbreviations Me, Et, n-Pr, i-Pr, n-Bu, i-Bu, t-Bu, etc. may also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

The term "$C_1$-$C_n$-alkylene" wherein n is an integer 2 to n, either alone or in combination with another radical, denotes an acyclic, straight or branched chain divalent alkyl radical containing from 1 to n carbon atoms. For example the term $C_1$-$C_4$-alkylene includes —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —$CH_2$—$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$— and —$C(CH_3)(CH_2CH_3)$—.

By the term "$C_1$-$C_8$-alkylene" (including those which are part of other groups) are meant branched and unbranched alkylene groups with 1 to 8 carbon atoms. By the term "$C_2$-$C_8$-alkylene" are meant branched and unbranched alkylene groups with 2 to 8 carbon atoms. By the term "$C_2$-$C_6$-alkylene" are meant branched and unbranched alkylene groups with 2 to 6 carbon atoms. By the term "$C_1$-$C_4$-alkylene" are meant branched and unbranched alkylene groups with 1 to 4 carbon atoms. By the term "$C_1$-$C_2$-alkylene" are meant branched and unbranched alkylene groups with 1 to 2 carbon atoms. By the term "$C_0$-$C_4$-alkylene" are meant branched and unbranched alkylene groups with 0 to 4 carbon atoms, thus also a single bond is encompassed. By the term "$C_1$-$C_3$-alkylene" are meant branched and unbranched alkylene groups with 1 to 3 carbon atoms. Examples for $C_1$-$C_8$-alkylene include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene, heptylene or octylene. Unless stated otherwise, the definitions propylene, butylene, pentylene, hexylene, heptylene and octylene include all the possible isomeric forms of the groups in question with the same number of carbons. Thus, for example, propyl also includes 1-methylethylene and butylene includes 1-methylpropylene, 1,1-dimethylethylene, 1,2-dimethylethylene.

A —$C_1$-alkylene group, which is linked to a structure on two neighbouring ring atoms such that an annellated ring is formed, results to a $C_3$-carbocycle. A —$C_2$-alkylene group, which is linked to a structure on two neighbouring ring atoms such that an annellated ring is formed, results to a $C_4$-carbocycle. A —$C_3$-alkylene group, which is linked to a structure on two neighbouring ring atoms such that an annellated ring is formed, results to a $C_5$-carbocycle. A —$C_4$-alkylene group, which is linked to a structure on two neighbouring ring atoms such that an annellated ring is formed, results to a $C_6$-carbocycle. A —$C_5$-alkylene group, which is linked to a structure on two neighbouring ring atoms such that an annellated ring is formed, results to a $C_7$-carbocycle. A —$C_6$-alkylene group, which is linked to a structure on two neighbouring ring atoms such that an annellated ring is formed, results to a $C_8$-carbocycle.

In the definition of possible substituents, which are linked to such $C_1$-$C_6$-alkylene groups forming a $C_3$-$C_8$-carbocycle, it is to be understood that any of the atoms of the resulting $C_3$-$C_8$-carbocycles could be the linking point for such a substituent.

If the carbon chain is to be substituted by a group which together with one or two carbon atoms of the alkylene chain forms a carbocyclic ring with 3, 5 or 6 carbon atoms, this includes the following examples of the rings:

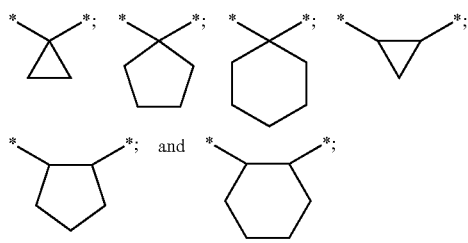

The term "$C_2$-$C_n$-alkenyl", is used for a group as defined in the definition for "$C_1$-$C_n$-alkyl" with at least two carbon atoms, if at least two of those carbon atoms of said group are bonded to each other by a double bond.

By the term "$C_2$-$C_6$-alkenyl" (including those which are part of other groups) are meant branched and unbranched alkenyl groups with 2 to 6 carbon atoms and by the term "$C_2$-$C_4$-alkenyl" are meant branched and unbranched alkenyl groups with 2 to 4 carbon atoms, provided that they have at least one double bond. Alkenyl groups with 2 to 4 carbon atoms are preferred. Examples for $C_2$-$C_6$-alkenyls include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-prop enyl, 1-methyl-2-propenyl etc.

By the term "methenylene" is meant a group with 1 carbon atom, provided that it is linked by a single bond as well as on the other side by a double bond. The asterisks ('p) in the structural formula is to be understood as being the linking points to the rest of the molecule, whereas the valency of the rest of the molecule be freed thus a single and a double bond can be formed by replacement of further hydrogens at the binding site if applicable:

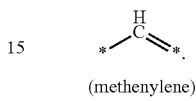

(methenylene)

The term "$C_2$-$C_n$-alkenylene" is used for a group as defined in the definition for "$C_1$-$C_n$-alkylene" with at least two carbon atoms, if at least two of those carbon atoms of said group are bonded to each other by a double bond.

By the term "$C_2$-$C_8$-alkenylene" (including those which are part of other groups) are meant branched and unbranched alkenylene groups with 2 to 8 carbon atoms and by the term "$C_2$-$C_6$-alkenylene" are meant branched and unbranched alkenylene groups with 2 to 6 carbon atoms. By the term "$C_1$-$C_2$-alkenylene" are meant alkenylene groups with 1 to 2 carbon atoms, provided that they have at least one double bond, whereas by the term "$C_1$-alkenylene" is meant "methenylene". Examples for $C_2$-$C_8$-alkenylenes include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene, heptenylene or octenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene.

A —$C_3$-alkenylene group, which is linked to a structure on two neighbouring ring atoms such that an annellated ring is formed, results to a $C_5$-carbocycle. A —$C_4$-alkenylene group, which is linked to a structure on two neighbouring ring atoms such that an annellated ring is formed, results to a $C_6$-carbocycle. A —$C_5$-alkenylene group, which is linked to a structure on two neighbouring ring atoms such that an annellated ring is formed, results to a $C_7$-carbocycle. A $C_6$-alkenylene group, which is linked to a structure on two neighbouring ring atoms such that an annellated ring is formed, results to a $C_8$-carbocycle.

In the definition of possible substituents, which are linked to such $C_3$-$C_6$-alkenylene groups forming a $C_5$-$C_8$-carbocycle, it is to be understood that any of the atoms of the resulting $C_5$-$C_1$-carbocycles could be the linking point for such a substituent.

The term "$C_2$-$C_n$-alkynyl", is used for a group as defined in the definition for "$C_1$-$C_n$-alkyl" with at least two carbon atoms, if at least two of those carbon atoms of said group are bonded to each other by a triple bond.

By the term "$C_2$-$C_6$-alkynyl" (including those which are part of other groups) are meant branched and unbranched alkynyl groups with 2 to 6 carbon atoms and by the term "$C_2$-$C_4$-alkynyl" are meant branched and unbranched alkynyl groups with 2 to 4 carbon atoms, provided that they have at least one triple bond. Examples for $C_2$-$C_6$-alkynyls include: ethynyl, propynyl, butynyl, pentynyl or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1-, 2-, and 3-butynyl, 1-methyl-1-propynyl, 1-methyl-2-propynyl etc.

The term "$C_2$-$C_n$-alkynylene" is used for a group as defined in the definition for "$C_1$-$C_n$-alkylene" with at least two carbon atoms, if at least two of those carbon atoms of said group are bonded to each other by a triple bond.

By the term "$C_2$-$C_8$-alkynylene" (including those which are part of other groups) are meant branched and unbranched alkynylene groups with 2 to 8 carbon atoms and by the term "$C_2$-$C_6$-alkynylene" are meant branched and unbranched alkynylene groups with 2 to 6 carbon atoms. Examples of $C_2$-$C_8$-alkynylenes include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene, heptynylene or octynylene. Unless stated otherwise, the definitions propynylene, butynylene, pentynylene and hexynylene include all the possible isomeric forms of the groups in question with the same number of carbons. Thus for example propynyl also includes 1-methylethynylene and butynylene includes 1-methylpropynylene, 1,1-dimethylethynylene, 1,2-dimethylethynylene.

The term "carbocyclyl" as used either alone or in combination with another radical, means a mono- bi- or tricyclic ring structure consisting of 3 to 14 carbon atoms. The term "carbocycle" refers to fully saturated and aromatic ring systems and partially saturated ring systems. The term "carbocycle" encompasses fused, bridged and spirocyclic systems:

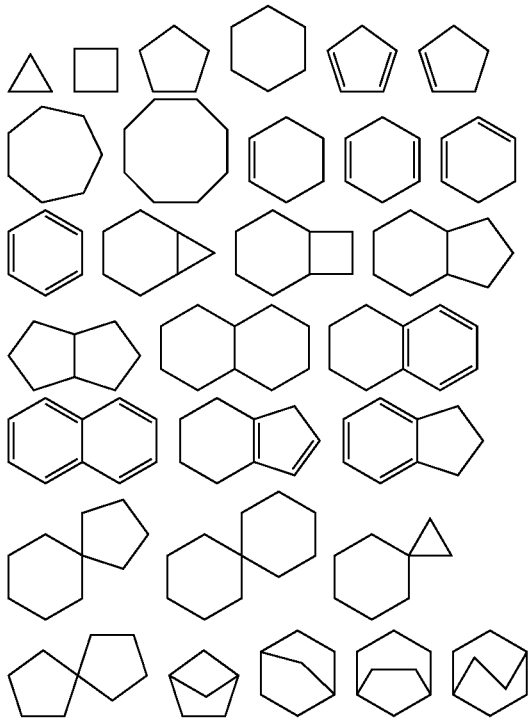

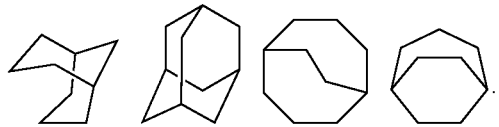

By the term "ring" are meant carbocycles, which can be saturated, unsaturated or aromatic and which optionally can comprise one or more hetero atoms selected from N, O or S.

The term "heterocyclyl" means a saturated or unsaturated mono- or polycyclic-ring systems including aromatic ring system containing one or more heteroatoms selected from N, O or $S(O)_r$, wherein r=0, 1 or 2, consisting of 3 to 14 ring atoms wherein none of the heteroatoms is part of the aromatic ring. The term "heterocycle" is intended to include all the possible isomeric forms.

Thus, the term "heterocyclyl" includes the following exemplary structures which are not depicted as radicals as each form may be attached through a covalent bond to any atom so lone as annronriate valences are maintained:

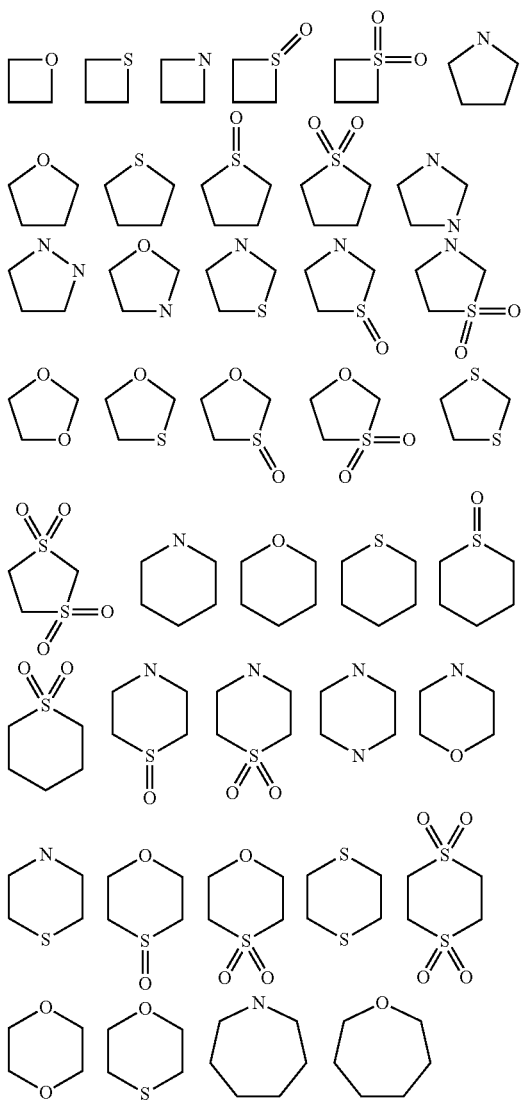

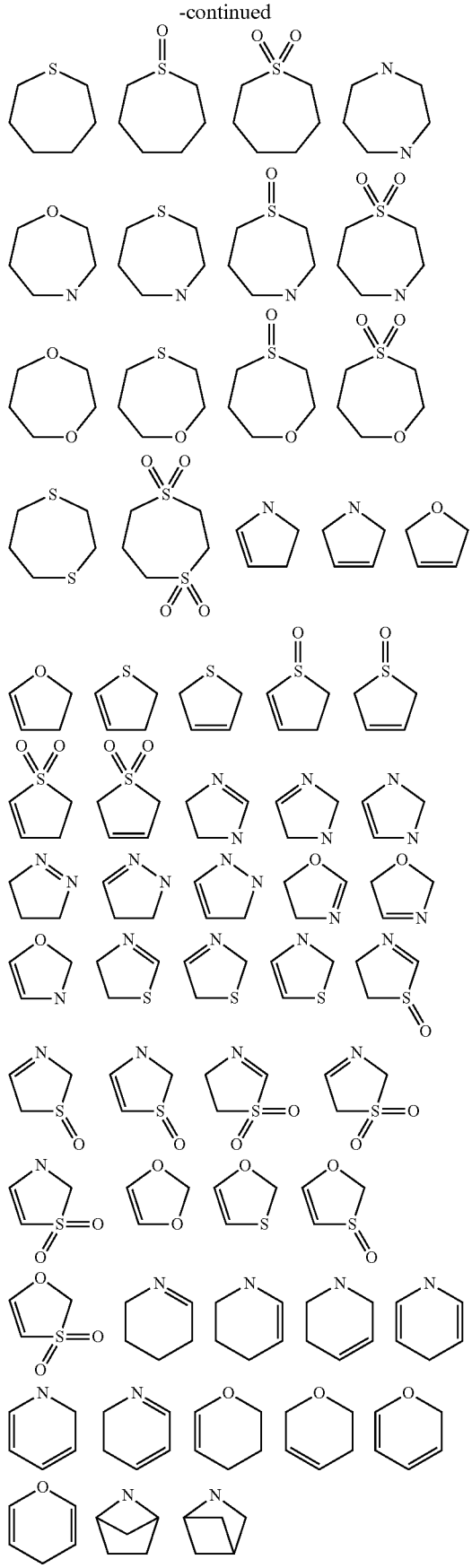
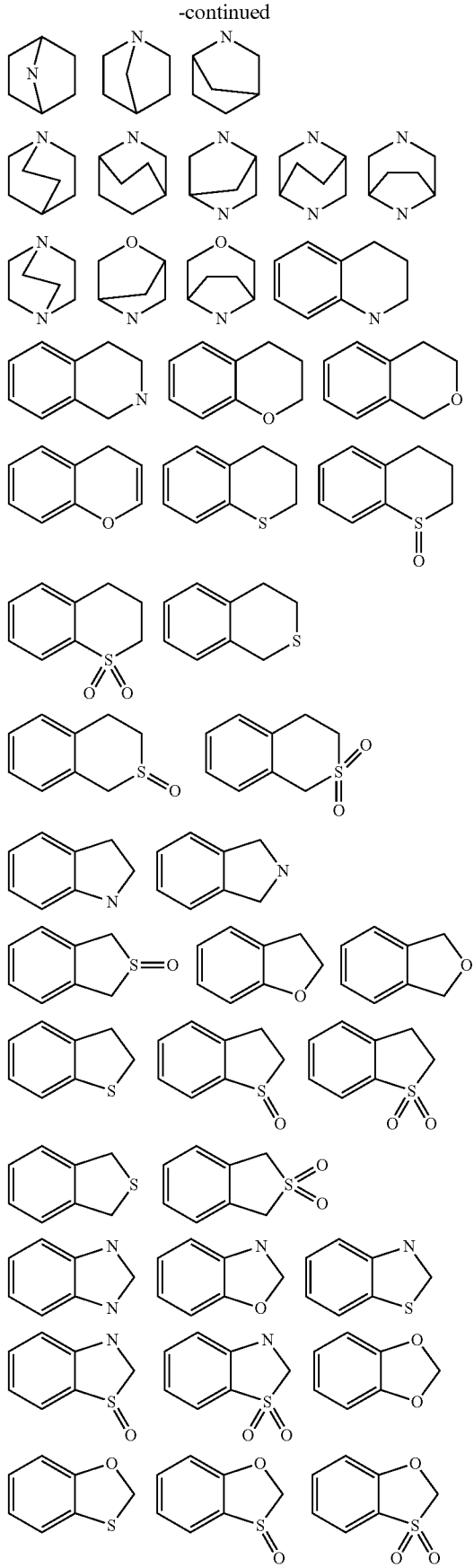

Examples for $C_6$-heterocyclyl include:

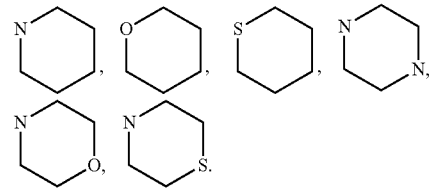

Examples for $C_7$-heterocyclyl include:

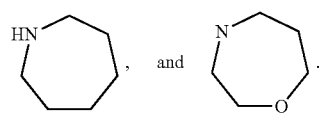

Unless otherwise mentioned, a heterocyclic ring (or "heterocycle") may be provided with a keto group. Examples include:

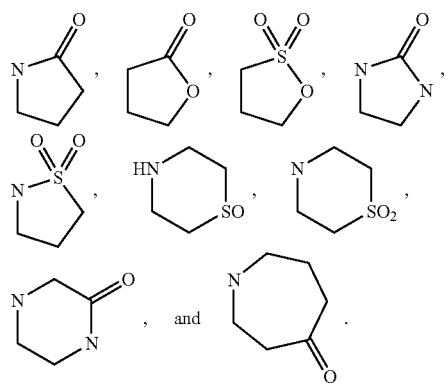

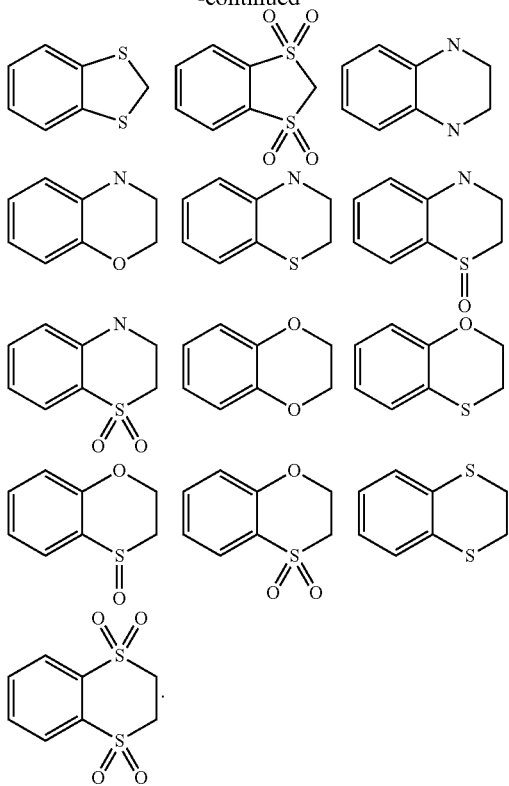

By the term "—$C_3$-$C_8$-heterocyclyl" are meant three-, four-, five-, six-, seven-, or eight-membered, saturated or unsaturated heterocyclic rings in which one or two or three carbon centers may optionally by replaced by 1 or 2 or 3 hetero atoms selected from N, O and S, while the ring may be linked to the molecule through a carbon atom or through a nitrogen atom, if there is one. By the term "—$C_5$-$C_8$-heterocyclyl" are meant five-, six-, seven-, or eight-membered, saturated or unsaturated heterocyclic rings in which one or two or three carbon centers may optionally by replaced by 1 or 2 or 3 hetero atoms selected from N, O and, while the ring may be linked to the molecule through a carbon atom or through a nitrogen atom, if there is one.

By the term "—$C_6$-heterocyclyl" are meant a six-membered, saturated or unsaturated heterocyclic ring in which one or two or three carbon centers (preferably one carbon center) may optionally by replaced by 1 or 2 or 3 hetero atoms (preferably 1 hetero atom) selected from N, O and S, while the ring may be linked to the molecule through a carbon atom or through a nitrogen atom, if there is one.

By the term "—$C_5$-heterocyclyl" are meant five-membered, saturated or unsaturated heterocyclic rings which may contain one, two, or three heteroatoms, selected from among oxygen, sulfur, and nitrogen, while the ring may be linked to the molecule through a carbon atom or through a nitrogen atom, if there is one.

Examples for $C_5$-heterocyclyl include:

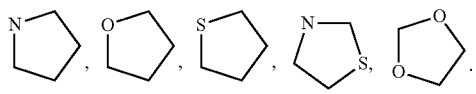

The term "$C_3$-$C_n$-cycloalkyl", wherein n is an integer from 3 to n, either alone or in combination with another radical denotes a cyclic, saturated, unbranched hydrocarbon radical with 3 to n C atoms. For example the term $C_3$-$C_7$-cycloalkyl includes cyclopropyl, cyclobutyl, cyclopentyl, cyclohexyl and cycloheptyl.

By the term "$C_3$-$C_8$-cycloalkyl" (including those which are part of other groups) are meant cyclic alkyl groups with 3 to 8 carbon atoms. Likewise, by the term "$C_3$-$C_6$-cycloalkyl" are meant cyclic alkyl groups with 3 to 6 carbon atoms. Examples of $C_3$-$C_8$-cycloalkyls include: cyclopropyl, cyclobutyl, cyclopentyl, cyclohexyl, cycloheptyl or cyclooctyl. Unless otherwise stated, the cyclic alkyl groups may be substituted by one or more groups selected from among methyl, ethyl, isopropyl, tert-butyl, hydroxy, fluorine, chlorine, bromine, and iodine.

The term "$C_3$-$C_n$-cycloalkenyl", wherein n is an integer from 3 to n, either alone or in combination with another radical, denotes an cyclic, unsaturated but nonaromatic, unbranched hydrocarbon radical with 3 to n C atoms, at least two of which are bonded to each other by a double bond. For example the term $C_3$-$C_7$-cycloalkenyl includes cyclopropenyl, cyclobutenyl, cyclopentenyl, cyclopentadienyl, cyclohexenyl, cyclohexadienyl, cycloheptenyl cycloheptadienyl and cycloheptatrienyl.

By the term "aryl" (including those which are part of other groups) are meant aromatic ring systems. By the term "$C_5$-$C_{10}$-aryl" (including those which are part of other groups) are meant aromatic ring systems with 5 to 10 carbon atoms. Preferred are "$C_6$-$C_{10}$-aryl" groups whereas aromatic rings are meant with 6 to 10 carbon atoms. Examples include: phenyl or naphthyl. Also preferred are "$C_5$-$C_6$-aryl" groups whereas aromatic rings are meant with 5 to 6 carbon atoms Unless otherwise stated, the aromatic ring systems may be substituted by one or more groups selected from among methyl, ethyl, iso-propyl, tert-butyl, hydroxy, fluorine, chlorine, bromine and iodine.

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

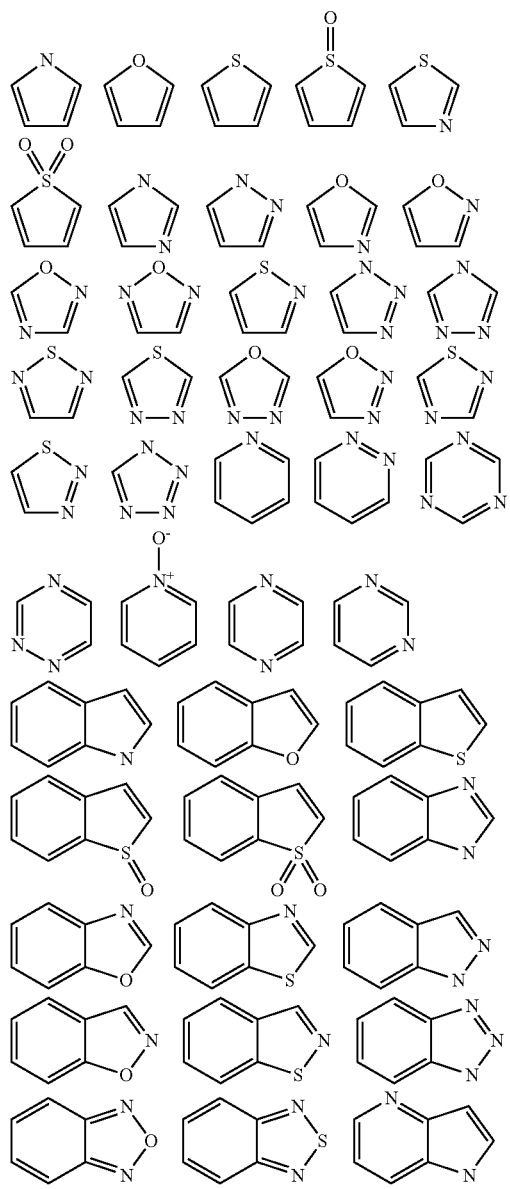

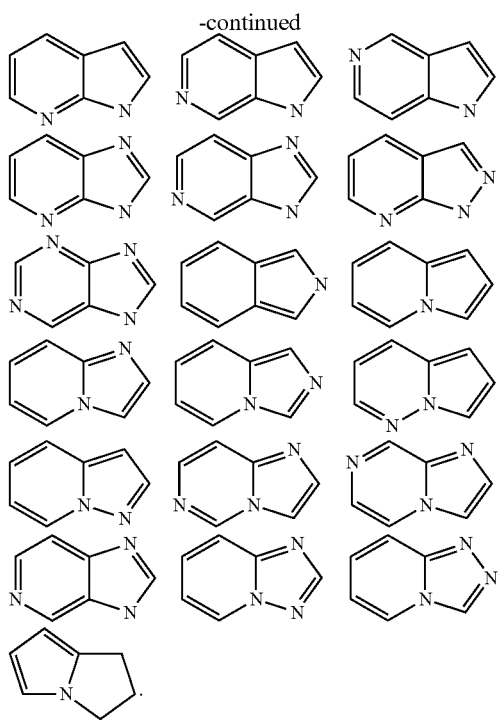

By the term "$C_5$-$C_{10}$-heteroaryl" (including those which are part of other groups) are meant five- or six-membered heterocyclic aromatic groups or 5-10-membered, bicyclic heteroaryl rings in which one or two or three carbon centers may optionally by replaced by 1 or 2 or 3 hetero atoms selected from N, O and S, and contain so many conjugated double bonds that an aromatic system is formed. The following are examples of five- or six- or nine-membered heterocyclic aromatic groups:

Preferred are "$C_5$-$C_6$-heteroaryl" groups whereas aromatic rings are meant five- or six-membered heterocyclic aromatic groups in which one or two or three carbon centers may optionally by replaced by 1 or 2 or 3 hetero atoms selected from N, O and S. Unless otherwise stated, these heteroaryls may be substituted by one or more groups selected from among methyl, ethyl, isopropyl, tert-butyl, hydroxy, fluorine, chlorine, bromine, and iodine.

When a generic combined groups are used, for example —Y—$C_1$-$C_4$-alkyl- with Y being a functional group such as —CO—, —NH—, —C(OH)— and the like, the functional group Y can be located at either of the ends of the —$C_1$-$C_4$-alkyl chain.

By the term "spiro-$C_3$-$C_8$-cycloalkyl" (spiro) are meant 3-8 membered, spirocyclic rings while the ring is linked to the molecule through a carbon atom, and whereas the resulting 3-8 membered carbocycle is formed by alkylene groups with 2 to 7 carbon atoms. By the term "spiro-$C_5$-cycloalkyl" (spiro) are meant 5 membered, spirocyclic rings while the ring is linked to the molecule through a carbon atom, whereas the resulting 5 membered carbocycle is formed by an alkylene group with 4 carbon atoms. By the term "spiro-$C_3$-$C_8$-cycloalkenyl" (spiro) are meant 3-8 membered, spirocyclic rings while the ring is linked to the molecule through a carbon atom, whereas the resulting 3-8 membered carbocycle is formed by alkenylene groups with 2 to 7 carbon atoms. By the term "spiro-$C_5$-cycloalkenyl" (spiro) are meant 5 membered, spirocyclic rings while the ring is linked to the molecule through a carbon atom, whereas the resulting 5 membered carbocycle is formed by alkenylene groups with 4 carbon atoms.

By the term "spiro-$C_3$-$C_8$-heterocyclyl" (spiro) are meant 3-8 membered, saturated or unsaturated, spirocyclic rings in which one or two or three carbon centers may optionally by replaced by 1 or 2 or 3 hetero atoms selected from N, O and S, while the ring may be linked to the molecule through a carbon atom or through a nitrogen atom, if there is one. By the term "spiro-$C_5$-heterocyclyl" (spiro) are meant 5 membered, saturated or unsaturated, spirocyclic rings which may contain one, two, or three heteroatoms selected from among oxygen, sulfur, and nitrogen, while the ring may be linked to the molecule through a carbon atom or through a nitrogen atom, if there is one.

Unless otherwise mentioned, a spirocyclic ring may be provided with an oxo, methyl, or ethyl group. Examples include:

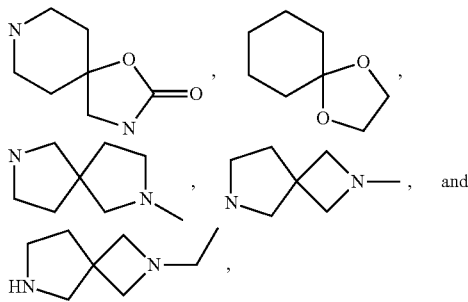

"Halogen" within the scope of the present invention denotes fluorine, chlorine, bromine or iodine. Unless stated to the contrary, fluorine, chlorine and bromine are regarded as preferred halogens.

"Linker" within the scope of the present invention denominates a bivalent group or a bond.

The above listed groups and residues can be combined to form more complex structures composed from carbon chains and rings or the like.

Compounds of general formula (I) or (Ia) may have acid groups, chiefly carboxyl groups, and/or basic groups such as e.g. amino functions. Compounds of general formula (I) or (Ia) may therefore occur as internal salts, as salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically useable bases such as alkali or alklaline earth metal hydroxides or carbonates, zinc or ammonium hydroxides or organic amines such as e.g. diethylamine, triethylamine, triethanolamine inter alia.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like.

(also see Pharmaceutical salts, Berge, S. M. et al., J. Pharm. Sci., (1977), 66, 1-19). The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

As mentioned hereinbefore, the compounds of formula (I) or (Ia) may be converted into the salts thereof, particularly for pharmaceutical use, into the physiologically and pharmacologically acceptable salts thereof. These salts may on the one hand be in the form of the physiologically and pharmacologically acceptable acid addition salts of the compounds of formula (I) or (Ia) with inorganic or organic acids. On the other hand, if R is hydrogen, the compound of formula (I) or (Ia) may also be converted by reaction with inorganic bases into physiologically and pharmacologically acceptable salts with alkali or alkaline earth metal cations as counter ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. The alkali and alkaline earth metal salts of the compound of formula (I) or (Ia) are preferably prepared using the alkali and alkaline earth metal hydroxides and hydrides thereof, of which the hydroxides and hydrides of the alkaline earth metals, particularly of sodium and potassium, are preferred and sodium and potassium hydroxide are particularly preferred.

If desired, the compounds of general formula (I) or (Ia) may be converted into the salts thereof, particularly, for pharmaceutical use, into the pharmacologically acceptable acid addition salts with an inorganic or organic acid. Suitable acids include for example succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Hence the invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids such as for example oxalic, fumaric, diglycolic or methanesulphonic acid.

The compounds according to the invention may optionally occur as racemates, but they may also be obtained as pure enantiomers/diastereomers.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid.

The compounds according to formula (I) or (Ia) according to the invention have the meanings hereinbefore whereas in particular the preferred embodiments defined by $R_1$, $R_2$, $R_3$, $R_4$, $R_5$, $R_6$, $R_7$, $R_8$, $R_{8'}$, $R_9$, $R_{9'}$, $R_{13}$, $R_{11}$, $R_{11'}$, $R_{12}$, $R_{13}$, $R_{13'}$, $R_{14}$, $R_{15}$, $R_{15'}$, $R_{16}$, $R_{17}$, $R_{18}$, $R_{19}$, $R_{20}$, $R_{20'}$, $R_{21}$, $R_{21'}$, $R_{22}$, $R_{23}$, A, A', $L_1$, $L_2$, Z, Q, and n in each case are independently selected of one another.

Therapeutic Applications

The above exemplary substances have been tested for binding to CCR2 using a binding assay as outlined herein below:

Cell Culture:

THP-1 cells (human acute monocytic leukaemia cells) were cultured under standardized conditions at 37° C. and 5% CO2 in a humidified incubator. THP-1 cells were cultivated in RPMI 1640 medium (Gibco 21875) containing 1% MEM-NEAA (Gibco 11140) 2 mM L-glutamine, 1.5 g/L sodium bicarbonate, 4.5 g/L glucose, 10 mM HEPES and 1.0 mM sodium pyruvate, 90%; 10% fetal calf serum (FCS Gibco 10500-064). Membranes were prepared from THP-1 cells. THP-1 cells were centrifuged at 300×g at 4° C. for 10 min. The cell pellet was resuspendet in Phosphate Buffer Saline (PBS, including 10 µM Pefabloc and a protease inhibitor mix 'complete', Boehringer Mannheim (1 tablet/50 ml)), to a concentration of 80 cells/ml. The membrane preparation was performed by disrupting the cells by nitrogen decomposition (at 50 bar, for 1 h) in a "Nitrogen Bombe" (Parr Instrument). Cell debris was removed by centrifugation (800×g at 4° C., 1 min). The supernatant was centrifuged at 80000×g, 4° C. for 30 min to sediment the cell membranes. Usually 50 mg of protein (Bradford assay) were yielded from 1×10E9 cells. The membranes were resuspendet in 25 mM HEPES, 25 mM MgCl2, 1 mM CaCl2, 10% Glycerine for storage in aliquots at −80° C. in 25 mM HEPES, 25 mM MgCl2, 1 mM CaCl2, 10% Glycerine and stored at −80° C.

Receptor Membrane Binding Assay:

Perkin Elmer NEX 332 Jod 125 MCP-1, Stock: 2200 Ci/mmol solved in 2000 µl assay buffer, stored at −20° C. THP-1 membrane were adjusted with 25 mM HEPES, pH 7.2; 5 mM MgCl2; 0.5 mM CaCl2; 0.2% BSA assay buffer to a concentration of 2.5 µg/15 Amersham Biosciences PVT-WGA Beads (RPNQ0001) were adjusted with assay buffer to a concentration of 0.24 mg/30 µl. For preparation of the membrane-bead-suspension membranes and beads were incubated for 30 min at RT under rotation (60 rpm) with a ratio of 1:2. Test compounds dissolved in 100% DMSO to a concentration of 10 mM and are further diluted with 100% DMSO to 1 mM. All additional compound dilutions were obtained with assay buffer, final 1% DMSO. Compounds, membrane-bead-suspension and [125I]MCP-1 (ca. 25000 cpm/10 µl) were incubated. Bound radioactivity was determined by scintillation counter after 8 h. Determination of affinity of test compounds (dissociation constant hKi) is calculated by iterative fitting of experimental data using the "easy sys" program, which is based on law of mass action (Schittkowski K. (1994), Numerische Mathematik, Vol. 68, 129-142).

All of the referenced examples have been found to have an activity in this assay of 10 µM or less.

| Example | hKi [nM] |
|---------|----------|
| 1 | 594 |
| 2 | 42 |
| 3 | 6 |
| 4 | 2 |
| 5 | 1 |
| 6 | 21 |
| 6a | 18 |
| 6b | 85 |
| 6c | 133 |
| 6d | 72 |
| 7 | 40 |
| 8 | 100 |
| 9 | 27 |
| 10 | 107 |

Based on the ability of the substances described by formula (I) or (Ia) to effectively bind to CCR2 a range of therapeutic applications can be envisaged. The present invention provides a method for modulating or treating at least one MCP-1 related disease, in a cell, tissue, organ, animal, or patient, as known in the art or as described herein, using at least one CCR2 antagonist of the present invention. The present invention also provides a method for modulating or treating at least one MCP-1 related disease, in a cell, tissue, organ, animal, or patient including, but not limited to, at least one of malignant disease, metabolic disease, an immune or inflammatory related disease, a cardiovascular disease, an infectious disease, or a neurologic disease. Such conditions are selected from, but not limited to, diseases or conditions mediated by cell adhesion and/or angiogenesis. Such diseases or conditions include an immune disorder or disease, a cardiovascular disorder or disease, an infectious, malignant, and/or neurologic disorder or disease, or other known or specified MCP-1 related conditions. In particular, the CCR2 antagonists are useful for the treatment of diseases that involve inflammation such as COPD, angiogenesis such as disease of the eye and neoplastic disease, tissue remodeling such as restenosis, and proliferation of certain cells types particularly epithelial and squamous cell carcinomas. Particular indications include use in the treatment of atherosclerosis, restenosis, cancer metastasis, rheumatoid arthritis, diabetic retinopathy and macular degeneration. The antagonists may also be useful in the treatment of various fibrotic diseases such as idiopathic pulmonary fibrosis, diabetic nephropathy, hepatitis, and cirrhosis. Thus, the present invention provides a method for modulating or treating at least one CCR2 related disease, in a cell, tissue, organ, animal, or patient, as known in the art or as described herein, using at least one CCR2 antagonist of the present invention. Particular indications are discussed below:

Pulmonary Diseases

The present invention also provides a method for modulating or treating at least one malignant disease in a cell, tissue, organ, animal or patient, including, but not limited to, at least one of: pneumonia; lung abscess; occupational lung diseases caused be agents in the form or dusts, gases, or mists; asthma, bronchiolitis fibrosa obliterans, respiratory failure, hypersensitivity diseases of the lungs including hypersensitivity pneumonitis (extrinsic allergic alveolitis), allergic bronchopulmonary aspergillosis, and drug reactions; adult respiratory distress syndrome (ARDS), Goodpasture's Syndrome, chronic obstructive airway disorders (COPD), idiopathic interstitial lung diseases such as idiopathic pulmonary fibrosis and sarcoidosis, desquamative interstitial pneumonia, acute interstitial pneumonia, respiratory bronchiolitis-associated interstitial lung disease, idiopathic bronchiolitis obliterans with organizing pneumonia, lymphocytic interstitial pneumonitis, Langerhans' cell granulomatosis, idiopathic pulmonary hemosiderosis; acute bronchitis, pulmonary alveolar, proteinosis, bronchiectasis, pleural disorders, atelectasis, cystic fibrosis, and tumors of the lung, and pulmonary embolism.

Malignant Diseases

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, renal cell carcinoma, breast cancer, nasopharyngeal carcinoma, malignant histiocytosis, paraneoplastic syndrome/hypercalcemia of malignancy, solid tumors, adenocarcinomas, squamous cell carcinomas, sarcomas, malignant melanoma, particularly metastatic melanoma, hemangioma, metastatic disease, cancer related bone resorption, cancer related bone pain, and the like.

Immune Related Diseases

The present invention also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitisluveitisloptic neuritis, idiopathic pulmonary fibrosis, systemic vasculitis/wegener's granulomatosis, sarcoidosis, orchitislvasectomy reversal procedures, allergiclatopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, traumalhemohage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic diseases, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type IU hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, OKT3 therapy, anti-CD3 therapy, cytokine therapy, chemotherapy, radiation therapy (e.g., including but not limited toasthenia, anemia, cachexia, and the like), chronic salicylate intoxication, and the like.

Cardiovascular Diseases

The present invention also provides a method for modulating or treating at least one cardiovascular disease in a cell, tissue, organ, animal, or patient, including, but not limited to, at least one of cardiac 25 stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, H is bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one CCR2 antagonist to a cell, tissue, organ, animal or patient in need of such modulation, treatment or therapy.

Neurologic Diseases

The present invention also provides a method for modulating or treating at least one neurologic disease in a cell, tissue, organ, animal or patient, including, but not limited to, at least one of: Inflammatory pain, chronic pain, Neuropathic pain such as low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain; neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supra-nucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi. system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like.

Fibrotic Conditions

In addition to the above described conditions and diseases, the present invention also provides a method for modulating or treating fibrotic conditions of various etiologies such as liver fibrosis (including but not limited to alcohol-induced cirrhosis, viral-induced cirrhosis, autoimmune-induced hepatitis); lung fibrosis (including but not limited to scleroderma, idiopathic pulmonary fibrosis); kidney fibrosis (including but not limited to scleroderma, diabetic nephritis, glomerular pehpritis, lupus nephritis); dermal fibrosis (including but not limited to scleroderma, hypertrophic and keloid scarring, burns); myelofibrosis; Neurofibromatosis; fibroma; intestinal fibrosis; and fibrotic adhesions resulting from surgical procedures.

The present invention also provides a method for modulating or treating at least one wound, trauma or tissue injury or chronic condition resulting from or related thereto, in a cell, tissue, organ, animal or patient, including, but not limited to, at least one of: bodily injury or a trauma associated with surgery including thoracic, abdominal, cranial, or oral surgery; or wherein the wound is selected from the group consisting of aseptic wounds, contused wounds, incised wounds, lacerated wounds, non-penetrating wounds, open wounds, penetrating wounds, perforating wounds, puncture wounds, septic wounds, infarctions and subcutaneous wounds; or wherein the wound is selected from the group consisting of ischemic ulcers, pressure sores, fistulae, severe bites, thermal burns and donor site wounds; or wherein the wound is anaphthous wound, a traumatic wound or a herpes associated wound. Donor site wounds are wounds which e.g. occur in connection with removal of hard tissue from one part of the body to another part of the body e.g. in connection with transplantation. The wounds resulting from such operations are very painful and an improved healing is therefore most valuable. Wound fibrosis is also amenable to CCR2 antagonist therapy as the first cells to invade the wound area are neutrophils followed by monocytes which are activated by macrophages. Macrophages are believed to be essential for efficient wound healing in that they also are responsible for phagocytosis of pathogenic organisms and a clearing up of tissue debris. Furthermore, they release numerous factors involved in subsequent events of the healing process. The macrophages attract fibroblasts which start the production of collagen. Almost all tissue repair processes include the early connective tissue formation, a stimulation of this and the subsequent processes improve tissue healing, however, overproduction of connective tissue and collegen can lead to a fibrotic tissue characterized as inelastic and hypoxic. The CCR2 antagonist of the invention can be used in methods for modulating, treating or preventing such sequelae of wound healing.

Other Therapeutic Uses of CCR2 Antagonists

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection, HIV neuropathy, meningitis, hepatitis (A,B or C, or the like), septic arthritis, peritonitis, pneumonia, epiglottitis, *e. coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitislepidydimitis, *legionella*, lyme disease, influenza a, epstein-barr virus, vital-associated hemaphagocytic syndrome, vital encephalitisiaseptic meningitis, and the like.

Any method of the present invention can comprise administering an effective amount of a composition or pharmaceutical composition comprising at least one CCR2 antagonist to a cell, tissue, organ, animal or patient in need of such modulation, treatment or therapy.

Besides being useful for human treatment, these compounds are also useful for veterinary treatment of companion animals, exotic animals and farm animals, including mammals, rodents, and the like.

Combinations

The compounds of formula (I) or (Ia) may be used on their own or in conjunction with other active substances of formula (I) or (Ia) according to the invention. If desired the compounds of formula (I) or (Ia) may also be used in combination with other pharmacologically active substances. It is preferable to use for this purpose active substances selected for example from among β2-adrenoceptor-agonists (short and lon-acting betamimetics), anti-cholinergics (short and lon-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, statins, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK (spleen tyrosine kinase-inhibitors), ZAP-70, FYN, BTK or ITK, inhibitors of MAP kinases as for example p38, ERK1, ERK2, JNK1, JNK2, JNK3 or SAP, inhibitors of the NF-kappaB signalling pathway as for example IKK2 kinase inhibitors, iNOS inhibitors (inducible nitric oxide synthase-inhibitors), MRP4 inhibitors, leukotriene antagonists, leukotriene biosynthese inhibitors as for example 5-Lipoxygenase (5-LO) inhibitors, cPLA2 inhibitors, Leukotriene A4 Hydrolase inhibitors or FLAP inhibitors, non-steroidal antiinfiammatory drugs (NSAIDs) including COX-2 inhibitors, CRTH2 antagonists, DP1-receptor modulators, Thromboxane receptor antagonists, CCR1 antagonists, CCR4 antagonists, CCR5 antagonists, CCR6 antagonists, CCR7 antagonists, CCR8 antagonists, CCR9 antagonists, CCR10 antagonists, CCR11 antagonists, CXCR1 antagonists, CXCR2 antagonists, CXCR3 antagonists, CXCR4 antagonists, CXCR5 antagonists, CXCR6 antagonists, CX3CR1 antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic rezeptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Melanocortin receptor (MC1R, MC2R, MC3R, MC4R, MC5R) modulators, CGRP antagonists, Endothelin antagonists, TNFalpha antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, antiviral drugs, opiate receptor agonists, cannabionoid agonists, sodium channel blockers, N-type calcium channel blockers, serotonergic and noradrenergic modulators, proton pump inhibitors, local anesthetics, VR1 agonists and antagonists, Nicotinic acetylcholine receptor agonists, P2X3 receptor antagonists, NGF agonists and antagonists, NMDA antagonist, potassium channel modulators, GABA modulators, serotonergic and noradrenergic modulators, anti-migraine drugs. The invention also encompasses combinations of three active substances, each selected from one of the above-mentioned categories of compounds. Said list is not considered to have a limiting character.

The betamimetics used are preferably compounds selected from among albuterol, bambuterol, bitolterol, broxaterol, carbuterol, clenbuterol, fenoterol, formoterol, arformoterol, zinterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenol, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzyl-sulphonamide, 5-[2-(5,6-diethyl-indan-2-ylamino)-1-hydroxyethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4- ethoxy-carbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Preferably the beta mimetics are selected from among bambuterol, bitolterol, carbuterol, clenbuterol, fenoterol, formoterol, hexoprenaline, ibuterol, pirbuterol, procaterol, reproterol, salmeterol, sulphonterol, terbutaline, tolubuterol, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxycarbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof.

Particularly preferred betamimetics are selected from among fenoterol, formoterol, salmeterol, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethano 1, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethano 1, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(4-phenoxy-acetate ethyl)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one and 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, optionally in the form of the racemates, enantiomers, diastereomers thereof and optionally in the form of the pharmacologically acceptable acid addition salts, solvates or hydrates thereof.

Of these betamimetics those which are particularly preferred according to the invention are formoterol, salmeterol, 3-(4-{6-[2-hydroxy-2-(4-hydroxy-3-hydroxymethyl-phenyl)-ethylamino]-hexyloxy}-butyl)-benzenesulphonamide, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1.1 dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 5-[2-(5,6-diethyl-indan-2-ylamino)-1-hydroxy-ethyl]-8-hydroxy-1H-quinolin-2-one, optionally in the form of the racemates, enantiomers, diastereomers thereof and optionally in the form of the pharmacologically acceptable acid addition salts, solvates or hydrates thereof.

According to the invention the acid addition salts of the betamimetics are preferably selected from among hydrochloride, hydrobromide, hydriodide, hydrosulphate, hydrophosphate, hydromethanesulphonate, hydronitrate, hydromaleate, hydroacetate, hydrobenzoate, hydrocitrate, hydrofumarate, hydrotartrate, hydroxalate, hydrosuccinate, hydrobenzoate and hydro-p-toluenesulphonat, preferably hydrochloride, hydrobromide, hydrosulphate, hydrophosphate, hydro fumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among the tiotropium salts, oxitropium salts, flutropium salts, ipratropium salts, glycopyrronium salts, trospium salts, tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, -scopine 3,3'-difluorobenzilate methobromide, tropenol 9-hydroxy-fluorene-9-carboxylate -methobromide, tropenol 9-fluoro-fluorene-9-carboxylate -methobromide, scopine 9-hydroxy-fluoren-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, methyl -cyclopropyltropine 4,4'-difluorobenzilate methobromide, tropenol 9-hydroxy-xanthene-9-carboxylate -methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide, scopine 9-hydroxymethyl-xanthene-9-carboxylate methobromide, optionally in the form of the solvates or hydrates thereof.

In the above-mentioned salts the cations tiotropium, oxitropium, flutropium, ipratropium, glycopyrronium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among prednisolone, prednisone, butixocort-propionate, flunisolide, beclomethasone, triamcinolone, budesonide, fluticasone, mometasone, ciclesonide, rofleponide, dexamethasone, betamethasone, deflazacort, RPR-106541, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferred is the steroid selected from among flunisolide, beclomethasone, triamcinolone, budesonide, fluticasone, mometasone, ciclesonide, rofleponide, dexamethasone, NS-126, (S)-fluoromethyl 6,9-difluoro-17-[(2-furanylcarbonyl)oxy]-11-hydroxy-16-methyl-3-oxo-androsta-1,4-diene-17-carbothionate and (S)-(2-oxo-tetrahydro-furan-3S-yl) 6,9-difluoro-11-hydroxy-16-methyl-3-oxo-17-propionyloxy-androsta-1,4-diene-17-carbothionate, optionally in the form of the racemates, enantiomers or diastereomers thereof and optionally in the form of the salts and derivatives, solvates and/or hydrates thereof.

Particularly preferred is the steroid selected from among budesonide, fluticasone, mometasone, ciclesonide and (S)-fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates thereof.

PDE4 inhibitors which may be used are preferably compounds selected from among enprofyllin, theophyllin, roflumilast, ariflo (cilomilast), tofimilast, pumafentrin, lirimilast, arofyllin, atizoram, D-4396 (Sch-351591), AWD-12-281 (GW-842470), NCS-613, CDP-840, D-4418, PD-168787, T-440, T-2585, V-11294A, C1-1018, CDC-801, CDC-3052, D-22888, YM-58997, Z-15370, N-(3,5-dichloro-1-oxo-pyridin-4-yl)-4-difluoromethoxy-3-cyclopropylmethoxybenzamide, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-5-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexane-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl[4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

The PDE4-inhibitor used are preferably compounds selected from among enprofyllin, roflumilast, ariflo (cilomilast), arofyllin, atizoram, AWD-12-281 (GW-842470), T-440, T-2585, PD-168787, V-11294A, C1-1018, CDC-801, D-22888, YM-58997, Z-15370, N-(3,5-dichloro-1-oxo-pyridin-4-yl)-4-difluoromethoxy-3-cyclopropylmethoxybenzamide, cis[4-cyano-4-(3-cyclopentyloxy-4-methoxyphenyl) cyclohexane-1-carboxylic acid], 2-carbomethoxy-4-cyano-4-(3-cyclopropylmethoxy-4-difluoromethoxyphenyl) cyclohexan-1-one, cis[4-cyano-4-(3-cyclopropylmethoxy-4- difluoromethoxyphenyl)cyclohexan-1-ol], 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropane-acetic acid and [2-[[2-(4-tert-butyl-2-thiazolyl)-5-benzofuranyl]oxymethyl]phenyl]acetic acid, optionally in the form of the racemates, enantiomers or diastereomers, optionally in the form of the pharmacologically acceptable acid addition salts and optionally in the form of the salts and derivatives, solvates and/or hydrates thereof.

Preferably the LTD4-antagonist is selected from among montelukast, pranlukast, zafirlukast, MCC-847 (ZD-3523), MN-001, MEN-91507 (LM-1507), VUF-5078, VUF-K-8707 and L-733321, optionally in the form of the racemates, enantiomers or diastereomers, optionally in the form of the pharmacologically acceptable acid addition salts and optionally in the form of the salts and derivatives, solvates and/or hydrates thereof.

Particularly preferably the LTD4-antagonist is selected from among montelukast, pranlukast, zafirlukast, MCC-847 (ZD-3523), MN-001 and MEN-91507 (LM-1507), optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among 4-[(3-chloro-4-fluorophenyl) amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydro furan-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidin, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydro furan-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydro furan-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydro furan-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydro furan-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxyl}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morphohonyl)-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methane sulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydro furan-2-yl)methoxy]-quinazoline, 4-[(3-chloro-4-fluoro-phenyl)amino]-6-(1-methane sulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, Cetuximab, Trastuzumab, ABX-EGF and Mab ICR-62, optionally in the form of the racemates, enantiomers or diastereomers thereof, optionally in the form of the pharmacologically acceptable acid addition salts, the solvates and/or hydrates thereof.

Preferred EGFR inhibitors are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-[(R)-6-methyl-2-oxo-morpholin-4-yl)-1-oxo-2-buten-1-yl]amino}-7-[(S)-(tetrahydro furan-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydro furan-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydro furan-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydro furan-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydro furan-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydro furan-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methane sulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydro furan-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethane-sulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydro furan-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and Cetuximab, optionally in the form of the racemates, enantiomers or diastereomers thereof, optionally in the form of the pharmacologically acceptable acid addition salts, the solvates and/or hydrates thereof.

Preferable the EGFR-inhibitors are selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydro furan-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydro furan-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydro furan-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynylphenyl)amino]-6-(tetrahydropyran-4-yloxy]-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxyethyl)carbonyl]-piperidin-4-yloxy}-7-methoxy-quinazoline, optionally in the form of the racemates, enantiomers or diastereomers thereof, optionally in the form of the pharmacologically acceptable acid addition salts, the solvates and/or hydrates thereof.

EGFR-inhibitors are preferably selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-64 {4-[N-(2-methoxy-ethyl)-N-methyl-amino]-1-oxo-2-buten-1-yl}amino}-7-cyclopropylmethoxy-quinazoline, 4-[(3-ethynyl-phenyl)amino]-6,7-bis-(2-methoxy-ethoxy)-quinazoline, 4-[(3-chloro-4-fluorophenyl)amino]-6-{[4-(morpholin-4-yl)-1-oxo-2-buten-1-yl]amino}-7-[(tetrahydro furan-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-(trans-4-methanesulphonylamino-4-[(3-chloro-4-fluoro-phenyl)amino]-6-(tetrahydropyran-3-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{-N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline and 4-[(3-chloro-4-fluoro-phenyl)amino]-6-(1-cyano-piperidin-4-yloxy)-7-methoxy-quinazoline optionally in the form of the racemates, enantiomers or diastereomers thereof, optionally in the form of the pharmacologically acceptable acid addition salts, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among 4-(2-chlorophenyl)-9-methyl-2-[3 (4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepines.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-(3-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, clycolithocholic acid sulphate, ibuprofen, indomethacin, indoprofen, ketoprofen, lithocholic acid sulphate, methotrexate, MK571 ((E)-3-[[[3-[2-(7-chloro-2-quinolinypethenyl]phenyl]-[[3-dimethylamino)-3-oxopropyl]thio]methyl]thio]-propanoic acid), α-naphthyl-β-D-glucuronide, nitrobenzyl mercaptopurine riboside, probenecid, PSC833, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

MRP4-inhibitors are preferably selected from among N-acetyl-dinitrophenyl-cysteine, dehydroepiandrosterone 3-sulphate, dilazep, dinitrophenyl-5-glutathione, estradiol 3,17-disulphate, flurbiprofen, glycocholate, glycolithocholic acid sulphate, ibuprofen, indomethacin, indoprofen, lithocholic acid sulphate, MK571, PSC833, sildenafil, taurochenodeoxycholate, taurocholate, taurolithocholate, taurolithocholic acid sulphate, trequinsin and zaprinast, dipyridamole, optionally in the form of the racemates, enantiomers, diastereomers and the pharmacologically acceptable acid addition salts and hydrates thereof.

Particularly preferred MRP4-inhibitors are selected from among dehydroepiandrosterone 3-sulphate, estradiol 3,17-disulphate, flurbiprofen, indomethacin, indoprofen, MK571, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydrop-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the CCR2 inhibitors, MRP4-inhibitors and another active substance according to the invention, such as, for example, an anticholinergic, a steroid, an LTD4-antagonist or a betamimetic, and the preparation thereof and the use thereof for treating respiratory complaints.

The iNOS-inhibitors used are preferably compounds selected from among: S-(2-aminoethyl)isothiourea, aminoguanidine, 2-aminomethylpyridine, AMT, L-canavanine, 2-iminopiperidine, S-isopropylisothiourea, S-methylisothiourea, S-ethylisothiourea, S-methyltiocitrulline, S-ethylthiocitrulline, L-NA ($N^{\omega}$-nitro-L-arginine), L-NAME ($N^{\omega}$-nitro-L-arginine methylester), L-NMMA ($N^{G}$-monomethyl-L-arginine), L-NIO ($N^{\omega}$-iminoethyl-L-ornithine), L-NIL ($N^{\omega}$-iminoethyl-lysine), (S)-6-acetimidoylamino-2-aminohexanoic acid (1H-tetrazol-5-yl)-amide (SC-51) (*J. Med. Chem.* 2002, 45, 1686-1689), 1400W, (S)-4-(2-acetimidoylamino-ethylsulphanyl)-2-amino-butyric acid (GW274150) (*Bioorg. Med. Chem. Lett.* 2000, 10, 597-600), 2-[2-(4-methoxy-pyridin-2-yl)-ethyl]-3H-imidazo[4,5-b]pyridine (BYK191023) (*Mol. Pharmacol.* 2006, 69, 328-337), 2-((R)-3-amino-1-phenyl-propoxy)-4-chloro-5-fluorobenzonitrile (WO 01/62704), 2-((1R.3S)-3-amino-4-hydroxy-1-thiazol-5-yl-butylsulphanyl)-6-trifluoromethyl-nicotinonitrile (WO 2004/041794), 2-((1R.3S)-3-amino-4-hydroxy-1-thiazol-5-yl-butylsulphanyl)-4-chloro-benzonitrile (WO 2004/041794), 2-((1R.3S)-3-amino-4-hydroxy-1-thiazol-5-yl-butylsulphanyl)-5-chloro-benzonitrile (WO 2004/041794), (2S,4R)-2-amino-4-(2-chloro-5-trifluoromethyl-phenylsulphanyl)-4-thiazol-5-yl-butan-1-ol (WO 2004/041794), 2-((1R.3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamines such as e.g. AR-C102222 (*J. Med. Chem.* 2003, 46, 913-916), (1S.5S.6R)-7-chloro-5-methyl-2-aza-bicyclo[4.1.0]hept-2-en-3-ylamine (ONO-1714) (*Biochem. Biophys. Res. Commun.* 2000, 270, 663-667), (4R.5R)-5-ethyl-4-methyl-thiazolidin-2-ylideneamine (*Bioorg. Med. Chem.* 2004, 12, 4101), (4R.5R)-5-ethyl-4-methyl-selenazolidin-2-ylideneamine (*Bioorg. Med. Chem. Lett.* 2005, 15, 1361), 4-aminotetrahydrobiopterine (*Curr. Drug Metabol.* 2002, 3, 119-121), (E)-3-(4-chloro-phenyl)-N-(1-{2-oxo-2-[4-(6-trifluoromethyl-pyrimidin-4-yloxy)-piperidin-1-yl]-ethylcarbamo yl}-2-pyridin-2-yl-ethyl)-acrylamide (FR260330) (*Eur. J. Pharmacol.* 2005, 509, 71-76), 3-(2,4-difluoro-phenyl)-6-[2-(4-imidazol-1-ylmethyl-phenoxy)-ethoxy]-2-phenyl-pyridine (PPA250) (*J. Pharmacol. Exp. Ther.* 2002, 303, 52-57), methyl 3-{[(benzo[1.3]dioxol-5-ylmethyl)-carbamoyl]-methyl}-4-(2-imidazol-1-yl-pyrimidin-4-yl)-piperazin-1-carboxylate (BBS-1) (*Drugs Future* 2004, 29, 45-52), (R)-1-(2-imidazol-1-yl-6-methyl-pyrimidin-4-yl)-pyrrolidine-2-carboxylic acid (2-benzo[1.3]dioxol-5-yl-ethyl)-amide (BBS-2) (*Drugs Future* 2004, 29, 45-52) and the pharmaceutical salts, prodrugs or solvates thereof.

Compounds which may be used as SYK-inhibitors are preferably compounds selected from among: R343 or R788.

Examples of preferred MAP kinase inhibitors, as for example p38, ERK1, ERK2, JNK1, JNK2, JNK3 or SAP, which may be mentioned include SCIO-323, SX-011, SD-282, SD-169, NPC-037282, SX-004, VX-702, GSK-681323, GSK-856553, ARRY-614, ARRY-797, ARRY-438162, ARRY-p38-002, ARRY-371797, AS-602801, AS-601245, AS-602183, CEP-1347, KC706, TA-5493, RO-6226, Ro-1487, SC-409, CBS-3595, VGX-1027, PH-797804, BMS-582949, TA-5493 and BIRB-796 optionally in racemic form, as enantiomers, diastereomeres or as pharmacologically acceptable salts, solvates or hydrates.

Examples of preferred inhibitors of the NF-κB signalling pathway including IKK2 kinase inhibitors which may be mentioned include: MD-1041, MLN-041 und AVE-0547 optionally in racemic form, as enantiomers, diastereomeres or as pharmacologically acceptable salts, solvates or hydrates.

Examples of preferred Leukotriene biosynthesis inhibitors, as for example 5-Lipoxygenase (5-LO) inhibitors, cPLA2 inhibitors, Leukotriene A4 hydrolase inhibitors oder FLAP inhibitors, which may be mentioned include zileuton, tipelukast, licofelone, darapladib, TA-270, IDEA-033, IDEA-070, NIK-639, ABT-761, fenleuton, tepoxalin, AM-103, AM-803, Abbott-79175, Abbott-85761, PLT-3514, CMI-903, PEP-03, CMI-977, MLN-977, CMI-947, LDP-977, efipladib, PLA-695, veliflapon, MK-591, MK-886 und BAYx1005 optionally in racemic form, as enantiomers, diastereomeres or as pharmacologically acceptable salts, solvates or hydrates.

Examples of preferred non-steroidal anti-inflammatory agents (NSAIDs) which may be mentioned include COX-2 inhibitors: propionic acid derivatives (alminoprofen, benoxaprofen, bucloxic acid, carprofen, fenhufen, fenoprofen, flubiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenyl-carboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib) optionally in racemic form, as enantiomers, diastereomeres or as pharmacologically acceptable salts, solvates or hydrates.

Examples of preferred CCR1 antagonists which may be mentioned include AZD-4818, CCX-354, MLN-3701, MLN-3897, optionally in racemic form, as enantiomers, diastereomeres or as pharmacologically acceptable salts, solvates or hydrates.

Examples of preferred CCR5 antagonists which may be mentioned include maraviroc, INCB-15050. CCR5 mAb004, GSK-706769, PRO-140, SCH-532706, vicriviroc and nifeviroc optionally in racemic form, as enantiomers, diastereomeres or as pharmacologically acceptable salts, solvates or hydrates.

Examples of preferred CXCR1 or CXCR2 antagonists which may be mentioned include SCH-527123 and SB-656933 optionally in racemic form, as enantiomers, diastereomeres or as pharmacologically acceptable salts, solvates or hydrates.

Examples of preferred Neurokinin (NK1 or NK2) antagonists which may be mentioned include Saredutant, Nepadutant, PRX-96026 und Figopitant optionally in racemic form, as enantiomers, diastereomeres or as pharmacologically acceptable salts, solvates or hydrates.

Examples of preferred puringeric receptor modulators, including P2X7 inhibitors, which may be mentioned include AZD-9056 optionally in racemic form, as enantiomers, diastereomeres or as pharmacologically acceptable salts, solvates or hydrates.

Examples of preferred PPAR gamma modulators which may be mentioned include Rosiglitazone, Ciglitazone, Pioglitazone and SMP-028 optionally in racemic form, as enantiomers, diastereomeres or as pharmacologically acceptable salts, solvates or hydrates.

Examples of preferred Interleukin 1-beta converting enzyme (ICE) inhibitors which may be mentioned include Pralnacasan, VRT-18858, RU-36384, VX-765 and VRT-43198 optionally in racemic form, as enantiomers, diastereomeres or as pharmacologically acceptable salts, solvates or hydrates.

Examples of preferred Toll-like receptor (TLR) modulators which may be mentioned include Resiquimod, PF-3512676, AVE-0675, Heplisav, IMO-2055, CpG-28, TAK-242, SAR-21609, RC-52743198 and 852A optionally in racemic form, as enantiomers, diastereomeres or as pharmacologically acceptable salts, solvates or hydrates.

Examples of preferred VLA4 antagonists which may be mentioned include Natalizumab, Valategrast, TBC-4746, CDP-323 and TL-1102 optionally in racemic form, as enantiomers, diastereomeres or as pharmacologically acceptable salts, solvates or hydrates.

Examples of preferred ICAM-1 inhibitors which may be mentioned include BIRT-2584 optionally in racemic form, as enantiomers, diastereomeres or as pharmacologically acceptable salts, solvates or hydrates.

Examples of preferred anti-TNF antibodies which may be mentioned include Infliximab, Adalimumab, Golimumab. CytoFab and Etanercept.

Examples of preferred mucoregulators which may be mentioned include MSI-2216, Erdosteine, Fluorovent, Talniflumate, INO-4995, BIO-11006, VR-496 and fudosteine optionally in racemic form, as enantiomers, diastereomeres or as pharmacologically acceptable salts, solvates or hydrates.

Examples of preferred Antiviral drugs which may be mentioned include acyclovir, tenovir, pleconaril, peramivir, pocosanol.

Examples of preferred Antibiotic drugs like gentamicin, streptomycin, geldanamycin, doripenem, cephalexin, cefaclor, ceftazichine, cefepime, erythromycin, vancomycin, aztreonam, amoxicillin, bacitracin, enoxacin, mafenide, doxycycline, chloramphenicol.

Examples of preferred opiate receptor agonists are selected from among morphine, propoxyphene (Darvon), tramadol, buprenorphin.

Examples of preferred anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab.

Examples of preferred IL-1 receptor antagonists such as but not limited to Kineret; Sodium channel blockers: carbamazepine, mexiletine, lamotrigine, tectin, lacosamide Examples of preferred N-type calcium channel blockers are selected from among Ziconotide.

Examples of preferred Serotonergic and noradrenergic modulators such as but not limited to paroxetine, duloxetine, clonidine, amitriptyline, citalopram; Examples of preferred Histamine H1 receptor antagonists such as but not limited to bromophtniramint, chlorpheniramine, dexchlorpheniramine, triprolidine, clemastine, diphenhydramine, diphenylpyraline, tripelennamine, hydroxyzine, methdiJazine, promethazine, trimeprazine, azatadine, cyproheptadine, antazoline, pheniramine pyrilamine, astemizole, terfenadine, loratadine, cetirizine, deslo-ratadine, fexofenadine and levocetirizine.

Examples of preferred Histamine H2 receptor antagonists such as but not limited to cimetidine, famotidine and ranitidine.

Examples of preferred proton pump inhibitors such as but not limited to omeprazole, pantoprazole and esomeprazole.

Examples of preferred Leukotriene antagonists and 5-lipoxygenase inhibitors such as but not limited to zafirlukast, montelukast, pranlukast and zileuton.

Examples of preferred local anesthetics such as but not limited to ambroxol, lidocaine.

Examples of preferred potassium channel modulators such as but not limited to retigabine.

Examples of preferred GABA modulators such as but not limited to lacosamide, pregabalin, gabapentin.

Examples of preferred anti-migraine drugs such as but not limited to sumatriptan, zolmitriptan, naratriptan, eletriptan, telcegepant.

Examples of preferred NGF antibodies such as but not limited to RI-724.

Combination therapy is also possible with new principles for the treatment of pain e.g. P2X3 antagonists, VR1 antagonists, NK1 and NK2 antagonists, NMDA antagonists, mGluR antagonists and the like.

Pharmaceutical Formulations

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised in that they contain one or more compounds of formula (I) or (Ia) according to the preferred embodiments above.

It is particularly preferable if the compounds of formula (I) or (Ia) are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula (I) or (Ia) are administered by inhalation, particularly preferably if they are administered once or twice a day. For this purpose, the compounds of formula (I) or (Ia) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula (I) or (Ia) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain the active substances of formula (I) or (Ia) dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula (I) or (Ia) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. For the treatment forms described above, ready-to-use packs of a medicament for the treatment of respiratory complaints are provided, containing an enclosed description including for example the words respiratory disease, COPD or asthma, a pteridine and one or more combination partners selected from those described above.

EXPERIMENTAL PROCEDURES AND SYNTHETIC EXAMPLES

List of Abbreviations

ACN acetonitrile
APCI atmospheric pressure chemical ionization (in MS)
BINAP (1,1'-Binaphthalene-2,2'-diyl)bis(di phenylphosphine)
Ctrl control
DAD diode array detector
DMA N,N-dimethylacetamide'
DMF N,N-dimethylformamide
DMSO dimethyl sulfoxide
EI electron impact (in MS)
ESI electrospray ionization (in MS)
ex example
GC/MS gas chromatography with mass spectrometric detection
h hour(s)
HATU O-(7-azabenzotriazol-1-yl)-N,N,N',N'-tetramethyluronium hexafluoro-phosphate
HPLC high performance liquid chromatography
HPLC/MS coupled high performance liquid chromatography-mass spectrometry
min minutes
MS mass spectrometry
NMR nuclear magnetic resonance
$R_t$ retention time (in HPLC)
sec secondary
TBTU O-(1H-benzo-1,2,3-triazol-1-yl)-N,N,N',N'-tetramethyluronium tetrafluoroborate
tert tertiary
TFA trifluoroacetic acid
THF tetrahydrofurane
TLC thin-layer chromatography
UV ultraviolet absorption
Xphos 2-Dicyclohexylphosphino-2',4',6'-triisopropylbiphenyl Analytical Methods
HPLC Methods
Method:
 2Ca
 Column: MERCK; Chromolith Flash; RP18e; 25×4.6 mm
 Mobile phase: A=water+0.1% HCOOH; B=ACN+0.1% HCOOH
 Flow rate: 1.6 ml/min

|  | A % | B % | Time [min] |
|---|---|---|---|
| Gradient: | 90 | 10 | 0.00 |
|  | 10 | 90 | 2.70 |
|  | 10 | 90 | 3.00 |
|  | 90 | 10 | 3.30 |

Equipment
Instrument: Agilent Technology; HP 1100 Series, DAD
Detection: UV 190-400 nm
Detection: Agilent Technology; HP 1100 MSD
Ion source: ESI+
Method:
2Cc
Column: MERCK; Chromolith Flash; RP18e; 25×4.6 mm, at 60° C.
Mobile: A=water+0.1% HCOOH; B=MeOH
Flow rate: 2.5 ml/min

|  |  | A % | B % | Time [min] |
|---|---|---|---|---|
| Gradient: |  | 90 | 10 | 0.00 |
|  |  | 0 | 100 | 1.61 |
|  |  | 0 | 100 | 2.25 |

B-STD
Column: WATERS; XBridge; C18; 30×3.00 mm, at 60° C.
Mobile: A=water+0.1% NH4OH; B=MeOH

|  | A % | B % | Time [min] | Flow rate [ml/min] |
|---|---|---|---|---|
| Gradient: | 95 | 5 | 0.00 | 2.2 |
|  | 10 | 90 | 1.10 | 2.2 |
|  | 10 | 90 | 1.22 | 2.2 |
|  | 0 | 100 | 1.25 | 2.2 |
|  | 0 | 100 | 1.65 | 2.2 |

Equipment
Instrument: Agilent Technology; HP 1200 Series, DAD
Detection: UV 190-400 nm
Detection: Agilent Technology; 1200 MSD
Ion source: ESI+
Method:
2I (Isocratic)
Column: DAICEL AS-H 5 µm, 4.6×250 mm
Mobile phase: A=Hexane; B=EtOH (con AS-H), IPA (con AD-H) A/B=98/2%
Flow rate: 1 ml/min
2Ja (Isocratic)
Column: DAICEL Chiralpack AD-H 5 µm, 4.6×250 mm
Mobile phase: A=Hexane; B=Isopropanol A/B=80/20%
Flow rate: 1 ml/min
Equipment
Instrument: LC Agilent Technologies. HPLC 1100 Serie, DAD Version A.
Detection: UV 220-300 nm
Method:
Y1_1
Column: Waters, XBridge C18, 4.6×30 mm, 3.5 µm, 60° C.
Mobile: A=water+0.1% TFA; B=MeOH+0.1% TFA

|  | A % | B % | Time [min] | Flow rate [ml/min] |
|---|---|---|---|---|
| Gradient: | 95 | 5 | 0.00 | 4 |
|  | 95 | 5 | 0.15 | 4 |
|  | 0 | 100 | 1.70 | 4 |
|  | 0 | 100 | 2.25 | 4 |

Equipment
Instrument: Agilent Technology; HP 1100 Series, DAD
Detection: UV 190-400 nm
Detection: Agilent Technology; 1100 MSD
Ion source: ESI+

Method:
Z1_2
Column: Waters, XBridge C18, 3×30 mm, 2.5 µm, 60° C.
Mobile: A=water+0.2% TFA; B=MeOH

|  | A % | B % | Time [min] | Flow rate [ml/min] |
|---|---|---|---|---|
| Gradient: | 95 | 5 | 0.00 | 2.2 |
|  | 95 | 5 | 0.05 | 2.2 |
|  | 0 | 100 | 1.40 | 2.2 |
|  | 0 | 100 | 1.80 | 2.2 |

Equipment
Instrument: Agilent Technology; HP 1200 Series, DAD
Detection: UV 190-400 nm
Detection: Agilent Technology; 1200 MSD
Ion source: ESI+
GC-MS Methods:
Methods:
3A
Column: Agilent DB-5MS, 25 m×0.25 mm×0.25 µm
Carrier gas: Helium, 1 mL/min costant flow
Oven Program: 50° C. (hold 1 min.), to 100° C. in 10° C./min, to 200° C. in 20° C./min, to 300° C. in 30° C./min
3B
Column: Agilent DB-5MS, 25 m×0.25 mm×0.25 µm
Carrier gas: Helium, 1 mL/min costant flow
Oven Program: 80° C. to 110° C. in 10° C./min (hold 40 min), to 280° C. in 30° C./min
Equipment
Instrument: GC/MS Finnigan TRACE GC, TRACE MS quadrupole
Detection: TRACE MS quadrupole
Ion source: EI

SYNTHESIS OF INTERMEDIATES

Intermediate 1

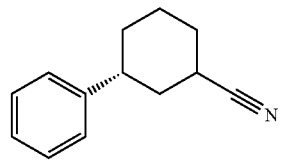 [SMILES: N#CC1CCC[C@@H](c2ccccc2)C1]

Commercially available (R)-3-phenylcyclohexanone (2.0 g, 11.48 mmol) and 1-isocyanomethanesulfonyl-4-methylbenzene (2.91 g, 14.92 mmol) in 10 ml of 1,2-dimethoxyethane were stirred at 0° C. A solution of potassium tert-butoxide (2.57 g, 22.96 mmol) in 10 ml 1,2-dimethoxyethane and 20 ml tert-butanol was added dropwise and the reaction mixture was allowed to reach room temperature and stirred overnight. The reaction mixture was diluted with diethyl ether and washed with ice water. The organic phase was separated, washed with brine, dried over sodium sulfate and concentrated under vacuum. 2.1 g (11.2 mmol) of the desired product were obtained.
GC/MS (method 3A) $R_t$=11.52 min and 11.68 min (diastereoisomeric mixture) $[M]^+$=185

Intermediate 2

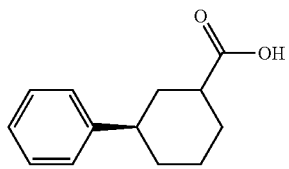 [SMILES: O=C(O)C1CCC[C@@H](c2ccccc2)C1]

Intermediate 1 (2.1 g, 11.2 mmol) was stirred under reflux in 20 ml of 96% sulfuric acid and 20 ml water overnight. The reaction mixture was cooled, treated with a 30% aqueous solution of sodium hydroxide and ice and washed with dichloromethane. The basic water phase was treated with 37% aqueous solution of hydrochloric acid. The acidic aqueous solution was extracted with dichloromethane. The organic phase was washed with brine, dried over sodium sulfate and concentrated under vacuum. 1.85 g (9.1 mmol) of the desired compound were obtained as a diastereoisomeric mixture and used in the next steps without further purification.

Intermediate 3a

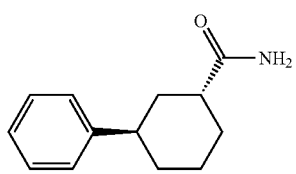 [SMILES: NC(=O)[C@@H]1CCC[C@@H](c2ccccc2)C1]

Intermediate 2 (1.85 g, 9.06 mmol, mixture of 2 diastereomers) and triethylamine (2.02 ml, 14 mmol) were stirred at 0° C. in 10 ml tetrahydrofuran. A solution of ethylchloroformate (1.29 ml, 13.58 mmol) in 5 ml tetrahydrofuran was added dropwise and the reaction mixture was stirred at 0° C. for 1 h. Then, 10 ml of a 30% aqueous solution of ammonium hydroxide were added dropwise and the reaction mixture was allowed to reach room temperature and stirred overnight. The reaction mixture was concentrated under vacuum, dissolved with dichloromethane, washed with a 1M aqueous solution of sodium hydroxide, washed with brine, dried over sodium sulfate and concentrated under vacuum. The crude product was purified by flash chromatography (Isolute silica cartridge 70 g; eluent: dichloromethane/methanol=99/1%). 145 mg (0.71 mmol) of diastereoisomerically pure (1R,3R)-3-phenyl-cyclohexanecarboxylic acid amide (relative stereochemistry assigned by NMR) were obtained.
GC/MS (method 3A) $R_t$=12.88 min
$[M]^+$=203

Intermediate 3b

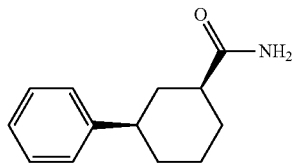 [SMILES: NC(=O)[C@H]1CCC[C@@H](c2ccccc2)C1]

Further elution of the column gave 230 mg (1.13 mmol) of the diastereoisomerically pure (1S,3R)-3-phenyl-cyclohexanecarboxylic acid amide (relative stereochemistry assigned by NMR).
GC/MS (method 3A) $R_t$=13.03 min
$[M]^+$=203

Intermediate 4

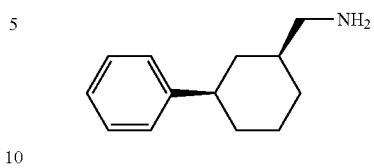

4.53 ml of a 1M solution of lithium aluminium hydride (4.53 mmol) in tetrahydrofuran was dissolved in 30 ml tetrahydrofuran and stirred at 0° C. under nitrogen atmosphere. Intermediate 3b (230 mg, 1.13 mmol) in 10 ml tetrahydrofuran was added dropwise. The reaction mixture was stirred at 0° C. for 2 h and then quenched with water and ice. The reaction mixture was extracted with dichlorometane. The organic phase was washed with a 1M aqueous solution of sodium hydroxide, brine, dried over sodium sulfate and concentrated under vacuum. 180 mg (0.95 mmol) of the desired product were obtained.
GC/MS (method 3A) $R_t$=11.47 min
$[M]^+$=189

Intermediate 5a

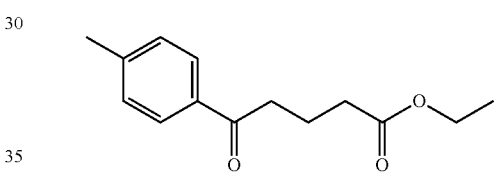

To a solution of lithium bromide (24 g, 277.1 mmol) in 500 ml of dry tetrahydrofurane, stirred under nitrogen atmosphere, copper(I) bromide (19.87 g, 138.5 mmol) was added. The reaction mixture was stirred at room temperature until a solution was obtained. Then, the reaction mixture was cooled to 0° C. and a 0.5M solution commercially available of 4-tolyl magnesium bromide in THF (277.1 ml, 138.5 mmol) was added. Then, commercially available 4-chlorocarbonyl-butyric acid ethyl ester (19 g, 115.4 mmol) was added and the reaction mixture was stirred at 0° C. for 18 h.

500 ml of a saturated aqueous ammonium chloride solution was added and the reaction mixture was extracted twice with dichloromethane. The organic phase was washed with a saturated aqueous sodium bicarbonate solution, dried over sodium sulfate and concentrated under vacuum. The crude product (20 g) was used in the next step without any purification.

Intermediate 6a

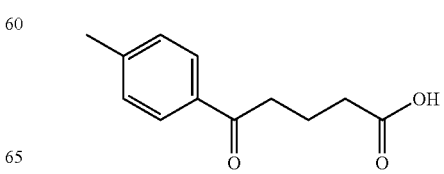

To a solution of intermediate 5a (20 g, 90.8 mmol) in 50 ml of tetrahydrofurane 50 ml of water and lithium hydroxide monohydrate (11.43 g, 274.40 mmol) were added and the reaction mixture was stirred at 50° C. for 1 h.

The reaction mixture was extracted with ethyl acetate and the layers were separated. The aqueous layer was acidified with aqueous HCl (37%) until pH 1 and then extracted with dichloromethane. The organic layer was dried over sodium sulfate and concentrated under vacuum. The crude product was triturated with diisopropyl ether. The solvent was removed by filtration yielding the desired product (13 g, 63.1 mmol).

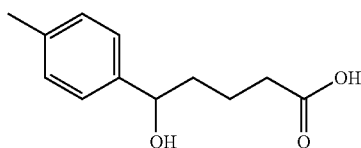

Intermediate 7a

A suspension of intermediate 6a (11.5 g, 55.8 mmol) in 250 ml water was cooled to 10°. Then, potassium hydroxide (7.82 g, 139.4 mmol) and sodium borohydride (1.83 g, 48.5 mmol) were added and the reaction mixture was allowed to reach room temperature and stirred for 2 h. 13 ml of a 12M aqueous hydrochloric acid was added and the reaction mixture was extracted with ethyl acetate. The organic layer was dried over sodium sulfate and concentrated under vacuum to give the crude product (11 g, 52.8 mmol).

Intermediate 8a

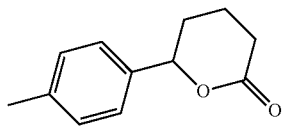

Intermediate 7a (6 g, 28.8 mmol) was dissolved in 100 ml of dichloromethane. 1.5 ml trifluoroacetic acid were added and the reaction mixture was stirred at room temperature for 18 h. The reaction mixture was diluted with 50 ml of dichloromethane and washed with 50 ml of a saturated aqueous sodium bicarbonate solution and water. The organic layer was dried over sodium sulfate and removed under vacuum to give the desired product (4.38 g, 23.0 mmol).

Intermediate 9a

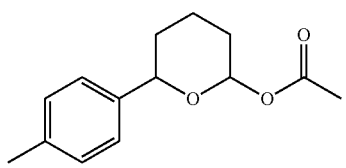 [SMILES: CC(=O)OC1CCCC(c2ccc(C)cc2)O1]

A solution of intermediate 8a (4.38 g, 23.0 mmol) in 110 ml of dichloromethane was cooled to −78° C. Then, a 1M solution of diisobutylaluminiumhydride (46.15 ml, 46.15 mmol) in dichloromethane was added dropwise. The reaction mixture was stirred at −78° C. for 2 h. 100 ml of methanol were added at −78° C. and the reaction mixture was allowed to reach room temperature. The reaction mixture was concentrated under vacuum and the crude product obtained was triturated with ethyl ether. The precipitate was filtered off and washed with diethyl ether. The organic layer was removed under vacuum to give the crude lactol (4.4 g, 22.9 mmol). The lactol was dissolved in 80 ml of dry dichloromethane and cooled to 0° C. Then, triethylamine (4.96 ml, 34.3 mmol), acetic anhydride (2.54 ml, 27.5 mmol) and 4-dimethylaminopyridine (279.6 mg, 2.3 mmol) were added. The reaction mixture was allowed to reach room temperature and stirred for 1 h. A saturated aqueous sodium bicarbonate solution was added and the mixture was extracted with dichloromethane. The organic phase was dried over sodium sulfate and concentrated under vacuum. The residue was purified by flash chromatography (Biotage SP1 cartridge 50 g, eluent: cyclohexane/ethyl acetate=95/5) to give the desired product (4 g, 17.1 mmol).

Intermediate 10a

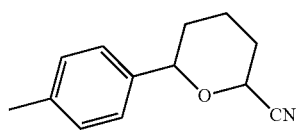

Trimethylsilylcyanide (0.52 ml, 4.16 mmol) and borontrifluoride etherate (0.27 ml, 2.2 mmol) were added to a solution of intermediate 9a (650 mg, 2.77 mmol) in 50 ml of acetonitrile under nitrogen atmosphere at room temperature. The reaction mixture was stirred for 18 h. The reaction mixture was concentrated under vacuum to give the desired product (mixture of diastereoisomers).

GC/MS (method 3A) $R_t$=10.47 min and 10.68 min (diastereoisomeric mixture, ratio trans/cis=8/2)

Intermediate 11a

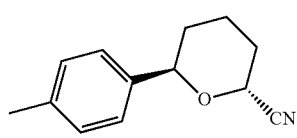

Intermediate 10a was purified by flash chromatography (Biotage SP1 cartridge 25 g, eluent: cyclohexane/ethyl acetate=99/1). 400 mg of diastereomerically pure trans stereoisomer was obtained (racemate, relative configuration assigned by NMR).

GC/MS (method 3A) $R_t$=10.47 min

Intermediate 12a

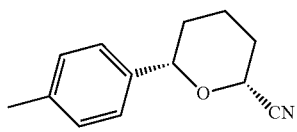

Further elution of the column gave 100 mg of the diastereomerically pure cis stereoisomer (racemate, relative configuration assigned by NMR).

GC/MS (method 3A) $R_t$=10.68 min

Intermediate 12a was also obtained by epimerization of Intermediate 11a: Intermediate 11a (3.2 g, 15 mmol) was dissolved in 40 ml of tetrahydrofurane. Potassium tert-butoxide (178 mg, 1 mmol) was added and the reaction mixture was stirred at room temperature for 0.5 h. The solid was removed by filtration and the reaction mixture was concentrated under vacuum. The crude product was purified by flash chromatography (Biotage SP1 cartridge 50 g, eluent: cyclohexane/ethyl acetate=99/1). 1.45 g of the desired cis diastereoisomer were obtained.

Intermediate 13a

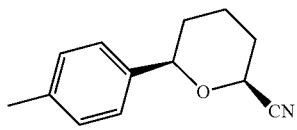

Racemic Intermediate 12a (1.17 g, 2.06 mmol) was separated by chiral HPLC (semi-preparative column). 400 mg (2.0 mmol) were obtained as single enantiomer.

Chiral HPLC (method 2I isocratic): $R_t$=8.74 min

Intermediate 14a

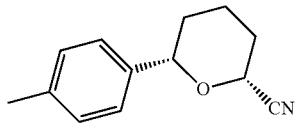

Further elution of the column gave 390 mg (1.94 mmol) of the corresponding single enantiomer.

Chiral HPLC (method 2I isocratic): $R_t$=9.06 min

Absolute stereochemistry was determined by X-ray crystallography:

Absolute stereochemistry was derived from the refinement of anomalous dispersion data.

While an unambiguous assignment is not possible due to the lack of heavy atoms, the Flack parameter gave a clear tendency toward the indicated chiral configuration.

Crystal Data: $C_{13}H_{15}N_1O_1 M_r$=201.26, orthorhombic, $P2_12_12_1$, a=8.0519(16) Å, b=11.185(2) Å, c=12.637(3) Å, V=1138.2(4) Å$^3$, Z=4, $D_x$=1.175 g/cm$^3$, l=1.542 Å, m=0.58 mm$^{-1}$, F(000)=423, T=100(1) K. Data Collection: 12235 measured reflections, 1888/1130 unique, Rint=0.079.

Refinement: 138 parameters; hydrogen atoms were included as riding atoms, S=1.02, RI=0.052 for 1393 reflections with Fo>4sig(Fo), wR=0.128 (Weight w=1/[s$^2$(Fo$^2$)+(0.0864P)$^2$+ 0.0P] where P=(Fo$^2$+2Fc$^2$)/3, largest difference peak: 0.31 e/Å$^3$; largest difference hole −0.22 e/Å$^3$, Flack=0.2(5).

Intermediate 15a

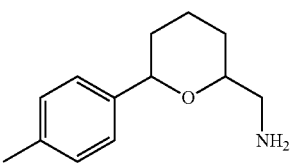

Intermediate 10a was dissolved in 20 ml of tetrahydrofurane, a 1M solution of borane-tetrahydrofurane complex (3.28 ml, 3.28 mmol) was added and the reaction mixture was stirred at room temperature for 18 h. 20 ml of a saturated aqueous sodium bicarbonate solution and 50 ml of dicholometane were added. The organic layer was dried over magnesium sulfate and concentrated under vacuum 90 mg (0.44 mmol) of the desired product were obtained.

Intermediate 16a

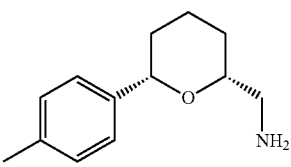

was synthesized in analogy to Intermediate 15a starting from intermediate 12a.

Intermediate 17a

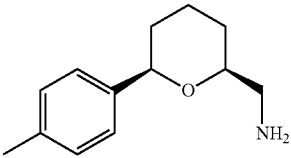

was synthesized in analogy to Intermediate 15a starting from intermediate 13a (absolute stereochemistry as shown).

Intermediate 18a

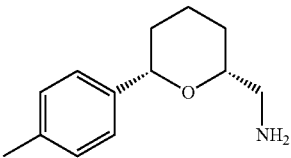

was synthesized in analogy to intermediate 15a starting from intermediate 14a (absolute stereochemistry as shown).

Intermediate 19a

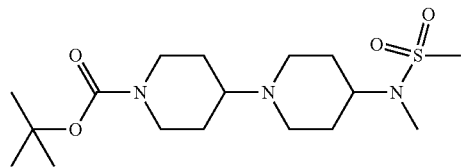 [SMILES: CN(C1CCN(C2CCN(C(=O)OC(C)(C)C)CC2)CC1)S(C)(=O)=O]

N-methyl-N-piperidin-4-yl-methanesulfonamide hydrochloride (11 g, 47.91 mmol; WO2009/47161) was suspended in 200 ml of 1,2-dichloroethane, N,N-diisopropylethylamine (17.12 ml, 96.17 mmol) and commercially available 1-(tert-butoxycarbonyl)-piperidin-4-one (9.58 g, 48.08 mmol) were added and the reaction mixture was stirred at room temperature for 30 min. Sodium triacetoxyborohydride (12.23 g, 57.50 mmol) was added and the reaction mixture was stirred at room temperature for 72 h. The reaction mixture was diluted with dichloromethane and washed with an aqueous saturated sodium bicarbonate solution. The organic phase was dried over sodium sulfate and concentrated under vacuum. The crude product was purified by flash chromatography (Biotage SP1; silica gel cartridge: 65i; eluent: ethyl acetate/methanol=50/50%) to obtain 7.2 g (19.2 mmol) of the desired compound.

Intermediate 20a

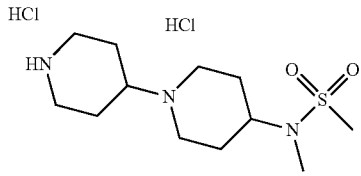 [SMILES: Cl ; Cl ; CN(C1CCN(C2CCNCC2)CC1)S(C)(=O)=O]

Intermediate 19a (7.2 g, 19.2 mmol) was suspended in 20 ml of 1,4-dioxane, a 4M solution of hydrochloric acid (48 ml, 192 mmol) in 1,4-dioxane was added dropwise. The reaction mixture was stirred at room temperature overnight. The reaction mixture was concentrated under vacuum. 6.3 g (18 mmol) of the desired compound were obtained.

The following intermediates were synthesized in analogy to Intermediates 19a and 20a.

| Starting intermediate | Source/Reference | Starting intermediate | Source/Reference | Carbamate Intermediate | STRUCTURE | Diamino Intermediate | STRUCTURE |
|---|---|---|---|---|---|---|---|
| 1-(tert-butoxycarbonyl)-4-oxopiperidine | commercially available | 22b | — | 19b | | 20b | |
| 1-(tert-butoxycarbonyl)-4-oxopiperidine | commercially available | 22c | — | 19c | | 20c | |

| Starting intermediate | Source/Reference | Starting intermediate | Source/Reference | Carbamate Intermediate | STRUCTURE | Diamino Intermediate | STRUCTURE |
|---|---|---|---|---|---|---|---|
| 3-Fluoro-tetrahydro-pyran-4-one | WO2003/93231 | 4-amino-piperidine-1-carboxylic acid tert-butyl-ester | Commercially available | 19d | 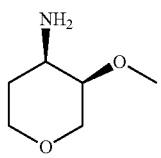 | 20d | 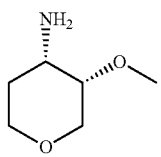 |

Intermediate 21b

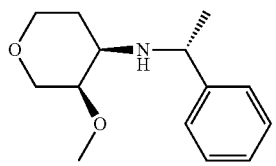 [SMILES: CO[C@H]1COCC[C@H]1N[C@H](C)c1ccccc1]

3-Methoxy-tetrahydro-pyran-4-one* (1 g, 7.68 mmol), commercially available (R)-(+)-1-phenylethylamine (0.99 ml, 7.68 mmol) and Raney-Nickel (200 mg) in 10 ml of dry ethanol were stirred under a hydrogen atmosphere (5 bar) for 15 days. The reaction mixture was diluted with 20 ml of methanol and 20 ml of tetrahydrofurane, stirred for 15 minutes, filtered on a celite pad and concentrated under vacuum. The crude product was loaded on a SCX cartridge (50 g). The cartridge was washed with methanol and the desired product was eluted with a 7 M solution of ammonia in methanol. The basic organic phase was concentrated under vacuum and the crude product was purified by flash chromatography (dichloromethane/methanol=98/2%) to obtain 710 mg (3.02 mmol) of the desired product as single stereoisomer (diastereoisomeric purity confirmed and relative cis configuration assigned by NMR).
* Tetrahedron Letters, 2005, 447-450

GC/MS (method 3B) $R_t$=35.04 min

Intermediate 21c

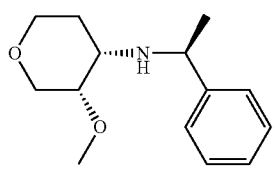 [SMILES: CO[C@@H]1COCC[C@@H]1N[C@@H](C)c1ccccc1]

was synthesised in analogy to Intermediate 21b, starting from 3-Methoxy-tetrahydro-pyran-4-one and commercially available (S)-(−)-1-phenylethylamine (diastereoisomeric purity confirmed and relative cis configuration assigned by NMR).

GC/MS (method 3B) $R_t$=35.04 min

Intermediate 22b

Intermediate 21b (1.18 g, 5.01 mmol), Pd/C 10% (200 mg) and acetic acid (0.3 ml, 5.01 mmol) in 20 ml of methanol were stirred under a hydrogen atmosphere (5 bar) for 18 h. The reaction mixture was diluted with 20 ml of methanol, stirred for 15 minutes, filtered on a celite pad and concentrated under vacuum. The crude product was loaded on a SCX cartridge (50 g). The cartridge was wash with methanol and the desired product was eluted with a 7 M solution of ammonia in methanol. The basic organic phase was concentrated under vacuum and 513 mg (3.91 mmol) of the desired product were obtained as single stereoisomer Intermediate 22c was synthesised in analogy to Intermediate 22b, starting from Intermediate 21c Intermediate 23a Commercially available 5-bromo-4-methylnicotinic acid (50 mg, 231 µmol), TBTU (89 mg, 278 µmol) and N,N-diisopropylethylamine (142 µl, 856 µmol) were dissolved in 1.5 ml DMF. Then, intermediate 20a (80 mg, 231 µmol) was added and the reaction mixture was stirred for 30 min. The reaction mixture was diluted with dichloromethane and washed with an aqueous saturated sodium bicarbonate solution. The organic layer was dried over sodium sulfate and concentrated in vacuum. The residue was purified by reversed phase HPLC to give the desired product (50 mg, 106 μmol).

The following intermediate was synthesised in analogy to Intermediate 23a:

| Starting amine | Bromo Intermediate | STRUCTURE |
|---|---|---|
| 20c | 23b | 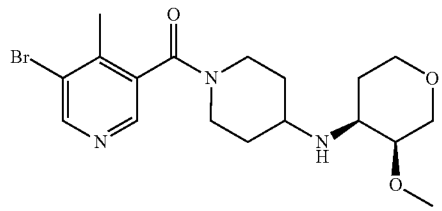 [SMILES: CO[C@@H]1COCC[C@@H]1NC1CCN(C(=O)c2cncc(Br)c2C)CC1] |
| 20b | 23c | 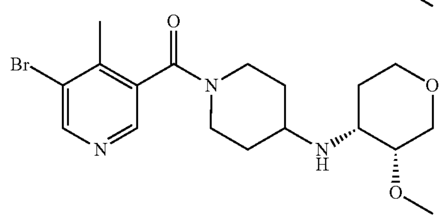 |

Intermediate 24a

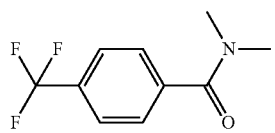

To a solution of commercially available 4-(trifluoromethyl)-benzoyl chloride (25 g, 112 mmol) in 250 ml dry tetrahydrofurane under nitrogen atmosphere, dimethylamine dihydrochloride (14.7 g, 180 mmol) and potassium carbonate (49.62 g, 360 mmol) were added at 0° C. The reaction mixture was stirred at room temperature for 18 h. The solvent was removed under vacuum, the crude product was dissolved in ethyl acetate. The organic phase was washed with brine, dried over sodium sulfate and concentrated under vacuum. The crude product was used in the next step without any purification.

Intermediate 25a

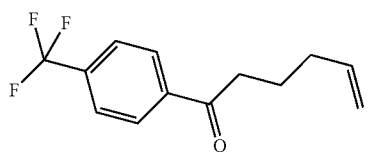 [SMILES: C=CCCCC(=O)c1ccc(C(F)(F)F)cc1]

Intermediate 24a (25 g) was dissolved in 125 ml of dry tetrahydrofurane and the reaction mixture was cooled to 0° C. 350 ml of a cooled 0.5 M solution of (pent-4-enyl)magnesium bromide (Liebigs Annalen der Chemie 1982, 1478) was added and the reaction mixture was stirred at room temperature for 18 h. The reaction mixture was quenched with a saturated aqueous ammonium chloride solution. The organic phase was separated, dried over sodium sulfate and concentrated under vacuum. The crude product was purified by flash chromatography to give 25 g of the desired product.

Intermediate 26a

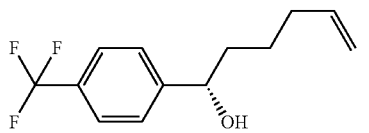 [SMILES: C=CCCC[C@H](O)c1ccc(C(F)(F)F)cc1]

Intermediate 25a was added dropwise to a suspension of (S,S)-teth-TsDpen ruthenium chloride (20 mg, 0.032 mmol; Johnson Matthey Catalysts) in 200 ml formic acid/triethylamine complex under argon atmosphere.

The reaction mixture was warmed to 70° C. for 18 h. Then, water was added and the reaction mixture was extracted with diethyl ether. The organic phase was separated, dried over sodium sulfate and concentrated under vacuum. The crude product (40 g) was used in the next step without any purification.

Stereochemistry in analogy to Organic Letters 2000, 1749-51.

The following intermediates were synthesized in analogy to Intermediates 24a, 25a and 26a.

| | synthesis in analogy to intermediate 24a | | | synthesis in analogy to intermediate 25a | | synthesis in analogy to intermediate 26a | | |
|---|---|---|---|---|---|---|---|---|
| Starting Benzoyl chloride | Source | Amide Intermediate | STRUCTURE | Keton Intermediate | STRUCTURE | Alcohol Intermediate | STRUCTURE | Stereochemistry |
| 4-methyl-benzoyl chloride | Commercially available | 24b | | 25b | | 26b | | in analogy to Organic Letters 2000, 1749-51 |

-continued

| synthesis in analogy to intermediate 24a | | | | synthesis in analogy to intermediate 25a | | synthesis in analogy to intermediate 26a | | |
|---|---|---|---|---|---|---|---|---|
| Starting Benzoyl chloride | Source | Amide Intermediate | STRUCTURE | Keton Intermediate | STRUCTURE | Alcohol Intermediate | STRUCTURE | Stereochemistry |
| 4-(trifluoromethoxyl) benzoyl chloride | Commercially available | 24c | *[structure]* | 25c | *[structure]* | 26c | *[structure]* | in analogy to Organic Letters 2000, 1749-51 |

Intermediate 27a

*[structure of tetrahydropyran with 4-(trifluoromethyl)phenyl and CH2I substituents]*

To a suspension of sodium bicarbonate (40.6 g, 482 mmol) in 600 ml of acetonitrile, a solution of Intermediate 26a (40 g) in 100 ml of acetonitrile was added, followed by the addition of iodine (122 g, 482 mmol). The reaction mixture was stirred at room temperature for 1 h, then 1000 ml of a saturated aqueous $Na_2S_2O_3$ solution were added. The mixture was extracted with diethyl ether. Then, the organic phase was separated, dried over sodium sulfate and concentrated under vacuum. The crude product was purified by flash chromatography to yield 29 g of the desired cis stereoisomer.

Relative stereochemistry was assigned by $^1$H-NMR.

Intermediate 28a

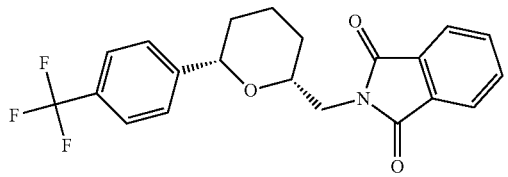 [SMILES: O=C1c2ccccc2C(=O)N1C[C@H]1CCC[C@@H](c2ccc(C(F)(F)F)cc2)O1]

Commercially available phthalimide potassium salt (17.4 g, 94.0 mmol) was added to a solution of Intermediate 27a (29 g, 78.4 mmol) in 250 ml DMF. The reaction mixture was stirred at 90° C. for 18 h. The reaction mixture was concentrated under vacuum, diethyl ether was added and the organic phase was washed with an aqueous 1 M sodium hydroxide solution. The organic layer was separated, dried over sodium sulfate and concentrated under vacuum. The crude product (28.7 g) was re-crystallised using 350 ml of methylcyclohexane. 9.5 g of enantiomerically enriched product were obtained.

Enantiomerical purity was determined by chiral HPLC (Method 2Ja):

$R_t$ (preferred stereoisomer)=6.69 min $R_t$ (second stereoisomer)=6.00 min

Repeated re-crystallisations with methylcyclohexane allowed to increase the yield of the enantiopure preferred stereoisomer.

The following intermediates were synthesized in analogy to Intermediates 27a and 28a.

| synthesis in analogy to intermediate 27a | | | synthesis in analogy to intermediate 28a | | | |
|---|---|---|---|---|---|---|
| | | | | | Chiral | |
| Starting Intermediate | Iodo Intermediate | STRUCTURE | Phtalimide Intermediate | STRUCTURE | HPLC method | $R_t$ (min) |
| 26b | 27b | | 28b | | Method 2Ja | $R_t$ (preferred s stereoisomer) = 6.27<br>$R_t$ (second stereoisomer) = 5.62 |
| 26c | 27c | | 28c | | Method 2Ja | $R_t$ (preferred stereoisomer) = 6.14<br>$R_t$ (second stereoisomer) = 5.64 |

Intermediate 29a

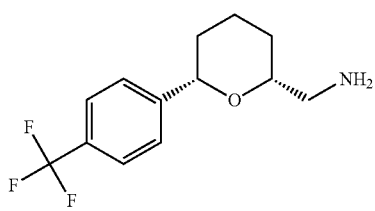 [SMILES: NC[C@H]1CCC[C@@H](c2ccc(C(F)(F)F)cc2)O1]

Ethanolamine (8.84 ml, 146.4 mmol) was added to a solution of Intermediate 28a (9.5 g, 24.4 mmol) in 100 ml of toluene. The reaction mixture was stirred at 70° C. for 3 h. Then, the mixture was cooled to room temperature and diluted with water and ethyl acetate. The organic phase was separated and washed with an aqueous 1M solution of sodium hydroxide, dried over sodium sulfate and concentrated under vacuum to give the desired product (6.1 g). The crude product was used in the next step without any purification.

The following intermediates were synthesized in analogy to Intermediate 29a.

| Starting Intermediate | Amine Intermediate | STRUCTURE |
|---|---|---|
| 28b | 18a | 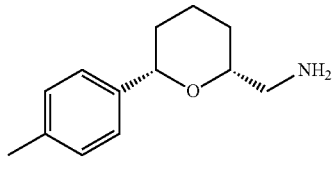 |
| 28c | 29c | 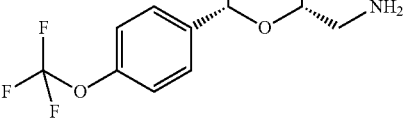 |

Intermediate 30a

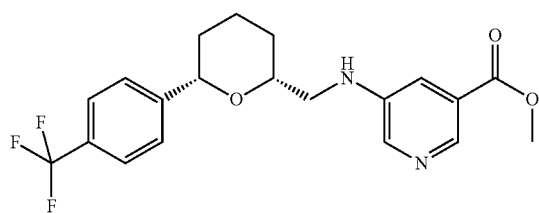 [SMILES: COC(=O)c1cncc(NC[C@H]2CCC[C@@H](c3ccc(C(F)(F)F)cc3)O2)c1]

A mixture of commercially available methyl 5-bromonicotinate (150 mg, 694 μmol, intermediate 29a (150 mg, 579 μmol), cesium carbonate (321 mg, 984 μmol, tris(dibenzylideneacetone)dipalladium (79 mg, 87 μmol) and XPhos (116 mg, 243 μmol) in 4.5 ml toluene and 1.5 ml dioxane was heated under argon atmosphere over night at 110° C. The solvent was removed under vacuum and the residue was purified by reversed phase HPLC to give the desired product (224 mg, 568 μmol).

Intermediate 31a

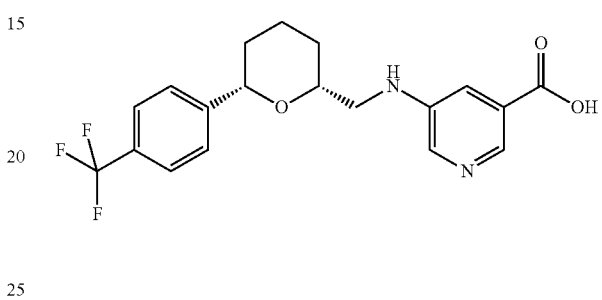

A solution of lithium hydroxide (56 mg, 2.3 mmol) in 10 ml water was added to a solution of intermediate 30a (308 mg, 781 μmol) in 10 ml THF. The reaction mixture was stirred for 1 h. The mixture was diluted with ethyl acetate and water and the phases were separated. The aqueous layer was acidified with 4 N HCl and extracted with dichloromethane; the organic layer was dried over sodium sulfate and concentrated under vacuum to give the crude product (290 mg, 762 μmol) which was used in the next step without purification.

The following intermediates were synthesized in analogy to Intermediates 30a and 31a.

| Starting intermediate | Ester intermediate | Structure | Acid intermediate | Structure |
|---|---|---|---|---|
| 18a | 30b | 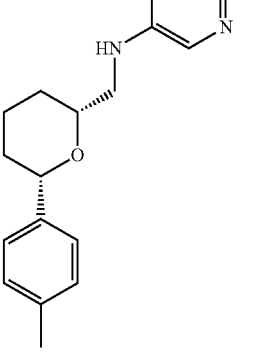 | 31b | 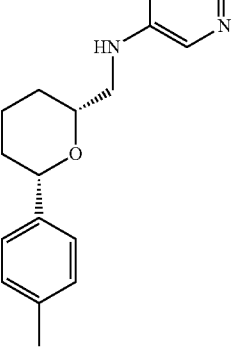 |

SYNTHESIS OF EXAMPLES

The examples of this invention are synthesized according to the following general synthetic procedures:

Synthetic Procedure A

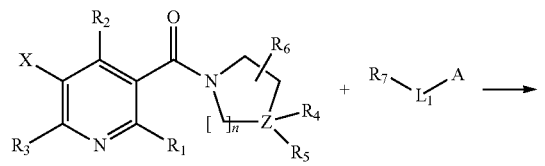

X=halogen

Examples: 1-6, 6a-6d

Synthetic Procedure B

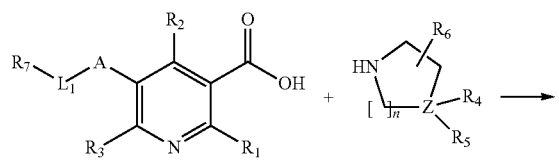

-continued

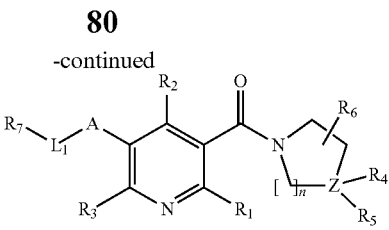

Examples: 7-10

Example 1

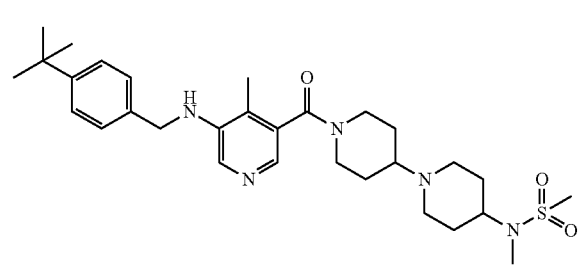 [SMILES: Cc1c(NCc2ccc(C(C)(C)C)cc2)cncc1C(=O)N1CCC(N2CCC(N(C)S(C)(=O)=O)CC2)CC1]

A mixture of intermediate 23a (50 mg, 106 µmol), 4-tert-butyl-benzylamine (17 mg, 106 µmol), cesium carbonate (103 mg, 317 µmol), palladium acetate (2.4 mg, 11 µmol) and BINAP (13 mg, 21 µmol) in 1 ml toluene and 0.25 ml dioxane was heated under argon atmosphere over night at 100° C. After cooling to room temperature, the mixture was purified by reversed phase HPLC to give the desired product (25 mg, 45 µmol).

HPLC (Method 2Ca): $R_t$ (min)=1.60

$[M+H]^+$=556

The following examples were synthesized in analogy to the preparation of Example 1.

| Ex # | STRUCTURE | Intermediate | Amine | $[M+H]^+$ | HPLC $R_t$ (min) | Method |
|---|---|---|---|---|---|---|
| 2 | ![structure] | 23a | 4 | 582 | 1.99 | 2Ca |
| 3 | ![structure] | 23b | 18a | 537 | 1.57 | 2Ca |

Example 4

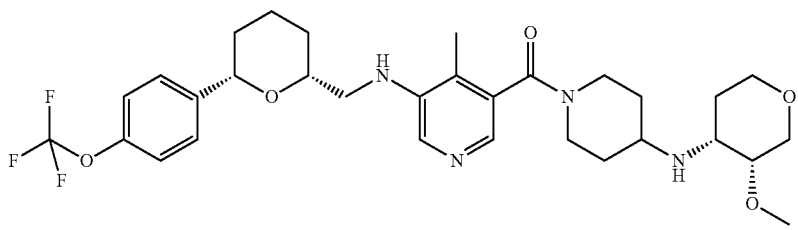 [SMILES: CO[C@H]1COCC[C@H]1NC1CCN(C(=O)c2cncc(NC[C@H]3CCC[C@@H](c4ccc(OC(F)(F)F)cc4)O3)c2C)CC1]

A mixture of intermediate 23c (101 mg, 245 µmol), intermediate 29c (45 mg, 163 µmol), cesium carbonate (91 mg, 278 µmol), tris(dibenzylideneacetone)dipalladium (22 mg, 24 µmol) and XPhos (33 mg, 69 µmol) in 1.5 ml toluene and 0.5 ml dioxane was heated under argon atmosphere over night at 110° C. After cooling to room temperature, the mixture was purified by reversed phase HPLC to give the desired product (19 mg, 31 µmol).

HPLC (Method Y1_1): $R_t$ (min)=1.356

[M+H]$^+$=607

The following examples were synthesized in analogy to the preparation of Example 4.

| Ex # | STRUCTURE | Intermediate | Amine | [M + H]$^+$ | HPLC $R_t$ (min) | Method |
|---|---|---|---|---|---|---|
| 5 | 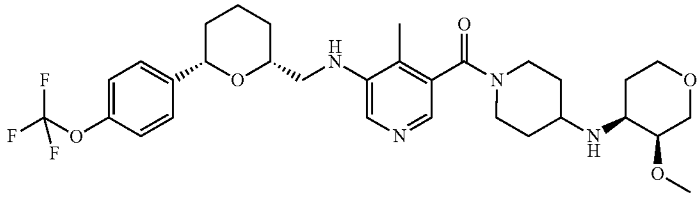 [SMILES: CO[C@@H]1COCC[C@@H]1NC1CCN(C(=O)c2cncc(NC[C@H]3CCC[C@@H](c4ccc(OC(F)(F)F)cc4)O3)c2C)CC1] | 23b | 29c | 607 | 1.341 | B-STD |
| 6 | 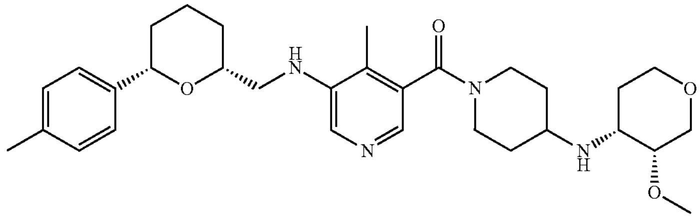 | 23c | 18a | 537 | 0.960 | Z1_2 |
| 6a | 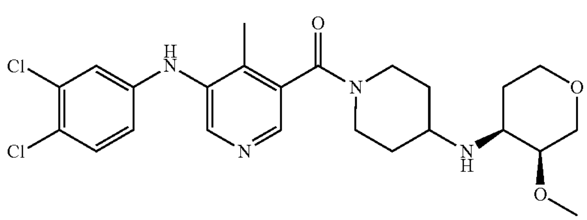 [SMILES: CO[C@@H]1COCC[C@@H]1NC1CCN(C(=O)c2cncc(Nc3ccc(Cl)c(Cl)c3)c2C)CC1] | 23b | 3,4-dichloro-aniline* | 493 | 0.876 | Z1_2 |
| 6b | 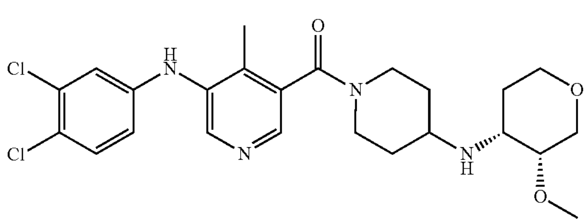 [SMILES: CO[C@H]1COCC[C@H]1NC1CCN(C(=O)c2cncc(Nc3ccc(Cl)c(Cl)c3)c2C)CC1] | 23c | 3,4-dichloro-aniline* | 493 | 0.874 | Z1_2 |

| Ex # | STRUCTURE | Intermediate | Amine | [M + H]+ | HPLC Rt (min) | Method |
|---|---|---|---|---|---|---|
| 6c | 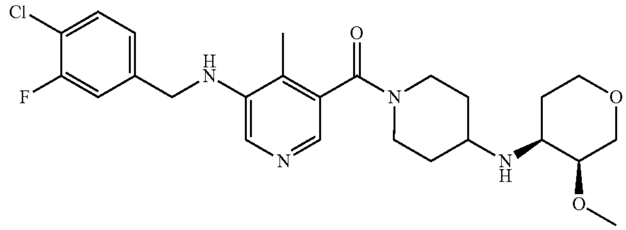 [SMILES: CO[C@@H]1COCC[C@@H]1NC1CCN(C(=O)c2cncc(NCc3ccc(Cl)c(F)c3)c2C)CC1] | 23b | 4-Chloro-3-fluoro-benzylamine* | 491 | 0.736 | Z1_2 |
| 6d | 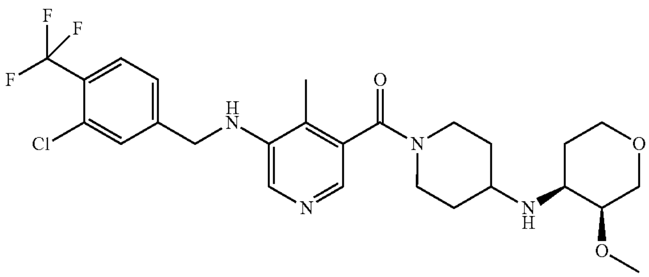 [SMILES: CO[C@@H]1COCC[C@@H]1NC1CCN(C(=O)c2cncc(NCc3ccc(C(F)(F)F)c(Cl)c3)c2C)CC1] | 23b | 3-Chloro-4-trifluoromethyl-benzylamine* | 541 | 0.866 | Z1_2 |

*Commercially available

Example 7

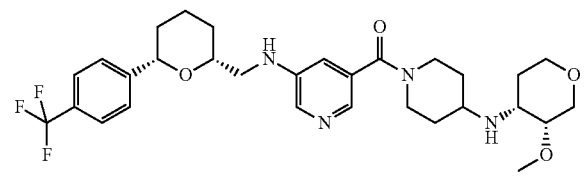 [SMILES: CO[C@H]1COCC[C@H]1NC1CCN(C(=O)c2cncc(NC[C@H]3CCC[C@@H](c4ccc(C(F)(F)F)cc4)O3)c2)CC1]

Intermediate 31a (90 mg, 237 μmol), TBTU (84 mg, 260 μmol) and N,N-diisopropylethylamine (333 μl, 1.9 mmol) were dissolved in 1 ml DMF. Then, intermediate 20b (89 mg, 355 μmol) was added and the reaction mixture was stirred for 45 min. The reaction mixture was directly purified by reversed phase HPLC to give the desired product (120 mg, 208 μmol).

HPLC (Method Z1_2): $R_t$ (min)=1.023

[M+H]$^+$=577

The following examples were synthesized in analogy to the preparation of Example 7.

| Ex # | STRUCTURE | Intermediate | Amine | [M + H]+ | HPLC Rt (min) | Method |
|---|---|---|---|---|---|---|
| 8 | 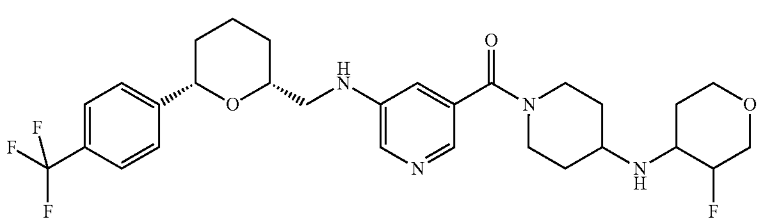 [SMILES: O=C(c1cncc(NC[C@H]2CCC[C@@H](c3ccc(C(F)(F)F)cc3)O2)c1)N1CCC(NC2CCOCC2F)CC1] | 31a | 20d | 565 | 1.019 | Z1_2 |
| 9 | 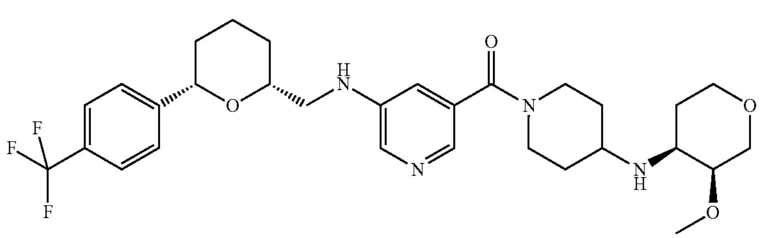 [SMILES: CO[C@@H]1COCC[C@@H]1NC1CCN(C(=O)c2cncc(NC[C@H]3CCC[C@@H](c4ccc(C(F)(F)F)cc4)O3)c2)CC1] | 31a | 20c | 577 | 1.023 | Z1_2 |

| Ex # | STRUCTURE | Intermediate | Amine | [M + H]+ | HPLC R_t (min) | Method |
|---|---|---|---|---|---|---|
| 10 | 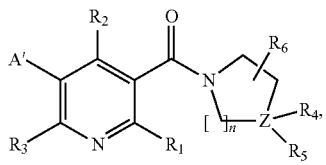 | 31b | 20c | 523 | 0.959 | Z1_2 |

The invention claimed is:

1. A compound according to formula (Ia), $$\text{(Ia)}$$

wherein A' is $-NH-L_1-R_7$, wherein $L_1$ is a linker selected from a bond or $-C_1-C_2$-alkylene, wherein $R_7$ is a ring selected from among $-C_3-C_8$-cycloalkyl, $-C_3-C_8$-heterocyclyl, $-C_5-C_{10}$-aryl, and $-C_5-C_{10}$-heteroaryl, wherein the ring $R_7$ is optionally substituted with one or more groups selected from among $-CF_3$, $-C_1-C_6$-alkyl, $-O-CF_3$, $-CN$, $-O-C_1-C_6$-alkyl, $-C_1-C_6$-alkenyl, and $-C_1-C_6$-alkynyl, and -halogen, or wherein the ring $R_7$ is optionally substituted with one or more groups selected from among $-C_5-C_{10}$-aryl, $-C_5-C_{10}$-heteroaryl, $-C_3-C_8$-cycloalkyl, $-C_3-C_8$-heterocyclyl, optionally being substituted by one or more groups selected from among $-OH$, $-NH_2$, $-C_1-C_4$-alkyl, $-O-C_1-C_6$-alkyl, $-CN$, $-CF_3$, $-OCF_3$, halogen, and $=O$, or wherein the ring $R_7$ is optionally further bi-valently substituted on two neighbouring ring atoms, such that an annellated ring is formed by one or more groups selected from among $-C_1-C_6$-alkylene, $-C_2-C_6$-alkenylene and $-C_4-C_6$-alkynylene, in which one or two carbon centers may optionally be replaced by 1 or 2 hetero atoms selected from N, O and S, the bivalent group being optionally substituted by one or more groups selected from $-OH$, $-NH_2$, $-C_1-C_4$-alkyl, $-O-C_1-C_6$-alkyl, $-CN$, $-CF_3$, $-OCF_3$, halogen, and $=O$, wherein $R_1$ is $-H$;

wherein $R_2$ is selected from among $-H$, -halogen, $-CN$, $-O-C_1-C_4$-alkyl, $-C_1-C_4$-alkyl, $-CH=CH_2$, $-C\equiv CH$, -cyclopropyl, $-CF_3$, $-OCF_3$, $-OCF_2H$, and $-OCFH_2$;

wherein $R_3$ is $-H$;

wherein $R_6$ is selected from among $-H$, $-C_1-C_4$-alkyl, $-OH$, $-O-C_1-C_4$-alkyl, -halogen, $-CN$, $-CF_3$, and $-OCF_3$;

wherein Z is C;
wherein n is 2;

wherein $R_4$ and $R_5$ are independently selected from among an electron pair, $-H$, and a group selected from among $-C_1-C_6$-alkyl, $-NH_2$, $-C_3-C_8$-cycloalkyl, $-C_3-C_8$-heterocyclyl, $-C_5-C_{10}$-aryl, $-C_5-C_{10}$-heteroaryl, and $-C(O)-N(R_8,R_{8'})$, with $R_8$ and $R_{8'}$ independently being selected from among $-H$, and $-C_1-C_6$-alkyl, and wherein $R_4$ and $R_5$ if different from an electron pair or $-H$ are optionally independently substituted with one or more groups selected from among -halogen, $-OH$, $-CF_3$, $-CN$, $-C_1-C_6$-alkyl, $-O-C_1-C_6$-alkyl, $-O-C_3-C_8$-cycloalkyl, $-O-C_3-C_8$-heterocyclyl, $-O-C_5-C_{10}$-aryl, $-O-C_5-C_{10}$-heteroaryl, $-C_0-C_6$-alkylene-CN, $-C_0-C_4$-alkylene-O-$C_1-C_4$-alkyl, $-C_0-C_4$-alkylene-O-$C_3-C_8$-cycloalkyl, $-C_0-C_4$-alkylene-O-$C_3-C_8$-heterocyclyl, $-C_0-C_4$-alkylene-O-$C_5-C_{10}$-aryl, $-C_0-C_4$-alkylene-O-$C_5-C_{10}$-heteroaryl, $-C_0-C_4$-alkylene-Q-$C_0-C_4$-alkyl-N($R_9$,$R_{9'}$), $-C_0-C_4$-alkylene-N($R_{10}$)-Q-$C_1-C_4$-alkyl, $-C_0-C_4$-alkylene-N($R_{10}$)-Q-$C_3-C_8$-cycloalkyl, $-C_0-C_4$-alkylene-N($R_{10}$)-Q-$C_3-C_8$-heterocyclyl, $-C_0-C_4$-alkylene-N($R_{10}$)-Q-$C_5-C_{10}$-aryl, $-C_0-C_4$-alkylene-N($R_{10}$)-Q-$C_5-C_{10}$-heteroaryl, $-C_0-C_4$-alkylene-Q-N($R_{11}$,$R_{11'}$), $-C_0-C_4$-alkylene-N($R_{12}$)-Q-N($R_{13}$,$R_{13'}$), $-C_0-C_4$-alkylene-$R_{14}$, $-C_0-C_4$-alkylene-Q-$C_1-C_6$-alkyl, $-C_0-C_4$-alkylene-Q-$C_3-C_8$-cycloalkyl, $-C_0-C_4$-alkylene-Q-$C_3-C_8$-heterocyclyl, $-C_0-C_4$-alkylene-Q-$C_5-C_{10}$-aryl, $-C_0-C_4$-alkylene-Q-$C_5-C_{10}$-heteroaryl, $-C_0-C_4$-alkylene-O-Q-N($R_{15}$,$R_{15'}$), and $-C_0-C_4$-alkylene-N($R_{16}$)-Q-O-($R_{17}$), wherein Q is selected from among $-C(O)-$, and $-SO_2-$, wherein $R_{12}$, $R_{16}$, are independently selected from among $-H$, $-C_1-C_6$-alkyl, and $-C_3-C_6$-cycloalkyl, wherein $R_9$, $R_{9'}$, $R_{10}$, $R_{11}$, $R_{11'}$, $R_{13}$, $R_{13'}$, $R_{15}$, $R_{15'}$, are independently selected from among $-H$, $-C_1-C_6$-alkyl, and $-C_3-C_6$-cycloalkyl, or wherein $R_9$ and $R_{9'}$, $R_{11}$ and $R_{11'}$, $R_{13}$ and $R_{13'}$, $R_{15}$ and $R_{15'}$ together form a $-C_2-C_6$-alkylene group, wherein $R_{14}$ and $R_{17}$ are independently selected from among $-H$, $-C_1-C_6$-alkyl, $-C_5-C_{10}$-aryl, $-C_5-C_{10}$-heteroaryl, $-C_3-C_8$-cycloalkyl, and $-C_3-C_8$-heterocyclyl, wherein said $-C_3-C_8$-heterocyclyl optionally comprises nitrogen and/or $-SO_2-$ in the ring, and wherein $R_{14}$ and $R_{17}$ are optionally substituted with one or more groups selected from among $-OH$, $-OCH_3$, $-CF_3$, $-OCF_3$, $-CN$, -halogen, $-C_1-C_4$-alkyl, $=O$, and $-SO_2-C_1-C_4$-alkyl, or wherein $R_4$ and/or $R_5$ are independently selected from among an electron pair, $-H$, and a group of the structure $-L_2-R_{18}$, wherein $L_2$ is selected from among $-NH-$ and $-N(C_1-C_4$-alkyl)-, wherein $R_{18}$ is selected from among $-C_5-C_{10}$-aryl, $-C_5-C_{10}$-heteroaryl, $-C_3-C_8$-cycloalkyl, and $-C_3-C_8$-heterocyclyl, wherein $R_{18}$ is optionally substituted by one or more groups selected from among halogen, —$CF_3$, —$OCF_3$, —CN, —OH, —O—$C_1$-$C_4$-alkyl, —$C_1$-$C_6$-alkyl, —NH—C(O)—$C_1$-$C_6$-alkyl, —N($C_1$-$C_4$-alkyl)-C(O)—$C_1$-$C_6$-alkyl, —C(O)—$C_1$-$C_6$-alkyl, —S(O)$_2$—$C_1$-$C_6$-alkyl, —NH—S(O)$_2$—$C_1$-$C_6$-alkyl, —N($C_1$-$C_4$-alkyl)-S(O)$_2$—$C_1$-$C_6$-alkyl, and —C(O)—O—$C_1$-$C_6$-alkyl, and wherein $R_4$, $R_5$ and $R_{18}$ are optionally further substituted by spiro-$C_3$-$C_8$-cycloalkyl or spiro-$C_3$-$C_8$-heterocyclyl such that together with $R_4$, $R_5$ and/or $R_{18}$ a spirocycle is formed, wherein said spiro-$C_3$-$C_8$-heterocyclyl optionally comprises one or more groups selected from among nitrogen, —C(O)—, —SO$_2$—, and —N(SO$_2$—$C_1$-$C_4$-alkyl)- in the ring, or wherein $R_4$, $R_5$ and $R_{18}$ are optionally further bi-valently substituted by one or more spirocyclic or annellated ring forming groups selected from among —$C_1$-$C_6$-alkylene, —$C_2$-$C_6$-alkenylene, and —$C_4$-$C_6$-alkynylene, in which one or two carbon centers may optionally be replaced by one or two hetero atoms selected from among N, O and S and which may optionally be substituted by one or more groups on one ring atom or on two neighbouring ring atoms selected from among —OH, —NH$_2$, —$C_1$-$C_3$-alkyl, O—$C_1$-$C_6$-alkyl, —CN, —$CF_3$, —$OCF_3$, and halogen;

or a pharmacologically acceptable salt thereof.

2. The compound of formula (Ia) according to claim 1, wherein
$R_7$ is a ring selected from among-$C_3$-$C_8$-cycloalkyl, and —$C_3$-$C_8$-heterocyclyl, —$C_5$-$C_{10}$-aryl,
wherein the ring $R_7$ is optionally substituted with one or more groups selected from —$C_1$-$C_6$-alkyl,
or wherein the ring $R_7$ is optionally substituted with one or more groups selected from -$C_5$-$C_{10}$-aryl, optionally being substituted by one or more groups selected from among —$C_1$-$C_4$-alkyl, —$CF_3$, —$OCF_3$, and halogen.

3. The compound of formula (Ia) according to claim 1, wherein $R_7$ denotes a group selected from among formula (II)

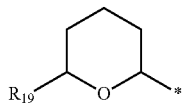

(II)

wherein $R_{19}$ denotes the ring —$C_5$-$C_{10}$-aryl,
wherein the ring $R_{19}$ is optionally substituted with one or more groups selected from —$C_1$-$C_4$-alkyl.

4. The compound of formula (Ia) according to claim 1,
wherein $R_7$ is a ring selected from among —$C_3$-$C_8$-cycloalkyl, and -$C_5$-$C_{10}$-aryl,
wherein the ring $R_7$ is optionally substituted with one or more groups selected from —$C_1$-$C_6$-alkyl,
or wherein the ring $R_7$ is optionally substituted with one or more groups selected from -phenyl, optionally being substituted by one or more groups selected from among —$C_1$-$C_4$-alkyl.

5. The compound of formula (Ia) according to claim 1, wherein $R_2$ is selected from among —H, —O—$C_1$-$C_4$-alkyl, and —$C_1$-$C_4$-alkyl.

6. The compound of formula (Ia) according to claim 1, wherein $R_6$ denotes —H.

7. The compound of formula (Ia) according to claim 1, wherein $R_4$ denotes —H, and wherein $R_5$ denotes a group of the structure -$L_2$-$R_{18}$,
wherein $L_2$ is a group selected from among —NH—, and —N(CH$_3$)—,
wherein $R_{18}$ is —$C_6$-heterocyclyl comprising 1 hetero atom selected from 0,
wherein $R_{18}$ is optionally substituted by —O—CH$_3$;
or wherein $R_4$ denotes —H and $R_5$ is a heterocyclyl selected from pyrrolidine and piperidine wherein said heterocyclyl is optionally substituted with one or more groups selected from —N($C_0$-$C_1$-alkyl)-SO$_2$—CH$_3$.

8. A method for the treatment of inflammatory diseases comprising administering to a patient in need thereof a therapeutic amount of compound according to claim 1.

9. The method according to claim 8, wherein the inflammatory diseases are selected from inflammatory diseases of the respiratory tract.

10. The method according to claim 9, wherein the diseases are selected from chronic obstructive pulmonary disease, asthma, and cystic fibrosis.

11. A method for the treatment of diabetes mellitus comprising administering to a patient in need thereof a therapeutic amount of compound according to claim 1.

12. A method for the treatment of peripheral atherosclerotic disease comprising administering to a patient in need thereof a therapeutic amount of compound according to claim 1.

13. A method for the treatment of diabetic nephropathy comprising administering to a patient in need thereof a therapeutic amount of compound according to claim 1.

14. A method for the treatment of inflammatory and neuropathic pain disease comprising administering to a patient in need thereof a therapeutic amount of compound according to claim 1.

15. The compound of formula (Ia) according to claim 1, wherein the compound is selected from the group consisting of

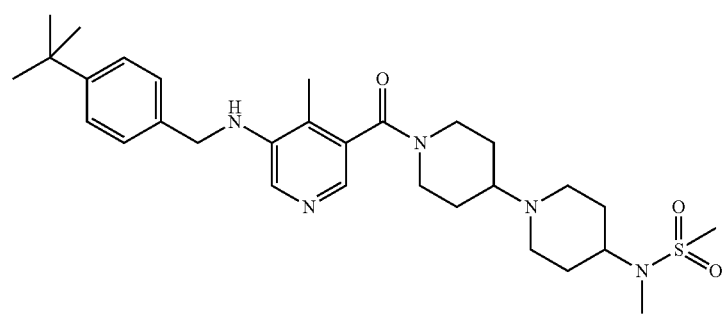

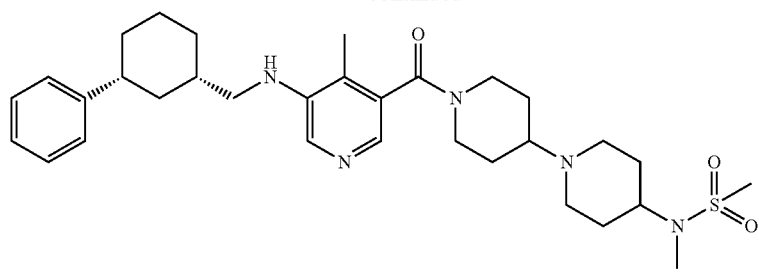
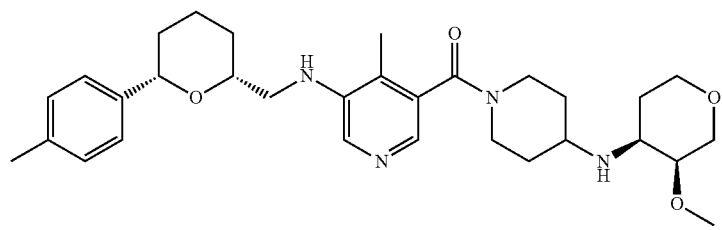
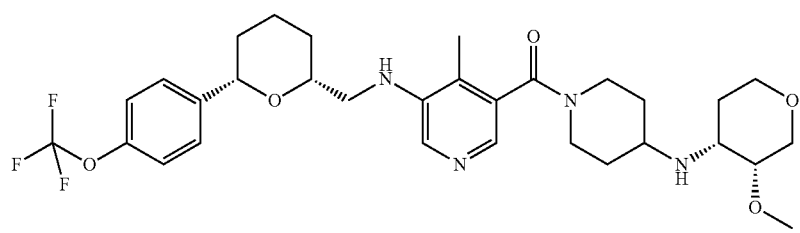
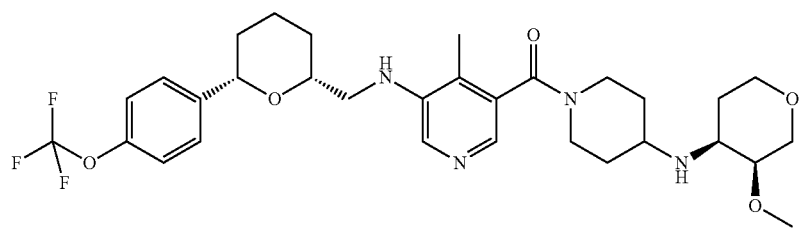
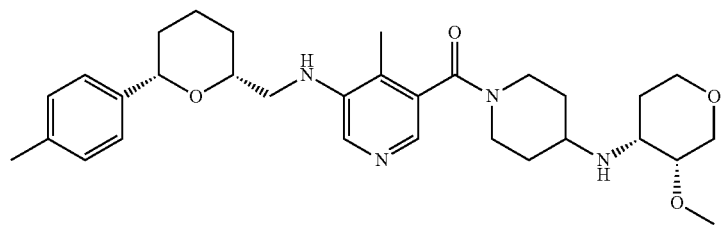
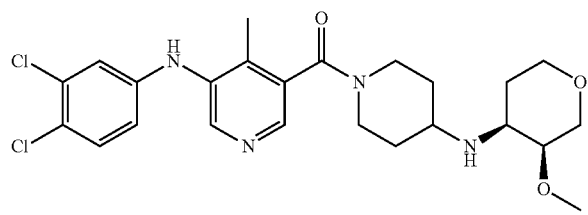
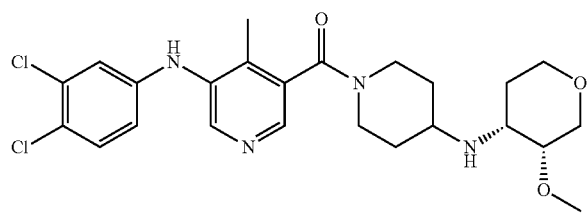

-continued
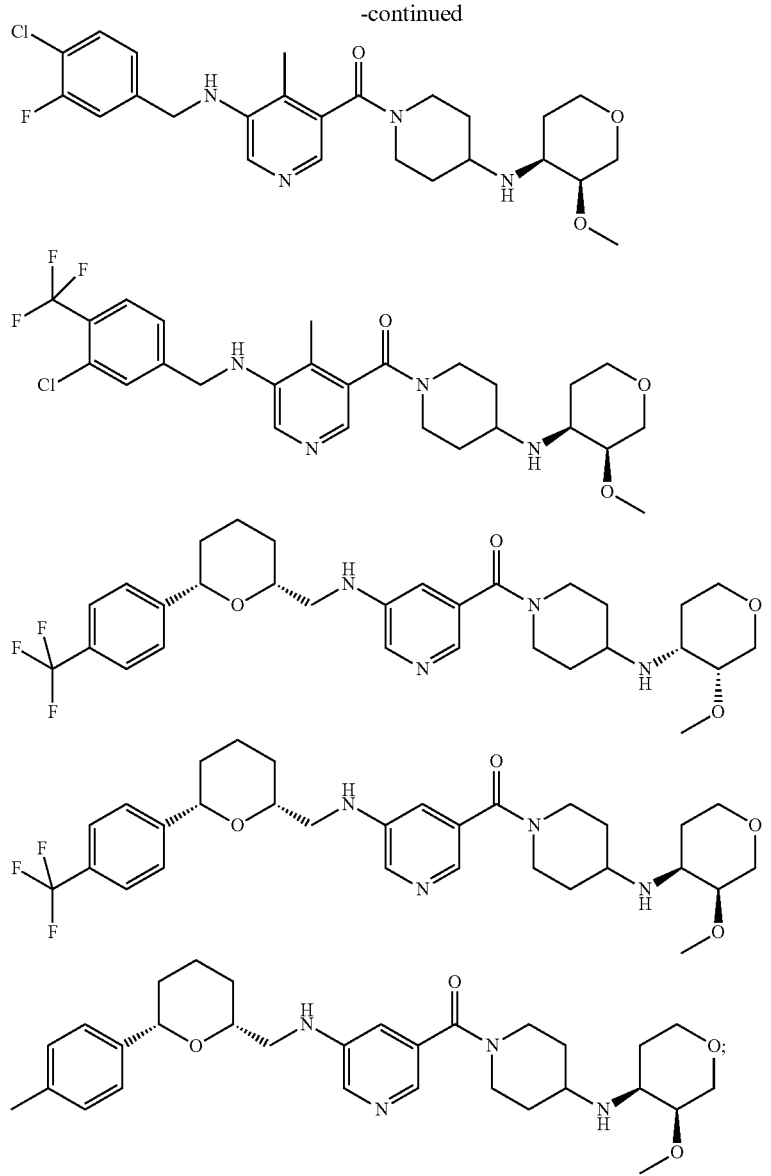
or a pharmacologically acceptable salt thereof.
* * * * *